US006514981B1

(12) United States Patent
Tang et al.

(10) Patent No.: US 6,514,981 B1
(45) Date of Patent: Feb. 4, 2003

(54) METHODS OF MODULATING TYROSINE PROTEIN KINASE FUNCTION WITH INDOLINONE COMPOUNDS

(75) Inventors: Peng Cho Tang, Moraga; Li Sun, Foster City, both of CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/283,657

(22) Filed: Apr. 1, 1999

Related U.S. Application Data

(60) Provisional application No. 60/080,422, filed on Apr. 2, 1998.

(51) Int. Cl.$^7$ .................... A61K 31/404; C07D 209/34; C07D 403/06; C07D 409/06

(52) U.S. Cl. ................ 514/267; 514/291; 514/292; 514/293; 514/411; 514/413; 544/250; 544/251; 546/80; 546/81; 546/82; 546/83; 546/85; 546/89; 548/439; 548/440; 548/441; 548/452

(58) Field of Search .................. 544/250, 251; 546/80, 81, 82, 83, 85, 89; 548/439, 440, 441, 452; 514/267, 291, 292, 293, 411, 414

(56) References Cited

U.S. PATENT DOCUMENTS

| 4,376,110 A | 3/1983 | David et al. ............ 436/513 |
| 4,966,849 A | 10/1990 | Vallee et al. ........... 435/199 |
| 5,217,999 A | 6/1993 | Levitzki et al. ......... 514/613 |
| 5,302,606 A | 4/1994 | Spada et al. ........... 514/357 |
| 5,330,992 A | 7/1994 | Eissenstat et al. ...... 514/312 |
| RE36,256 E | 7/1999 | Spada et al. ........... 514/249 |

FOREIGN PATENT DOCUMENTS

| EP | 0 566 226 A1 | 10/1993 |
| EP | 0 810 217 A1 | 12/1997 |
| WO | 91/13055 | 9/1991 |
| WO | 91/15495 | 10/1991 |
| WO | 92/07830 | 5/1992 |
| WO | 92/20642 | 11/1992 |
| WO | 92/21660 | 12/1992 |
| WO | 94/03427 | 2/1994 |
| WO | 94/10202 | 5/1994 |
| WO | 94/14088 | 7/1994 |
| WO | 95/24190 | 9/1995 |
| WO | 96/00226 | 1/1996 |
| WO | 96/16964 | 6/1996 |
| WO | 96/22976 | 8/1996 |
| WO | 96/40116 | 12/1996 |
| WO | 98/07695 | 2/1998 |
| WO | 98/45708 | 10/1998 |
| WO | 98/50356 | 11/1998 |
| WO | 98/56376 | 12/1998 |
| WO | 99/10325 | 3/1999 |

OTHER PUBLICATIONS

Fendly et al., Characterization of Murine Monoclonal Antibodies Reactive to Either the Human Epidermal Growth Factor Receptor or HER2/neu Gene Product, *Cancer Research* 50:1550–1558 (1990); ©American Association for Cancer Research.

Voller et al., "Ch. 45—Enzyme–Linked Immunosorbent Assay," in *Manual of Clinical Immunology*, $2^{nd}$ edition, Rose and Friedman editors, American Society of Microbiology, Washington, D.C., pp. 359–371 (1980); ©American Society for Microbiology.

Gazit et al., "Tyrphostins. 2. Heterocyclic and alpha–substituted benzylidenmalonotrile tyrphostins as potent inhibitors of EGF receptor and ErbB2neu tyrosine kinases," *J. Med. Chem.* 34(6):1896–1907 (1991).

Levitzki et al., "Tyrosine kinase inhibition: An approach to drug development," *Science* 267:1782–1788 (1995).

Mohammadi et al., "Structures of the tyrosine kinase domain of fibroblast growth factor receptor in complex with inhibitors," *Science* 276(5314):955–960 (1997).

Spada et al., "Small molecule inhibitors of tyrosine kinase activity," *Expert Opinion on Therapeutic Patents* 5(8):805–817 (1995).

Sun et al., "Synthesis and biological evaluations of 3–substituted indolin–2–ones: A novel class of tyrosine kinase inhibitors that exhibit selectivity toward particular receptor tyrosine kinases," *J. Med. Chem.* 41(14):2588–2603 (1998).

Traxler, "Protein tyrosine kinase inhibitors in cancer treatment," *Expert Opinion on Therapeutic Patents* 7(6):571–588 (1997).

Akbasak and Sunar–Akbasak et al., "Oncogenes: cause or consequence in the development of glial tumors," *J. Neurol. Sci.* 111:119–133 (1992).

Andreani et al., "In Vivo Cardiotonic Activity of Pyridylmehtylene–2–indolinones," *Arzneimittel–Forschung Drug Research* 48(II):727–729 (1998).

Arteaga et al., "Blockade of the Type I Somatomedin Receptor Inhibits Growth of Human Breast Cancer Cells in Athymic Mice," *J. Clin. Invest.* 84:1418–1423 (1989).

Baserga, "Oncogenes and the Strategy of Growth Factors," *Cell* 79:927–930 (1994).

Baserga, "The Insulin–like Growth Factor I Receptor: A Key to Tumor Growth?" *Cancer Research* 55:249–252 (1995).

Bolen et al., "The Src family of tyrosine protein kinases in hemopoietic signal transduction," *Faseb J.* 6:3403–3409 (1992).

(List continued on next page.)

*Primary Examiner*—Richard L. Raymond
(74) *Attorney, Agent, or Firm*—Foley & Lardner

(57) ABSTRACT

The invention relates to certain indolinone compounds, their method of synthesis, and a combinatorial library consisting of the indolinone compounds. The invention also relates to methods of modulating the function of protein tyrosine kinases using indolinone compounds and methods of treating diseases by modulating the function of protein tyrosine kinases and related signal transduction pathways.

26 Claims, No Drawings

OTHER PUBLICATIONS

Buzzetti et al., "Cinnamamide Analogs as Inhibitors of Protein Tyrosine Kinases," *II Farmaco* 48:615–636 (1993).

Carpenedo et al., "Identification and Measurement of Oxindole (2–Indolinone) in the Mammalian Brain and Other Rat Organs," *Analytical Biochemistry* 244:74–79 (1997).

Chao, "Growth Factor Signaling: Where is the Specificity?" *Cell* 68:995–997 (1992).

Chen et al., "Effects of 3,3–Dipyridylmethyl–1–Phenyl–2–Indolinone on γ–Aminobutyric Acid Elicited Chloride Current of Snail Central Neuron," *Chinese Journal of Physiology* 40(3):149–156 (1997).

Coppola et al., "A Functional Insulin–Like Growth Factor I Receptor is Required for the Mitogenic and Transforming Activities of the Epidermal Growth Factor Receptor," *Molecular and Cellular Biology* 14:4588–4595 (1994).

Damiani et al., "Inhibition of Copper–Mediated Low Density Lipoprotein Peroxidation by Quinoline and Indoline Nitroxide Radicals," *Biochemical Pharmacology* 48(6):1155–1161 (1994).

Davis et al., "Synthesis and Microbiological Properties of 3–Amino–1–Hydroxy–2–Indoline and Related Compounds," *Journal of Medicinal Chemistry* 16(9):1043–1045 (1973).

De Vries et al., "The fms–Like Tyrosine Kinase, a Receptor for Vascular Endothelial Growth Factor," *Science* 255:989–991 (1992).

Dickson et al., "Tyrosine kinase receptor—nuclear protooncogene interactions in breast cancer," *Cancer Treatment Res.* 61:249–273 (1992).

Fantl et al., "Distinct Phosphotyrosines on a Growth Factor Receptor Bind to Specific Molecules That Mediate Different Signaling Pathways," *Cell* 69:413–423 (1992).

Ferrara and Henzel, "Pituitary Follicular Cells Secrete a Novel Heparin–Binding Growth Factor Specific for Vascular Endothelial Cells," *Biochemical and Biophysical Research Communications* 161:851–858 (1989).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Floege et al., "Factors involved in the regulation of mesangial cell proliferation in vitro and in vivo," *Kidney International* 43:S47–S54 (1993).

Folkman, "Ch. 24. Angiogenesis," *Congress of Thrombis and Haemostasis* (Verstraete et al., eds.) Leuven University Press, Leuven pp. 583–596 (1987).

Folkman, "What is the Evidence that Tumors are Angiogenesis Dependent?" *Journal of the National Cancer Institute* 82:4–6 (1990).

Folkman and Shing, "Angiogenesis," *J. Biol. Chem.* 267:10931–10934 (1992).

Goldring and Goldring, "Cytokines and Cell Growth Control," *Critical Reviews in Eukaryotic Gene Expression* 1:301–326 (1991).

Graziani et al., "Hepatocyte Growth Factor/Scatter Factor Stimulates the Ras–Guanine Nucleotide Exchanger*," *The Journal of Biological Chemistry* 268(13):9165–9168 (1993).

Honegger et al., "Point Mutation at the ATP Binding Site of EGF Receptor Abolishes Protein–Tyrosine Kinase Activity and Alters Cellular Routing," *Cell* 51:199–209 (1987).

Houck et al., "Dual Regulation of Vascular Endothelial Growth Factor Bioavailability by Genetic and Proteolytic Mechanisms," *J. Biol. Chem.* 267:26031–26037 (1992).

Jellinek et al., "Inhibition of Receptor Binding by High–Affinity RNA Ligands to Vascular Endothelial Growth Factor," *Biochemistry* 33:10450–10456 (1994).

Kato et al., "Simultaneous Determination of Amfenac Sodium and its Metabolite (7–Benzoyl–2–Oxindole) in Human Plasma by High–Performance Liquid Chromatography," *Journal of Chromatography* 616:67–71 (1993).

Kendall and Thomas, "Inhibition of vascular endothelial cell growth factor activity by an endogenously encoded soluble receptor," *Proc. Natl. Acad. Sci. USA* 90:10705–10709 (1993).

Kim et al., "Inhibition of vascular endothelial growth factor–induced angiogenesis suppreses tumour growth in vivo," *Nature* 362:841–844 (1993).

Kinsella et al., "Protein Kinase C Regulates Endothelial Cell Tube Formation on Basement Membrane Matrix, Matrigel," *Exp. Cell Research* 199:56–62 (1992).

Klagsbrun and Soker, "VEGF/VPF: the angiogenesis factor found?" *Current Biology* 3:699–702 (1993).

Koch et al., "SH2 and SH3 Domains: Elements That Control Interactions of Cytoplasmic Signaling Proteins," *Science* 252:688–674 (1991).

Kohler and Milstein, "Continuous cultures of fused cells secreting antibody of predefined specificity," *Nature* 256:495–497 (1975).

Korc et al., "Overexpression of the Epidermal Growth Factor Receptor in Human Pancreatic Cancer is Associated with Concomitant Increases in the Levels of Epidermal Growth Factor and Transforming Growth Factor Alpha," *J. Clin. Invest.* 90:1352–1360 (1992).

Krueger and Saito, "A human transmembrane protein–tyrosine–phosphatase, PTP, is expressed in brain and has an N–terminal receptor domain homologous to carbonic anyhdyrases," *Proc. Natl. Acad. Sci. USA* 89:7417–7421 (1992).

Kumabe et al., "Amplification of α–platelet–derived growth factor receptor gene lacking an exon coding for a portion of the extracellular region in primary brain tumor of glial origin," *Oncogene* 7:627–633 (1992).

Lee and Donoghue, "Intracellular retention of membrane–anchored v–sis protein abrogates autocrine signal transduction," *Journal of Cell Biology* 118:1057–1070 (1992).

Maass et al., "Viral Resistance to the Thiazolo–Iso–Indolinones, a New Class of Nonnucleoside Inhibitors of Human Immunodeficiency Virus Type 1 Reverse Transcriptase," *Antimicrobial Agents and Chemotherapy* 37(12):2612–2617 (1993).

Macauley et al., "Autocrine function for insulin–like growth factor I in human small cell lung cancer cell lines and fresh tumor cells," *Cancer Research* 50:2511–2517 (1990).

Mariani et al., "Inhibition of angiogenesis by PCE 26806, a potent tyrosine kinase inhibitor," *Experimental Therapeutics—Proceedings of the American Association for Cancer Research* 35:381 at abstract No. 2268 (Mar. 1994).

Moreto et al., "3,3–Bis–(4–Hydroxyphenyl)–7–Methyl–2–Indoline (BHMI), the Active Metabolite of the Laxative Sulisatin," *Arzneimittel–Forschung Drug Research* 29(II):1561–1564 (1979).

Moreto et al., "Study of the Laxative Properties of the Disodium Salt of Sulfuric Diester of 3,3 Bis–(4–Hydroxyphenyl)–7–Methyl–2–Indolinone (Dan–603) in the Rat," *European Journal of Pharmacology* 36:221–226 (1976).

Perkins et al., "The Synthesis of isoHarman," *J. Chem. Soc.* 103:1973–1985 (1913).

Plate et al., "Vascular endothelial growth factor is potential tumor angiogenesis factor in human gilomas in vivo," *Nature* 359:845–848 (1992).

Plowman et al., "Receptor Tyrosine Kinases as Targets for Drug Intervention," *DN&P* 7(6):334–339 (1994).

*Remington's Pharmaceutical Sciences* Gennaro (editor), (1990) (Table of Contents Only).

Saito and Streuli, "Molecular Characterization of Protein Tyrosine Phosphatases," *Cell Growth & Differentiation* 2:59–65 (1991).

Sandberg–Nordqvist et al., "Characterization of Insulin–Like Growth Factor 1 in Human Primary Brain Tumors," *Cancer Research* 53:2475–2478 (1993).

Schlessinger and Ulrich, "Growth Factor Signalling by Receptor Tyrosine Kinases," *Neuron* 9:383–391 (1992).

Schuchter et al., "Successful Treatment of Murine Melanoma with Bryostatin 1," *Cancer Research* 51:682–687 (1991).

*Aust. J. Chem.*, 976 (1952).

*J. Chem. Soc.*, 84:94 (1950).

*J. Chem. Soc.*, 530 (1945).

Crestin, et al., *Synthetic Communications*, 24:2839–2841 (1994).

Quallich, et al., "A General Oxide Synthesis" *Synthesis* pp. 51–53 (1993).

US 6,514,981 B1

METHODS OF MODULATING TYROSINE PROTEIN KINASE FUNCTION WITH INDOLINONE COMPOUNDS

RELATED APPLICATIONS

This application is related to and claims priority to the U.S. Provisional Application Ser. No. 60/080,422, filed on Apr. 2, 1998 by Tang, et al., and entitled "METHODS OF MODULATING TYROSINE PROTEIN KINASE FUNCTION. WITH INDOLINONE COMPOUNDS" (Lyon & Lyon), which is hereby incorporated herein by reference in its entirety, including any drawings.

BACKGROUND OF THE INVENTION

The following description of the background of the invention is provided to aid in understanding the invention, but is not admitted to describe or constitute prior art to the invention.

Cellular signal transduction is a fundamental mechanism whereby extracellular stimuli are relayed to the interior of cells and subsequently regulate diverse cellular at processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins.

Enzymes that mediate phosphorylation of cellular effectors generally fall into two classes. The first class consists of protein kinases which transfer a phosphate moiety from adenosine triphosphate to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases and protein phosphatases are generally divided into two groups—receptor and non-receptor type proteins. Most receptor-type protein tyrosine phosphatases contain two conserved catalytic domains, each of which encompasses a segment of 240 amino acid residues. Saito et al., 1991, *Cell Growth and Diff.* 2:59–65. Receptor protein tyrosine phosphatases can be subclassified further based upon the amino acid sequence diversity of their extracellular domains. Saito et al., supra; Krueger et al., 1992, *Proc. Natl. Acad. Sci. USA* 89:7417–7421.

Protein kinases and protein phosphatases are also typically divided into three classes based upon the amino acids they act upon. Some catalyze the addition or hydrolysis of phosphate on serine or threonine only, some catalyze the addition or hydrolysis of phosphate on tyrosine only, and some catalyze the addition or hydrolysis of phosphate on serine, threonine, and tyrosine.

Tyrosine kinases can regulate the catalytic activity of other protein kinases involved in cell proliferation. Protein kinases with inappropriate activity are also involved in some types of cancer. Abnormally elevated levels of cell proliferation are associated with receptor and non-receptor protein kinases with unregulated activity.

In addition to their role in cellular proliferation, protein kinases are thought to be involved in cellular differentiation processes. Cell differentiation occurs in some cells upon nerve growth factor (NGF) or epidermal growth factor (EGF) stimulation. Cellular differentiation is characterized by rapid membrane ruffling, cell flattening, and increases in cell adhesion. Chao, 1992, *Cell* 68:995–997.

In an effort to discover novel treatments for cancer and other diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases are bis-monocyclic, bicyclic or heterocyclic aryl compounds (PCT WO 92/20642), vinylene-azaindole derivatives (PCT WO 94/14808), 1-cyclopropyl-4-pyridyl-quinolones (U.S. Pat. No. 5,330,992), styryl compounds (by Levitzki, et al., U.S. Pat. No. 5,217,999, and entitled "Styryl Compounds which Inhibit EGF Receptor Protein Tyrosine Kinase, Lyon & Lyon), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660), and benzylphosphonic acid compounds (PCT WO 91/15495).

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Despite the significant progress that has been made in developing compounds for the treatment of cancer, there remains a need in the art to identify the particular structures and substitution patterns that form the compounds capable of modulating the function of particular protein kinases.

SUMMARY OF THE INVENTION

The present invention is directed in part towards indolinone compounds and methods of modulating the function of protein tyrosine kinases with the indolinone compounds. The methods incorporate cells that express protein tyrosine kinases. In addition, the invention describes methods of preventing and treating protein tyrosine kinases-related abnormal conditions in organisms with a compound identified by the methods described herein. Furthermore, the invention pertains to pharmaceutical compositions comprising compounds identified by methods of the invention.

Thus, in a first aspect, the invention provides an indolinone compound having a structure set forth in formula I:

(I)

where (A) Q is an oxindole moiety having the structure set forth in formula II;

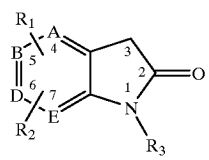

(II)

where
(a) $R_1$, $R_2$, and $R_3$ are independently selected from the group consisting of
  (i) hydrogen;
  (ii) saturated or unsaturated alkyl optionally substituted with halogen, trihalomethyl, carboxylate, nitro, ester, and a five-membered or six-membered aromatic, heteroaromatic, aliphatic, or heteroaliphatic ring moiety, where the ring moiety is optionally substituted with one, two, or three substituents independently selected from the group consisting of alkyl, halogen, trihalomethyl, carboxylate, nitro, and ester moieties;
  (iii) an aromatic or heteroaromatic ring optionally substituted with one, two, or three substituents independently selected from the group consisting of alkyl, alkoxy, halogen, trihalomethyl, carboxylate, nitro, and ester moieties,
  (iv) an aliphatic or heteroaliphatic ring optionally substituted with one, two, or three substituents independently selected from the group consisting of alkyl, alkoxy, halogen, trihalomethyl, carboxylate, nitro, ester, and an aromatic or heteroaromatic ring optionally substituted with one, two, or three substituents independently selected from the group consisting of alkyl, alkoxy, halogen, trihalomethyl, carboxylate, nitro, and ester moieties;
  (v) an amine of formula $—(X_1)_{n1}—NX_2X_3$, where $X_1$ is selected from the group consisting of saturated or unsaturated alkyl, and five-membered or six-membered aromatic, heteroaromatic, or aliphatic ring moieties and where n1 is 0 or 1, and where $X_2$ and $X_3$ are independently selected from the group consisting of hydrogen, saturated or unsaturated alkyl, and five-membered or six-membered aromatic, heteroaromatic, or aliphatic ring moieties;
  (vi) a nitro of formula $—NO_2$;
  (vii) a halogen or trihalomethyl;
  (viii) a ketone of formula $—(X_4)_{n4}—CO—X_5$ where $X_4$ and $X_5$ are independently selected from the group consisting of alkyl optionally substituted with halogen, trihalomethyl, carboxylate, nitro, ester, and five-membered or six-membered aromatic, heteroaromatic, aliphatic, or heteroaliphatic ring moieties, where the ring moieties are optionally substituted with one, two, or three substituents independently selected from the group consisting of alkyl, halogen, trihalomethyl, carboxylate, nitro, and ester moieties and where n4 is 0 or 1;
  (ix) a carboxylic acid of formula $—(X_6)_{n6}—COOH$ or ester of formula $—(X_7)_{n7}—COO—X_8$, where $X_6$, $X_7$, and $X_8$ and are independently selected from the group consisting of alkyl and five-membered or six-membered aromatic, heteroaromatic, aliphatic, or heteroaliphatic ring moieties and where n6 and n7 are independently 0 or 1;
  (x) an alcohol of formula $—(X_9)_{n9}—OH$ or an alkoxyalkyl moiety of formula $—(X_{10})_{n10}—O—X_{11}$, where $X_9$, $X_{10}$, and $X_{11}$ are independently selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n9 and n10 are independently 0 or 1;
  (xi) an amide of formula $—(X_{12})_{n12}—NHCOX_{13}$, or of formula $—(X_{14})_{n14}—CONX_{15}X_{16}$, where $X_{12}$ and $X_{14}$ are each independently selected from the group consisting of alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n12 and n14 are independently 0 or 1, and where $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester;
  (xii) a sulfonamide of formula $—(X_{17})_{n17}—SO_2NX_{18}X_{19}$, where $X_{17}$ is selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$, and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, nitro, and ester and where n17 is 0 or 1;
  (xiii) an aldehyde of formula $—(X_{20})_{n20}—CO—H$ where $X_{20}$ is selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n20 is 0 or 1; and
  (xiv) a sulfone of formula $—(X_{21})_{n21}—SO_2—X_{22}$, where $X_{22}$ is selected from the group consisting of hydroxide, saturated or unsaturated alkyl and five-membered or six-membered aryl or heteroaryl moieties and where $X_{21}$ is selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n21 is 0 or 1, and (xv) a thiol of formula —$(X_{23})_{n23}$—SH or a thioether of formula —$(X_{24})_{n24}$—S—$X_{25}$, where $X_{23}$, $X_{24}$, and $X_{25}$ are independently selected from the group consisting of hydrogen, saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n23 and n24 are independently 0 or 1;

(b) A, B, D, and E are selected from the group consisting of carbon and nitrogen; and (c) Q is bonded with the rest of the molecule through position 3 of the oxindole ring, as set forth in formula II; and (B) T is a ring moiety having the structure set forth in formula III:

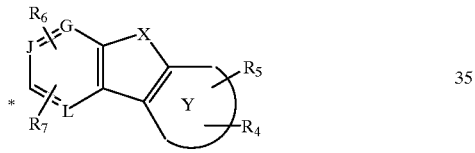

(III)

where (a) $R_4$, $R_5$, $R_6$, and $R_7$ are independently selected from the group consisting of (i) hydrogen;

(ii) saturated or unsaturated alkyl optionally substituted with halogen, trihalomethyl, carboxylate, nitro, ester, and a five-membered or six-membered aromatic, heteroaromatic, aliphatic, or heteroaliphatic ring moiety, where the ring moiety is optionally substituted with one, two, or three substituents independently selected from the group consisting of alkyl, halogen, trihalomethyl, carboxylate, nitro, and ester moieties;

(iii) an aromatic or heteroaromatic ring optionally substituted with one, two, or three substituents independently selected from the group consisting of alkyl, alkoxy, halogen, trihalomethyl, carboxylate, nitro, and ester moieties;

(iv) an aliphatic or heteroaliphatic ring optionally substituted with one, two, or three substituents independently selected from the group consisting of alkyl, alkoxy, halogen, trihalomethyl, carboxylate, nitro, ester, and an aromatic or heteroaromatic ring optionally substituted with one, two, or three substituents independently selected from the group consisting of alkyl, alkoxy, halogen, trihalomethyl, carboxylate, nitro, and ester moieties;

(v) an amine of formula —$(X_1)_{n1}$—$NX_2X_3$, where $X_1$ is selected from the group consisting of saturated or unsaturated alkyl, and five-membered or six-membered aromatic, heteroaromatic, or aliphatic ring moieties and where n1 is 0 or 1, and where $X_2$ and $X_3$ are independently selected from the group consisting of hydrogen, saturated or unsaturated alkyl, and five-membered or six-membered aromatic, heteroaromatic, or aliphatic ring moieties;

(vi) a nitro of formula —$NO_2$;

(vii) a halogen or trihalomethyl;

(viii) a ketone of formula —$(X_4)_{n4}$—CO—$X_5$, where $X_4$ and $X_5$ are independently selected from the group consisting of alkyl optionally substituted with halogen, trihalomethyl, carboxylate, nitro, ester, and five-membered or six-membered aromatic, heteroaromatic, aliphatic, or heteroaliphatic ring moieties, where the ring moieties are optionally substituted with one, two, or three substituents independently selected from the group consisting of alkyl, halogen, trihalomethyl, carboxylate, nitro and ester moieties and where n4 is 0 or 1;

(ix) a carboxylic acid of formula —$(X_6)_{n6}$—COOH or ester of formula —$(X_7)_{n7}$—COO—$X_8$, where $X_6$, $X_7$, and $X_8$ and are independently selected from the group consisting of alkyl and five-membered or six-membered aromatic, heteroaromatic, aliphatic, or heteroaliphatic ring moieties and where n6 and n7 are independently 0 or 1;

(x) an alcohol of formula —$(X_9)_{n9}$—OH or an alkoxyalkyl moiety of formula —$(X_{10})_{n10}$—O—$X_{11}$, where $X_9$, $X_{10}$, and $X_{11}$ are independently selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n9 and n10 are independently 0 or 1;

(xi) an amide of formula —$(X_{12})_{n12}$—$NHCOX_{13}$, or of formula —$(X_{14})_{n14}$—$CONX_{15}X_{16}$, where $X_{12}$ and $X_{14}$ are each independently selected from the group consisting of alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n12 and n14 are independently 0 or 1, and where $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester;

(xii) a sulfonamide of formula —$(X_{17})_{n17}$—$SO_2NX_{18}X_{19}$, where $X_{17}$ is selected from the group consisting of alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, nitro, and ester and where n17 is 0 or 1;

(xiii) an aldehyde of formula —$(X_{20})_{n20}$—CO—H where $X_{20}$ is selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n20 is 0 or 1; and (xiv) a sulfone of formula —$(X_{21})_{n21}$—$SO_2$—$X_{22}$, where $X_{22}$ is selected from the group consisting of hydroxide, saturated or unsaturated alkyl and five-membered or six-membered aryl or heteroaryl moieties and where $X_{21}$ is selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n21 is 0 or 1; and (xv) a thiol of formula —$(X_{23})_{n23}$—SH or a thioether of formula —$(X_{24})_{n24}$—S—$X_{25}$, where $X_{23}$, $X_{24}$, and $X_{25}$, are independently selected from the group consisting of saturated or unsaturated alkyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n23 and n24 are independently 0 or 1;

(b) X is selected from the group consisting of $NX_{26}$, sulfur, SO, $SO_2$, and oxygen, where $X_{26}$ is selected from tho group consisting of
 (i) hydrogen;
 (ii) saturated or unsaturated alkyl optionally substituted with a five-membered or six-membered aryl or heteroaryl ring moiety, where the ring moiety is optionally substituted with one, two, or three substituents independently selected from the group consisting of alkyl, halogen, trihalomethyl, carboxylate, nitro, and ester moieties; p3 (iii) an aryl optionally substituted with one, two, or three substituents independently selected from the group consisting of alkyl, alkoxy, halogen, trihalomethyl, carboxylate, nitro, and ester moieties;
 (iv) a sulfone of formula —$SO_2$—$X_{27}$, where $X_{27}$ is selected from the group consisting of saturated or unsaturated alkyl and five-membered or six-membered aryl or heteroaryl moieties; and
 (v) an acyl of formula —$C(O)X_{28}$, where $X_{28}$ is selected from the group consisting of hydrogen, saturated and unsaturated alkyl, aryl, and a five-membered or six-membered ring moiety;

c) ring Y is selected from the group consisting of five-membered, six-membered, and seven-membered aromatic, heteroaromatic, or non-aromatic rings, where the heteroaromatic ring contains a heteroatom selected from the group consisting of nitrogen, oxygen, and sulfur, and where the non-aromatic ring in combination with $R_4$ optionally forms a carbonyl functionality;

(d) G, J, and L are selected from the group consisting of carbon and nitrogen; and (e) T is bonded with the rest of the molecule through position of the ring marked with an asterisk (*), as get forth in formula III.

The term "indolinone" is used as that term is commonly understood in the art and includes a large subclass of substituted or unsubstituted of compounds that are capable of being synthesized from an aldehyde moiety and a oxindole moiety.

The term "oxindole" refers to an oxindole compound substituted with chemical substituents. Oxindole compounds are of the general structure:

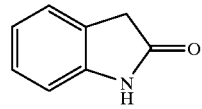

The term "substituted", in reference to the invention, refers to an oxindole compound that is derivatized with any number of chemical substituents.

The term "saturated alkyl" refers to an alkyl moiety that does not contain any alkene or alkyne moieties. The alkyl moiety may be branched or non-branched.

The term "unsaturated alkyl" refers to an alkyl moiety that contains at least one alkene or alkyne moiety. The alkyl moiety may be branched or non-branched.

The term "alkylene" refers to a chain, either strait or branched, $CH_2$ groups where the chain at both ends is attached to another functional group. Thus, for example, methylene refers to —$CH_2$—, ethylene refers to —$CH_2CH_2$—, and propylene refers to —$CH_2CH_2CH_2$—.

The term "aromatic" refers to an aromatic group which has at least one ring having a conjugated pi electron system and includes both carbocyclic aryl (e.g. phenyl) and heterocyclic aryl groups (e.g. pyridine). The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "aliphatic ring" refers to a compound which contains one or more covalently closed ring structures, and that at least one of the atoms forming the backbone is a saturated carbon atom (e.g. cyclohexane). The term "heteroaliphatic ring" refers to a ring system in which at least one of the atoms forming the backbone is a heteroatom (e.g. tetrahydropyran).

The term "amine" refers to a chemical moiety of formula $NR_1R_2$ where $R_1$ and $R_2$ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "halogen" refers to an atom selected from the group consisting of fluorine, chlorine, bromine, and iodine. The term "trihalomethyl" refers to the $—CX_3$ group, where X is a halogen.

The term "ketone" refers to a chemical moiety with formula $—(R)_n—CO—R'$, where R and R' are selected from the group consisting of saturated or unsaturated alkyl and five-membered or six-membered aryl or heteroaryl moieties and where n is 0 or 1.

The term "carboxylic acid" refers to a chemical moiety with formula $—(R)_n—COOH$, where R is selected from the group consisting of saturated or unsaturated alkyl and five-membered or six-membered aryl or heteroaryl moieties and where n is 0 or 1. The term "carboxylate", in the context of this invention, refers to both a carboxylic acid and its anion, $—(R)_n—COO^-$.

The term "ester" refers to a chemical moiety with formula $—(R)_n—COOR'$, where R and R' are independently selected from the group consisting of saturated or unsaturated alkyl and five-membered or six-membered aryl or heteroaryl moieties and where n is 0 or 1.

The term "alcohol" refers to a chemical substituent of formula $—ROH$, where R is selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "alkoxyalkyl moiety" refers to a chemical substituent of formula $—(R)_n—OR'$, where R' is an optionally substituted saturated or unsaturated alkyl moiety or an optionally substituted ring and n is 0 or 1, and where R' is an optionally substituted alkyl or optionally substituted aromatic, heteroaromatic, aliphatic, or heteroaliphatic ring moieties. When n is 0, then the alkoxyalkyl moiety is called an "alkoxy moiety".

The term "amide" refers to a chemical substituent of formula $—NHCOR$, where R is selected from the group consisting of hydrogen, alkyl, hydroxyl, and five-membered or six-membered aryl or heteroaryl ring moieties, where the ring is optionally substituted with one or more substituents independently selected from the group consisting of alkyl, halogen, trihalomethyl, carboxylate, nitro, or ester.

The term "aldehyde" refers to a chemical moiety with formula $—(R)_n—CHO$, a where R is selected from the group consisting of saturated or unsaturated alkyl and five-membered or six-membered aryl or heteroaryl moieties and where n is 0 or 1.

The term "sulfone" refers to a chemical moiety with formula $—SO_2—R$, where R is selected from the group consisting of saturated or unsaturated alkyl and five-membered or six-membered aryl or heteroaryl moieties.

The term "thiol" refers to a chemical moiety with formula $—(R)_n—SH$, where R is selected from the group consisting of optionally substituted alkyl or optionally substituted aromatic, heteroaromatic, aliphatic, or heteroaliphatic ring moieties and where n is 0 or 1. The term "thioether" refers to a chemical moiety of the formula $—(R)_n—SR'$ where both R and R' are selected from the group consisting of optionally substituted alkyl or optionally substituted aromatic, heteroaromatic, aliphatic, or heteroaliphatic ring moieties and where n is 0 or 1.

The term "acyl" refers to chemical moieties of the general formula $—C(O)R$. When R is hydrogen the molecule containing the acyl group is an aldehyde. When R is an alkyl, an aliphatic ring, or an aromatic ring, then the molecule containing the acyl group is a ketone.

In preferred embodiments, the invention relates to an indolinone compound of formula I, where $R_1$ and $R_2$ are selected from the group consisting of (i) hydrogen;

(ii) saturated alkyl optionally substituted with halogen, trihalomethyl, carboxylate, nitro, ester, and an aliphatic or heteroaliphatic ring optionally substituted with halogen, trihalomethyl, carboxylate, nitro, and ester moieties;

(iii) an aromatic ring optionally substituted with one, two, or three substituents independently selected from the group consisting of alkyl, alkoxy, halogen, and nitro moieties;

(iv) an amine of formula $—(X_1)_{n1}—NX_2X_3$, where $X_1$ is optionally substituted saturated alkyl and where n1 is 0 or 1, and where $X_2$, and $X_3$ are independently selected from the group consisting of hydrogen and optionally substituted saturated alkyl;

(v) a nitro of formula $—NO_2$;

(vi) a halogen or trihalomethyl;

(vii) a ketone of formula $—(X_4)_{n4}—CO—X_5$, where $X_4$ and $X_5$ are alkyl and where n4 is 0 or 1;

(viii) a carboxylic acid of formula $—(X_6)_{n6}—COOH$ or ester of formula $—(X_7)_{n7}—COO—X_8$, where $X_6$, $X_7$, and $X_8$ are alkyl and where n6 and n7 are independently 0 or 1;

(ix) an alcohol of formula $—(X_9)_{n9}—OH$ or an alkoxyalkyl moiety of formula $—(X_{10})_{n10}—O—X_{11}$, where $X_9$, $X_{10}$, and $X_{11}$ are saturated alkyl and where n9 and n10 are independently 0 or 1;

(x) an amide of formula $—(X_{12})_{n12}—NHCOX_{13}$, or of formula $—(X_{14})_{n14}—CONX_{15}X_{16}$, where $X_{12}$, $X_{13}$, $X_{14}$, $X_{15}$, and $X_{16}$ are each independently selected from the group consisting of alkyl ad five-membered or six-membered aromatic ring moieties, where the ring is optionally substituted with one or more substituents independently selected from the group consisting of alkyl, halogen, carboxylate, or ester and where n12 and n14 are independently 0 or 1; and (xi) a sulfonamide of formula $—(X_{17})_{n17}—SO_2NX_{18}X_{19}$, where $X_{17}$ is selected from the group consisting of alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, nitro, and ester and where n17 is 0 or 1.

More preferably, $R_1$ and $R_2$ of the indolinone of the invention are selected from the group consisting of (i) hydrogen;

(ii) methyl, ethyl, propyl, and butyl groups optionally substituted with halogen, trihalomethyl, cyano, and nitro moieties;

(iii) phenyl optionally substituted with one, two, or three substituents independently selected from the group consisting of alkyl, alkoxy, halogen, and nitro moieties;

(iv) an amine of formula —$(X_1)_{n1}$—$NX_2X_3$, where $X_2$ and $X_3$ are independently selected from the group consisting of hydrogen and optionally subsituted saturated alkyl, and $X_1$ is optionally substituted saturated alkyl, and where n is 0 or 1;

(v) a nitro of formula —$NO_2$;

(vi) a halogen or trihalomethyl;

(vii) a ketone of formula —CO—$X_4$, where $X_4$ is selected from the group consisting of methyl, ethyl, propyl, and butyl;

(viii) a carboxylic acid of formula —$(X_6)_{n6}$—COOH or ester of formula —$(X_7)_{n7}$—COO—$X_8$, where $X_6$ and $X_7$ are selected from the group consisting of a bond, methylene, ethylene, and propylene, and where $X_8$ is selected from the group consisting of methyl and ethyl, and where n6 and n7 are independently 0 and 1;

(ix) an alkoxy moiety of formula —O—$X_{11}$, where $X_{11}$ is selected from the group consisting of methyl and ethyl;

(x) an amide of formula —$NHCOX_{13}$, where $X_{13}$ is phenyl optionally substituted with one or more substituents independently selected from the group consisting of alkyl, halogen, carboxylate, or ester; and (xi) a sulfonamide of formula —$SO_2NX_{18}X_{19}$, where $X_{18}$ and $X_{19}$ are independently selected from the group consisting of hydrogen, methyl, ethyl, phenyl optionally substituted with one or more substituents independently selected from the group consisting of alkyl, halogen, and trihalomethyl, and where $X_{18}$ and $X_{19}$ taken together form a six-membered heteroaliphatic ring moiety.

In some embodiments, E in formula II is nitrogen.

Most preferably, the indolinone compounds of the invention are those whose structure is set forth in formula I, where Q is selected from the group consisting of type Q oxindoles. By "type Q oxindoles" is meant oxindole compounds which are selected from the list of oxindoles numbered O-1 through O-60, and are depicted as follows.

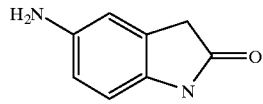
(O-1)

-continued

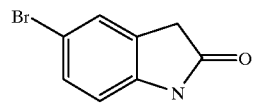
(O-2)

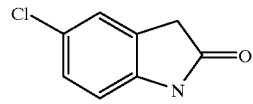
(O-3)

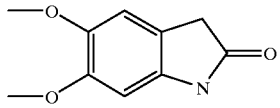
(O-4)

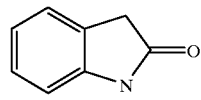
(O-5)

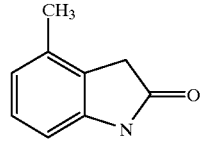
(O-6)

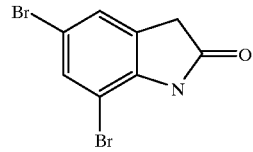
(O-7)

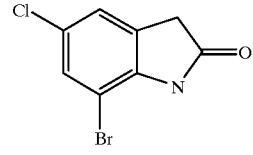
(O-8)

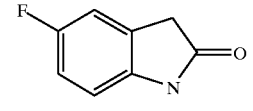
(O-9)

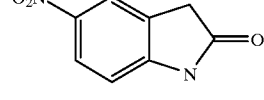
(O-10)

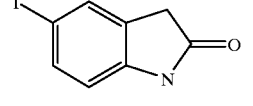
(O-11)

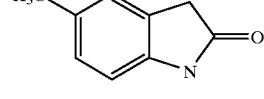
(O-12)

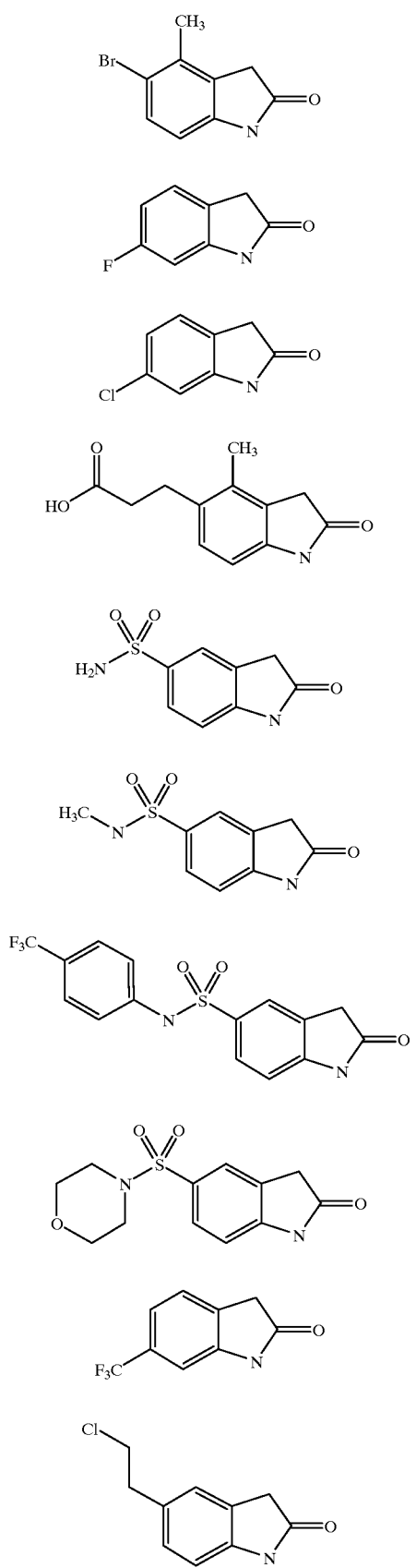
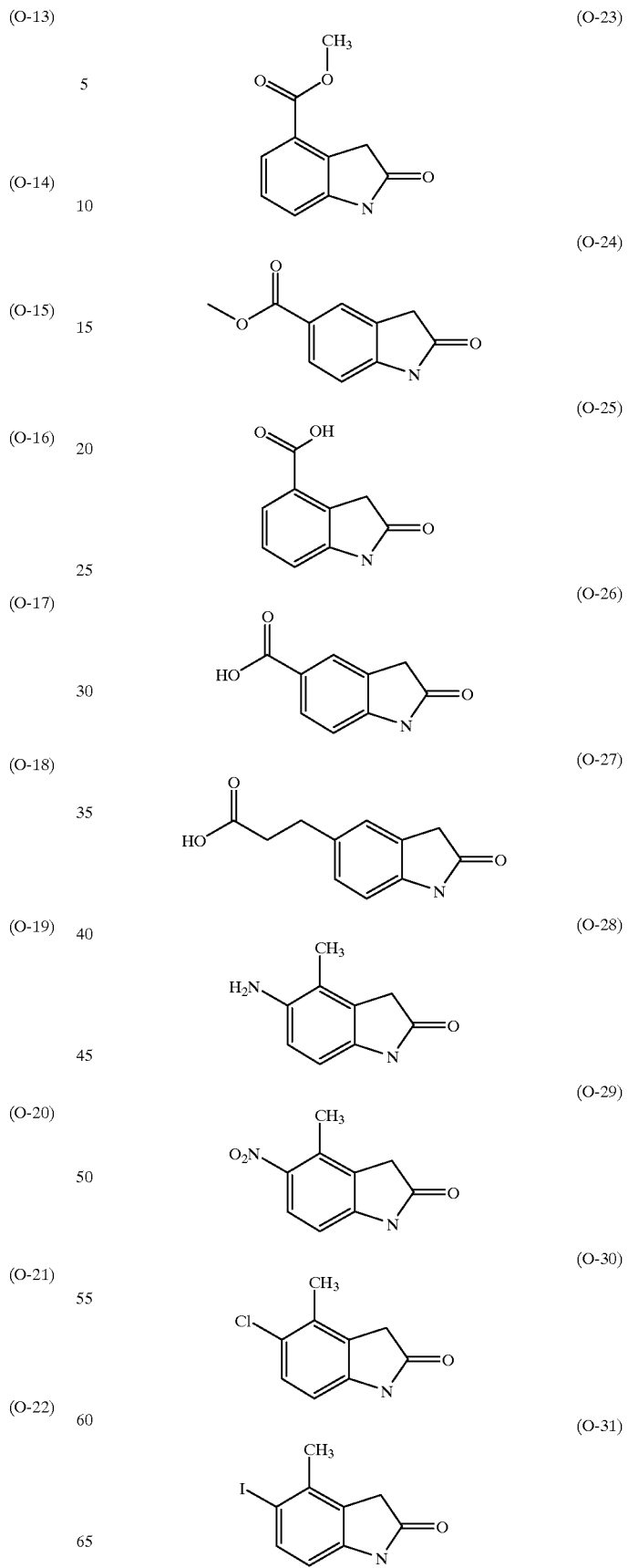

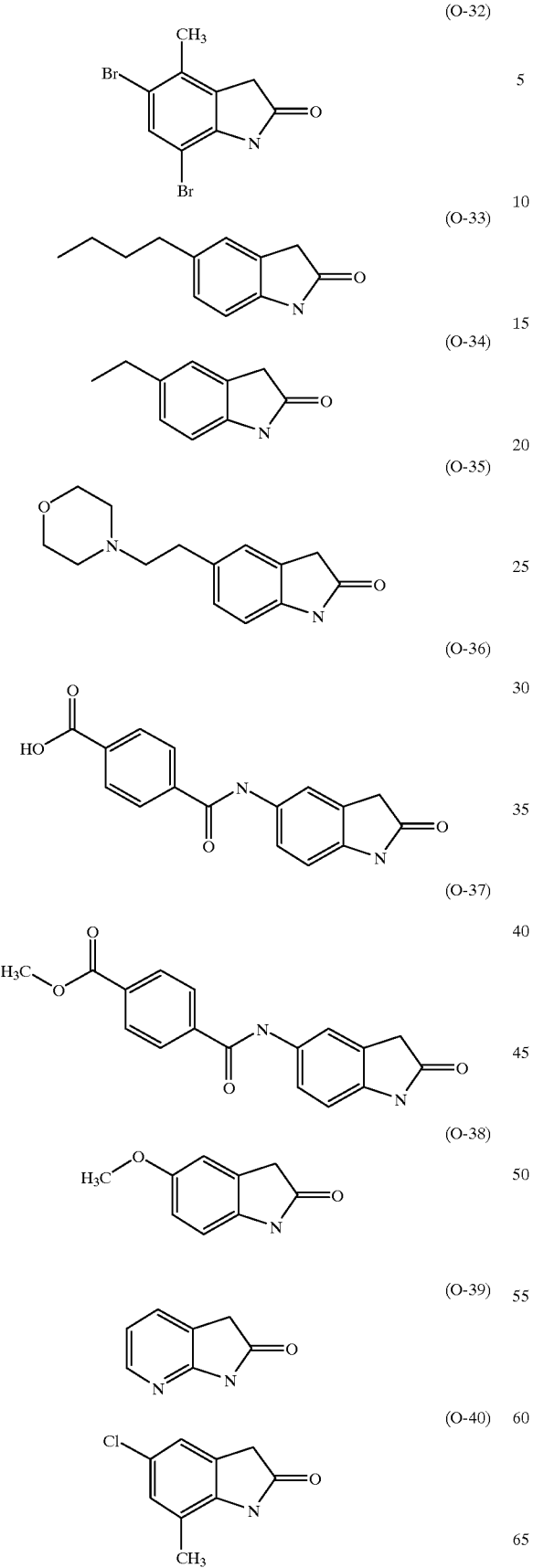
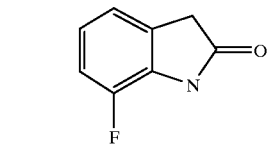(O-41)
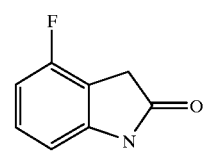(O-42)
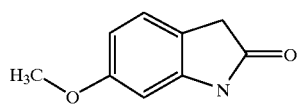(O-43)
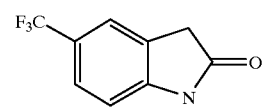(O-44)
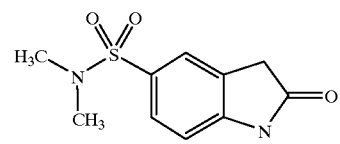(O-45)
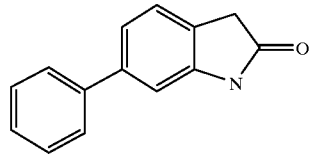(O-46)
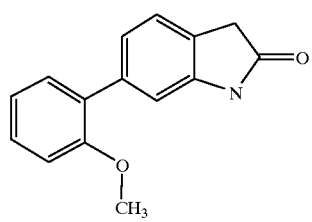(O-47)
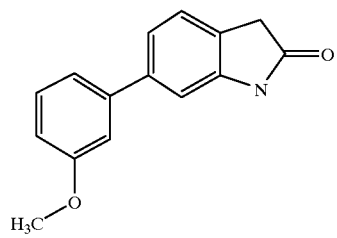(O-48)

(O-49) 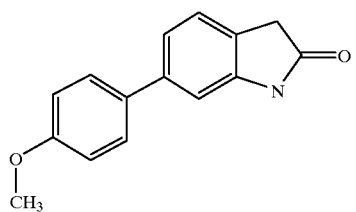

(O-50) 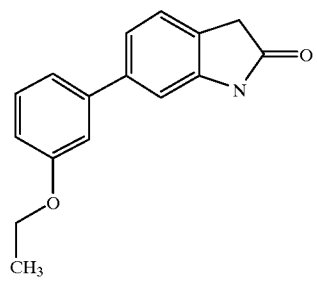

(O-51) 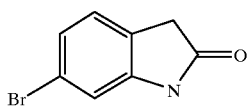

(O-52) 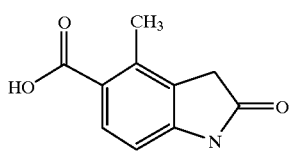

(O-53) 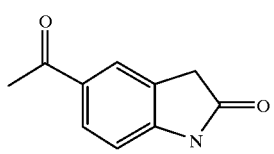

(O-54) 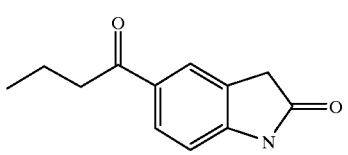

(O-55) 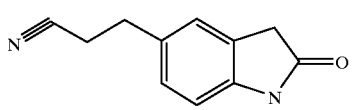

(O-56) 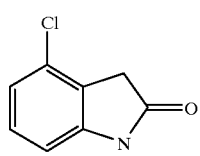

(O-57) 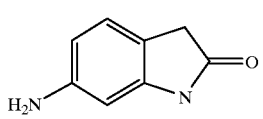

(O-58) 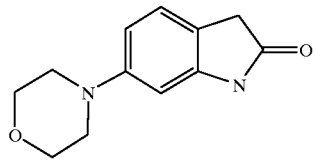

(O-59) 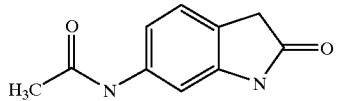

(O-60) 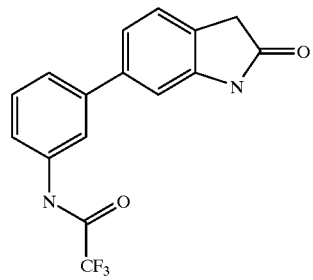

In certain other preferred embodiments, the indolinone of the invention has a structure as set forth in formula I, where $R_4$ and $R_5$ are independently selected from the group consisting of (i) hydrogen;

(ii) methyl, ethyl, propyl, and butyl groups optionally substituted with halogen, trihalomethyl, cyano, and nitro moieties;

(iii) an amine of formula $—(X_1)_{n1}—NX_2X_3$, where $X_2$ and $X_3$ are independently selected from the group consisting of hydrogen and substituted saturated alkyl, and $X_1$ is substituted saturated alkyl, and where n1 is 0 or 1, or where $X_2$ and $X_3$ taken together form a five-membered or a six-membered aliphatic or heteroaliphatic ring, optionally substituted at a ring carbon atom or heteroatom with a substituent selected from the group consisting of methyl, ethyl, propyl, phenyl, and alkoxyphenyl;

(iv) a nitro of formula $—NO_2$;

(v) a halogen or trihalomethyl;

(vi) a ketone of formula $—CO—X_4$, where $X_4$ is selected from the group consisting of methyl, ethyl, propyl, n-butyl, and t-butyl;

(vii) a carboxylic acid of formula $—(X_6)_{n6}—COOH$ or ester of formula $—(X_7)_{n7}—COO—X_8$, where $X_6$ and $X_7$ are selected from the group consisting of a bond, methylene, ethylene, and propylene, and where $X_8$ is selected from the group consisting of methyl and ethyl, and where n6 and n7 are independently 0 or 1;

(viii) an amide of formula $—NHCOX_{13}$, or of formula $—CONX_{15}X_{16}$, where $X_{13}$, $X_{15}$, and $X_{16}$ are each independently selected from the group consisting of hydrogen, methyl, ethyl, propyl, and phenyl;

(ix) a sulfonamide of formula $—SO_2NX_{18}X_{19}$, where $X_{18}$ and $X_{19}$ are independently selected from the group consisting of hydrogen, methyl, and ethyl;

(x) an alcohol of formula $—(X_9)_{n9}—OH$ or an alkoxyalkyl moiety of formula $—(X_{10})_{n10}—O—X_{11}$, where $X_9$, and $X_{10}$ are independently selected form the group consisting of methylene, ethylene, and propylene, and where $X_{11}$ is independently selected from the group consisting of methyl, ethyl, and propyl, and where n9 and n10 are independently 0 or 1;

(xi) a sulfone of formula —$(X_{21})_{n21}$—$SO_2$—$X_{22}$, where $X_{22}$ is selected from the group consisting of hydroxide, saturated or unsaturated alkyl, and five-membered or six-membered aryl or heteroaryl moieties, and where $X_{21}$ is saturated alkyl, and where n21 is 0 or 1; and (x) a thioether of formula —$(X_{24})_{n24}$—S—$X_{25}$, where $X_{24}$ is independently selected from the group consisting of methylene, ethylene, and propylene, and where $X_{25}$ is independently selected from the group consisting of methyl, ethyl, propyl, and phenyl, and where n24 is 0 or 1.

More preferably, $R_4$ and $R_5$ are each independently selected from the group consisting of (i) hydrogen;
(ii) methyl and ethyl;
(iii) an amine of formula —$(X_1)_{n1}$—$NX_2X_3$, where $X_2$ and $X_3$ are independently selected from the group consisting of hydrogen methyl and ethyl, and $X_1$ is methylene or ethylene, and where n1 is 0 or 1, or where $X_2$ and $X_3$ taken together form a substituted ring selected from the group consisting of

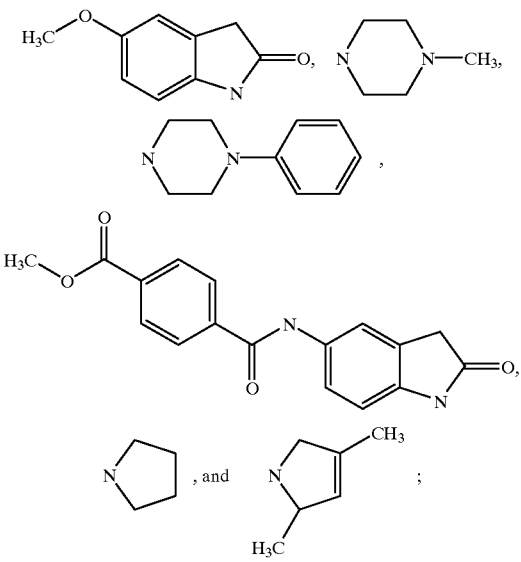

(iv) a nitro of formula —$NO_2$;
(v) a halogen;
(vi) a ketone of formula —CO—$X_4$, where $X_4$ is selected from the group consisting of methyl and t-butyl;
(vii) a carboxylic acid of formula —$(X_6)_{n6}$—COOH or ester of formula —$(X_7)_{n7}$—COO—$X_8$, where $X_6$ and $X_7$ are selected from the group consisting of a bond, methylene, ethylene, and propylene, and where $X_8$ is selected from the group consisting of methyl and ethyl, and where n6 and n7 are independently 0 or 1;
(viii) an amide of formula —$NHCOX_{13}$, or of formula —$CONX_{15}X_{16}$, where $X_{13}$, $X_{15}$, and $X_{16}$ are each independently selected from the group consisting of hydrogen, methyl, and phenyl;
(ix) a sulfonamide of formula —$SO_2NX_{18}X_{19}$, where $X_{18}$ and $X_{19}$ are independently selected from the group consisting of hydrogen, methyl, and ethyl;
(x) an alcohol of formula —$(X_9)_{n9}$—OH or an alkoxyalkyl moiety of formula —$(X_{10})_{n10}$—O—$X_{11}$, where $X_9$, and $X_{10}$ are independently selected form the group consisting of methylene, ethylene, and propylene, and where $X_{11}$ is independently selected from the group consisting of methyl, ethyl, and propyl, and where n9 and n10 are independently 0 or 1;
(xi) a sulfone of formula —$SO_2$—$X_{22}$, where $X_{22}$ is hydroxide; and
(xi) a thioether of formula —S—$X_{25}$, where $X_{25}$ is phenyl.

Preferably, $R_6$ and $R_7$ groups of the indolinone compounds of the invention are independently selected from the group consisting of (i) hydrogen;
(ii) methyl, ethyl, propyl, and butyl groups optionally substituted with halogen, trihalomethyl, cyano, and nitro moieties;
(iii) an amine of formula —$(X_1)_{n1}$—$NX_2X_3$, where $X_2$ and $X_3$ are independently selected from the group consisting of hydrogen and substituted saturated alkyl, and $X_1$ is an optionally substituted saturated alkylene, and where n1 is 0 or 1;
(iv) a halogen or trihalomethyl;
(v) an alcohol of formula —$(X_9)_{n9}$—OH or an alkoxyalkyl moiety of formula —$(X_{10})_{n10}$—O—$X_{11}$, where $X_9$ and $X_{10}$ are independently selected form the group consisting of methylene, ethylene, and propylene, and where $X_{11}$ is independently selected form the group consisting of methyl, ethyl, and propyl, and where n9 and n10 are independently 0 or 1.

More preferably, $R_6$ and $R_7$ are independently selected from the group consisting of (i) hydrogen;
(ii) methyl and ethyl,
(iii) an amine of formula —$(X_1)_{n1}$—$NX_2X_3$, where $X_2$ and $X_3$ are independently selected from the group consisting of hydrogen, methyl, and ethyl, and $X_1$ is selected from the group consisting of methylene and ethylene, and where n1 is 0 or 1;
(iv) a halogen;
(v) a hydroxy —OH or an alkoxy moiety of formula —O—$X_{11}$, where $X_{11}$ is independently selected form the group consisting of methyl, ethyl, and propyl.

Preferably, the Y ring of the indolinone compound of the invention is a six-membered aromatic or heteroaromatic ring. If Y is an aromatic ring, then the moiety set forth in formula III would take the form set forth in formula V

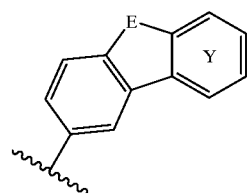

(V)

with the rings optionally substituted as described herein and E having the limitations set forth herein. If Y is a heteroaromatic ring, then at least one of carbon atoms of the Y ring of the structure set forth in formula V is a heteroatom (e.g. nitrogen).

In some other preferred embodiments, the Y ring of the indolinone compounds is a six-membered aliphatic or heteroaliphatic ring. Then, the Y ring in the structure set forth in formula V takes the form of, for example, optionally substituted

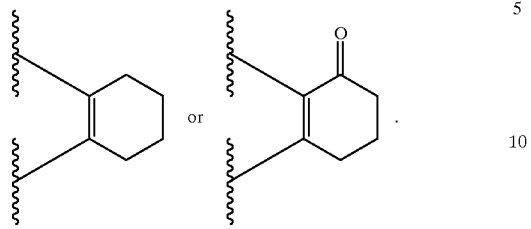

In other preferred embodiments, G, J, and L are independently nitrogen. X may also preferably be oxygen, nitrogen, optionally substituted with an alkyl, or be selected from the group consisting of sulfur, SO, and $SO_2$.

In preferred embodiments, the precursor to the T moiety of the indolinone compound of the invention set forth in formula I is selected from the group consisting of type T aldehydes. By "type T aldehyde" is meant aldehyde compounds which are selected from the list of aldehydes numbered A-1 through A-95, and are depicted as follows.

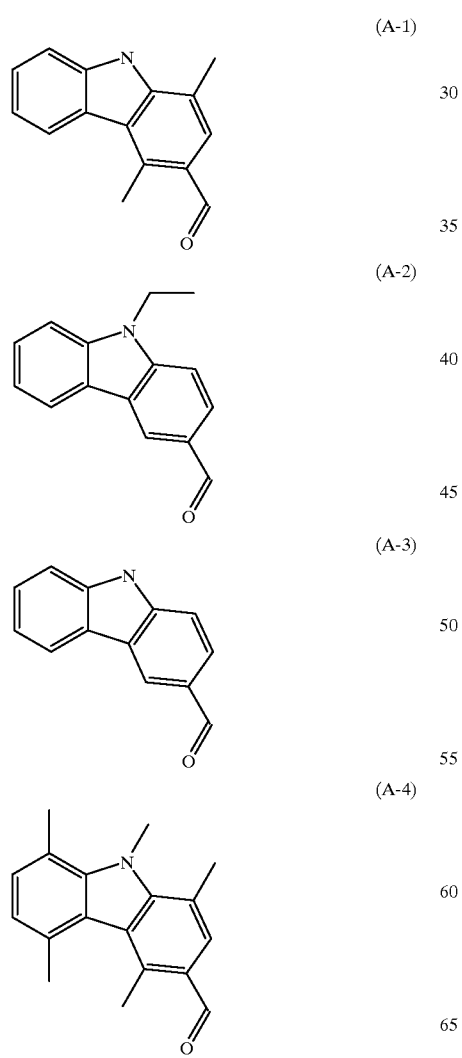

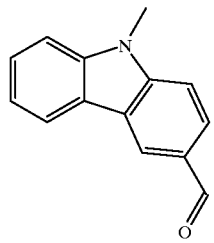

(A-5)

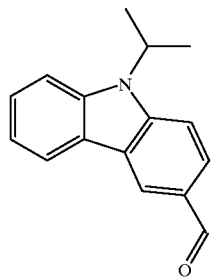

(A-6)

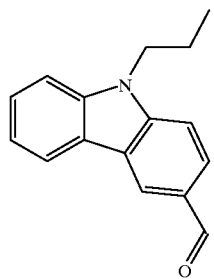

(A-7)

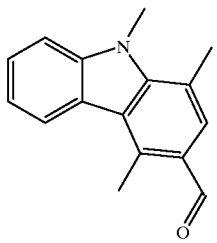

(A-8)

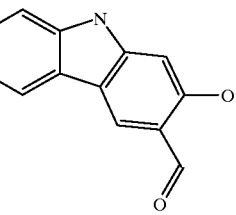

(A-9)

(A-10)

-continued (A-11) (A-12) (A-13) (A-14) (A-15) (A-16) (A-17) (A-18) (A-19) (A-20) (A-21) (A-22)

(A-23) 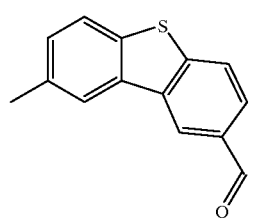
(A-24) 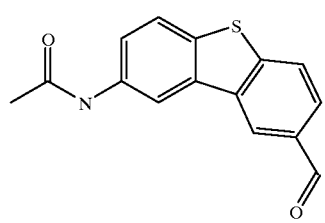
(A-25) 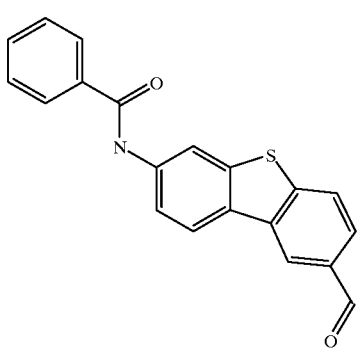
(A-26) 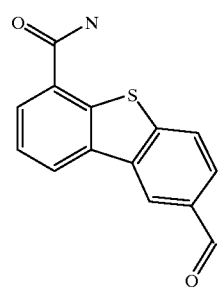
(A-27) 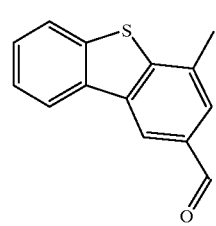
(A-28) 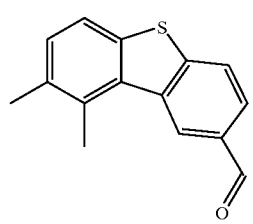
(A-29) 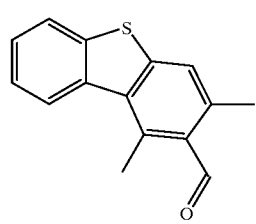
(A-30) 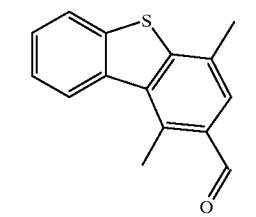
(A-31) 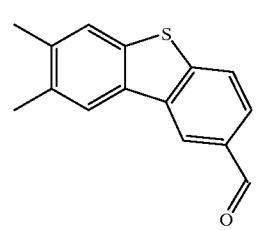
(A-32) 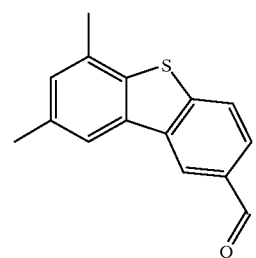
(A-33) 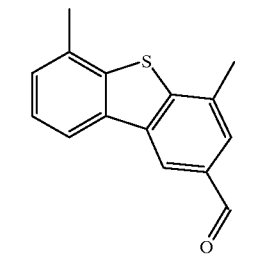
(A-34) 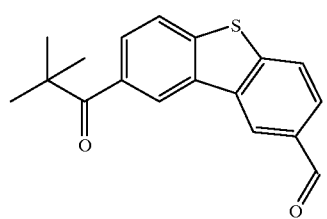

(A-35)
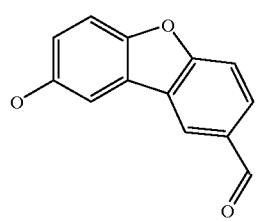
(A-36)
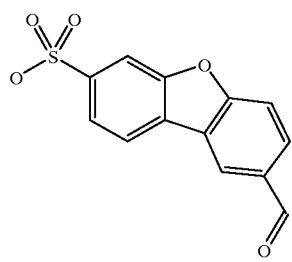
(A-37)
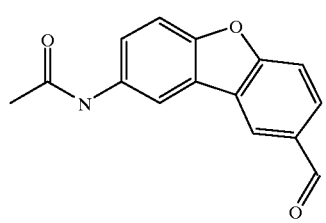
(A-38)
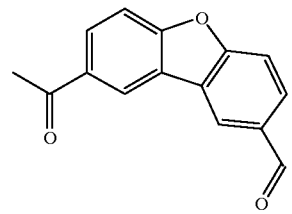
(A-39)
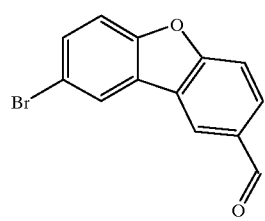
(A-40)
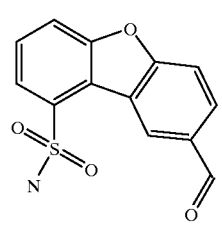
(A-41)
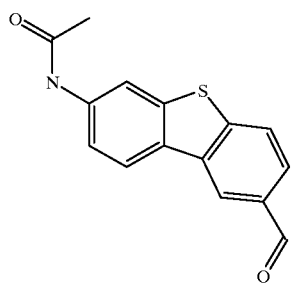
(A-42)
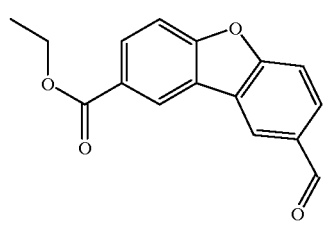
(A-43)
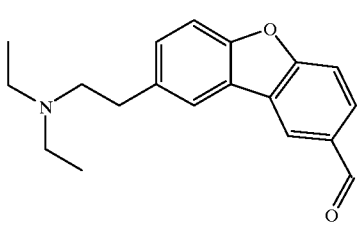
(A-44)
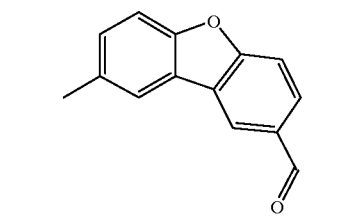
(A-45)
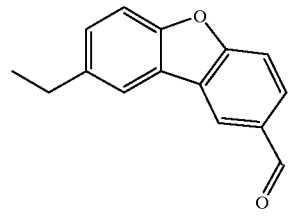
(A-46)
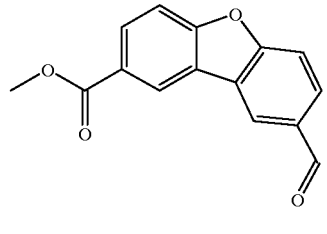

(A-47) 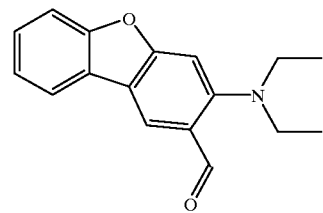
(A-48) 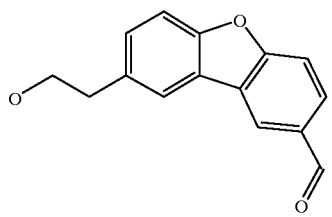
(A-49) 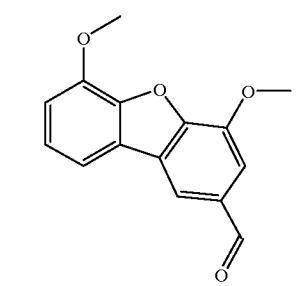
(A-50) 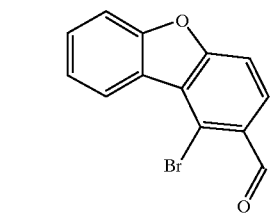
(A-51) 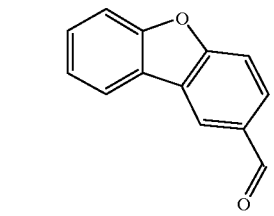
(A-52) 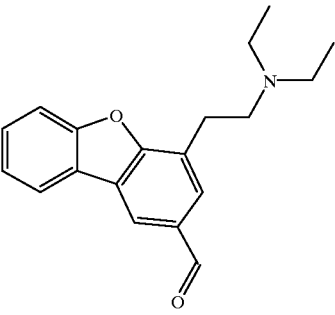
(A-53) 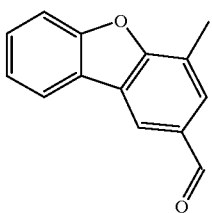
(A-54) 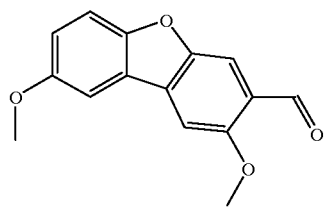
(A-55) 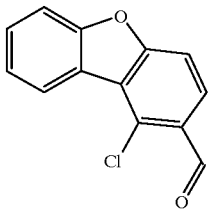
(A-56) 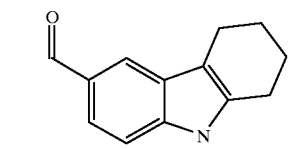
(A-57) 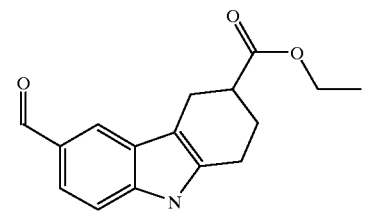
(A-58) 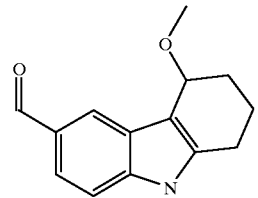
(A-59) 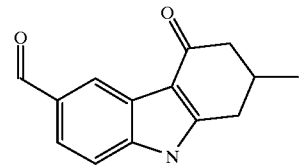

(A-60) 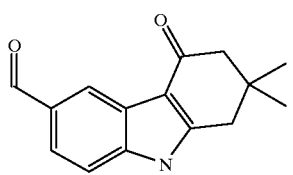
(A-61) 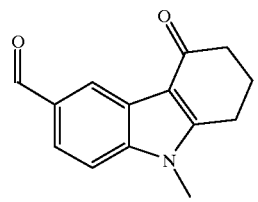
(A-62) 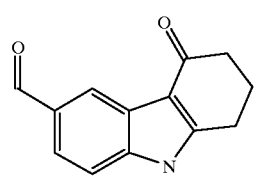
(A-63) 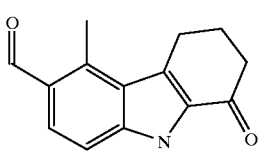
(A-64) 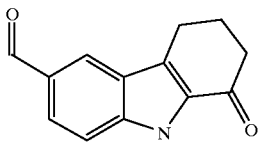
(A-65) 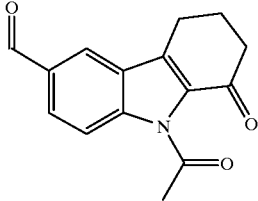
(A-66) 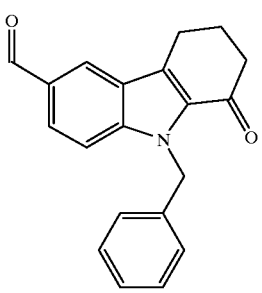
(A-67) 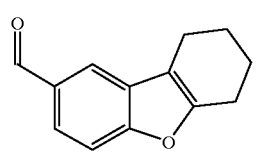
(A-68) 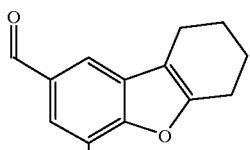
(A-69) 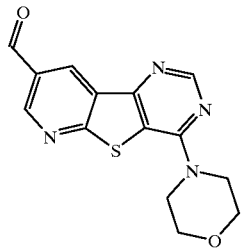
(A-70) 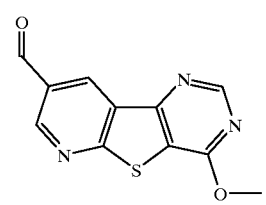
(A-71) 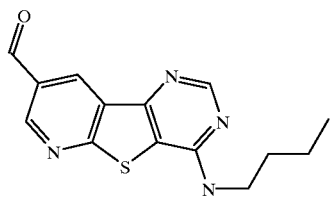
(A-72) 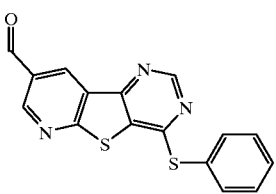
(A-73) 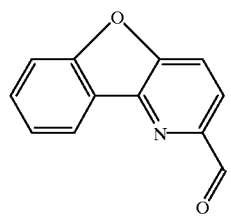
(A-74) 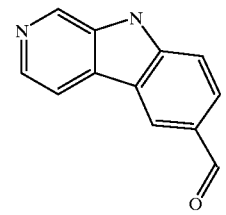

(A-75)
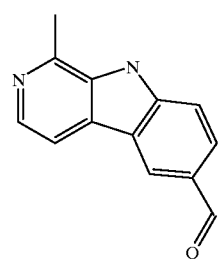
(A-76)
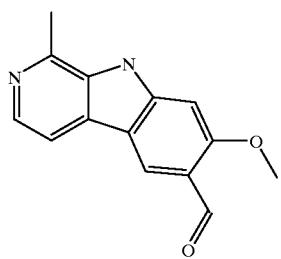
(A-77)
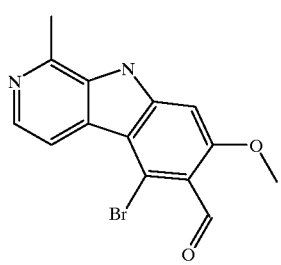
(A-78)
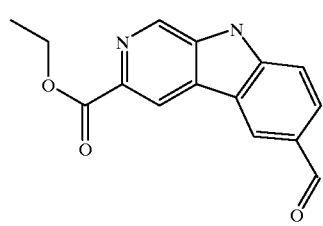
(A-79)
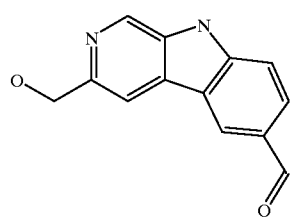
(A-80)
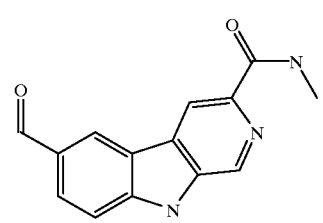
(A-81)
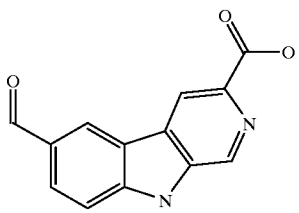
(A-82)
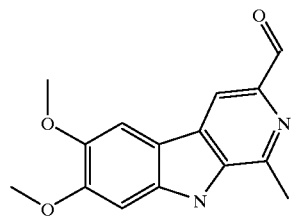
(A-83)
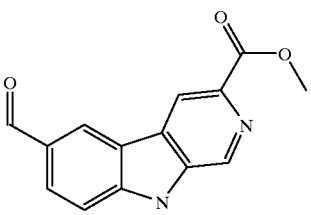
(A-84)
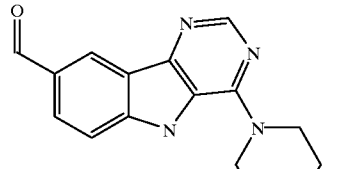
(A-85)
(A-86)
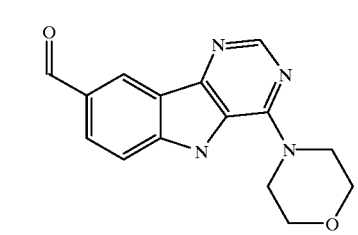

(A-87) 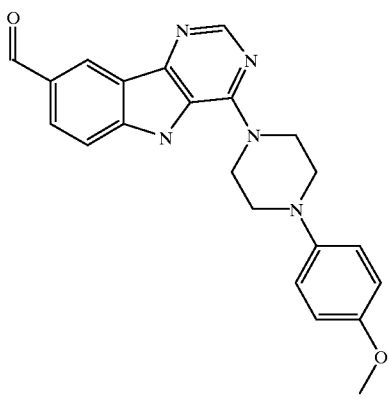

(A-88) 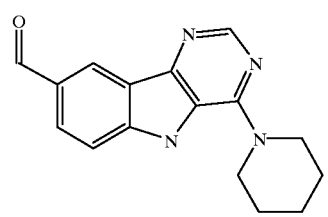

(A-89) 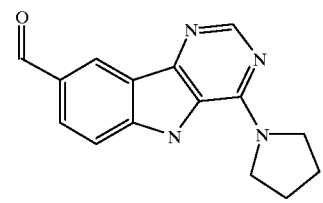

(A-90) 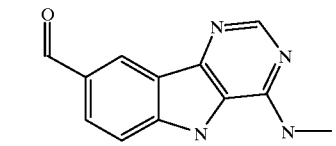

(A-91) 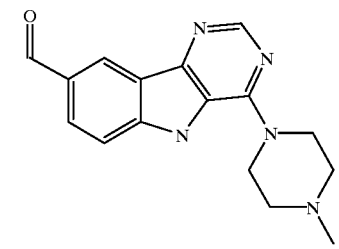

(A-92) 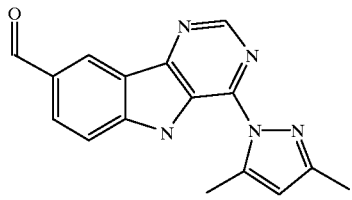

(A-93) 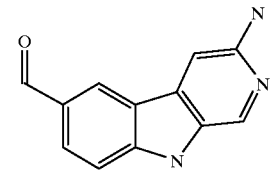

(A-94) 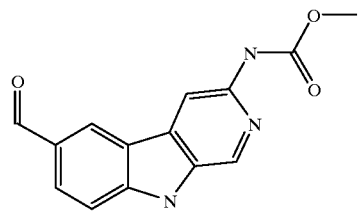

(A-95) 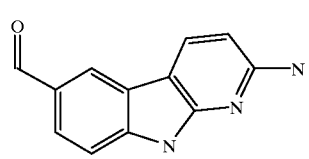

In another aspect, the invention relates to a combinatorial library of at least 10 indolinone compounds that can be formed by reacting oxindoles with aldehydes. In preferred embodiments, the oxindoles are those that have a structure set forth in formula II as defined herein or any of the subgroups thereof set forth herein. The oxindoles ale preferably selected from the group consisting of type Q oxindoles.

The aldehydes of the combinatorial library of the invention preferably have a structure set forth in formula IV:

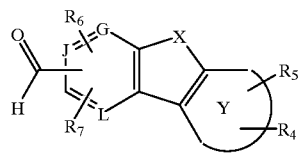

(IV)

with $R_4$, $R_5$, $R_6$, $R_7$, G, J, L, X, and Y are as defined herein for the compound of formula III, or any of the subgroups thereof set forth herein. Preferably, the aldehydes are selected from the group consisting of type T aldehydes.

In a further aspect, the invention features a method for synthesizing an indolinone compound comprising the steps of:

(a) reacting a first reactant with a second reactant in a solvent and in the presence of a base at elevated temperatures, where the first reactant is an oxindole, and where the second reactant is an aldehyde;

(b) purifying the indolinone compound.

The first reactant is preferably selected from the group consisting of type Q oxindoles and the second reactant is preferably selected from the group consisting of type T aldehydes. The base is preferably a nitrogen base, and most preferably, the base is piperidine.

"Nitrogen bases" are commonly used in the art and are selected from acyclic and cyclic amines. Examples of nitrogen bases include, but are not limited to, ammonia, methyl amine, trimethylamine, aniline, and piperidine. Those skilled in the art know which nitrogen base would match the requirements of the reaction conditions.

The solvent of the reaction is preferably an alcohol, and most preferably, the solvent is ethanol.

The synthetic method of the invention calls for the reaction to take place at elevated temperatures. The term "elevated temperatures" refers to temperatures that are greater than room temperature. More preferably, the elevated temperature is about 90° C. By "about 90° C." it is meant that the temperature range is preferably 90±10° C., more preferably 90±5° C., and most preferably 90±2° C.

In another aspect, the invention features a pharmaceutical composition comprising (i) a physiologically acceptable carrier, diluent, or excipient; and (ii) an indolinone compound as described herein, or a salt thereof.

The term "pharmaceutical composition" refers to a mixture of an indolinone compound of the invention with other chemical components, such as diluents, excipients, or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "physiologically acceptable" defines a carrier or diluent that does not abrogate the biological activity and properties of the compound.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The invention also features a method of modulating the function of a protein tyrosine kinase with an indolinone compound, comprising the step of contacting cells expressing the protein tyrosine kinase with the compound.

The term "function" refers to the cellular role of a protein tyrosine kinase. The protein tyrosine kinase family includes members that regulate many steps in signaling cascades, including cascades controlling cell growth, migration, differentiation, gene expression, muscle contraction, glucose metabolism, cellular protein synthesis, and regulation of the cell cycle.

The term "catalytic activity", in the context of the invention, defines the rate at which a protein kinase phosphorylates a substrate. Catalytic activity can be measured, for example, by determining the amount of a substrate converted to a product as a function of time. Phosphorylation of a substrate occurs at the active-site of a protein kinase. The active-site is normally a cavity in which the substrate binds to the protein kinase and is phosphorylated.

The term "substrate" as used herein refers to a molecule phosphorylated by a protein tyrosine kinase. The substrate is preferably a peptide and more preferably a protein.

The term "activates" refers to increasing the cellular function of a protein kinase. The protein kinase unction is preferably the interaction with a natural binding partner and most preferably catalytic activity.

The term "inhibit" refers to decreasing the cellular function of a protein kinase. The protein kinase function is preferably the interaction with a natural binding partner and most preferably catalytic activity.

The term "modulates" refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "complex" refers to an assembly of at least two molecules bound to one another. Signal transduction complexes often contain at least two protein molecules bound to one another.

The term "natural binding partner" refers to polypeptides that bind to a protein kinase in cells. Natural binding partners can play a role in propagating a signal in a protein kinase signal transduction process. A change in the interaction between a protein kinase and a natural binding partner can manifest itself as an increased or decreased probability that the interaction forms, or an increased or decreased concentration of the protein kinase/natural binding partner complex.

A protein kinase natural binding partner can bind to a protein kinase's intracellular region with high affinity. High affinity represents an equilibrium binding constant on the order of $10^{-6}$ M or less. In addition, a natural binding partner can also transiently interact with a protein kinase intracellular region and chemically modify it. Protein kinase natural binding partners are chosen from a group that includes, but is not limited to, SRC homology 2 (SH2) or 3 (SH3) domains, other phosphoryl tyrosine binding (PTB) domains, guanine nucleotide exchange factors, protein phosphatases, and other protein kinases. Methods of determining changes in interactions between protein kinases and their natural binding partners are readily available in the art.

The term "contacting" as used herein refers to mixing a solution comprising an indolinone compound of the invention with a liquid medium bathing the cells of the methods. The solution comprising the compound may also comprise another component, such as dimethylsulfoxide (DMSO), which facilitates the uptake of the indolinone compound or compounds into the cells of the methods. The solution comprising the indolinone compound may be added to the medium bathing the cells by utilizing a delivery apparatus, such as a pipet-based device or syringe-based device.

The indolinone compounds of the invention preferably modulate the activity of the protein tyrosine kinase in vitro. These compounds preferably show positive results in one or more in vitro assays for an activity corresponding to treatment of the disease or disorder in question (such as the assays described in the Examples below). The protein tyrosine kinase which is modulated by the indolinone compounds of the invention is preferably HER2. The procedures for and the results of such modulation are described in the Examples below.

The invention also features a method of identifying indolinone compounds that modulate the function of protein tyrosine kinase, comprising the following steps: (a) contacting cells expressing the protein tyrosine kinase with the compound; and (b) monitoring an effect upon the cells. The effect upon the cells is preferably a change or an absence of a change in cell phenotype, more preferably it is a change or an absence of a change in cell proliferation, even more preferably it is a change or absence of a change in the catalytic activity of the protein tyrosine kinase, and most preferably it is a change or absence of a change in the interaction between the protein tyrosine kinase with a natural binding partner, as described herein.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "effect" describes a change or an absence of a change in cell phenotype or cell proliferation. "Effect" can also describe a change or an absence of a change in the catalytic activity of the protein kinase. "Effect" can also describe a change or an absence of a change in an interaction between the protein kinase and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

In a preferred embodiment, the invention features a method for identifying the indolinones of the invention, comprising the following steps: (a) lysing the cells to render a lysate comprising protein tyrosine kinase; (b) adsorbing the protein tyrosine kinase to an antibody; (c) incubating the adsorbed protein tyrosine kinase with a substrate or substrates, and (d) adsorbing the substrate or substrates to a solid support or antibody; where the step of monitoring the effect on the cells comprises measuring the phosphate concentration of the substrate or substrates.

The term "antibody" refers to an antibody (e.g., a monoclonal or polyclonal antibody), or antibody fragment, having specific binding affinity to protein tyrosine kinase or its fragment.

By "specific binding affinity" is meant that the antibody binds to target (protein tyrosine kinase) polypeptides with greater affinity than it binds to other polypeptides under specified conditions. Antibodies having specific binding affinity to a protein tyrosine kinase may be used in methods for detecting the presence and/or amount of a protein tyrosine kinase in a sample by contacting the sample with the antibody under conditions such that an immunocomplex forms and detecting the presence and/or amount of the antibody conjugated to the protein tyrosine kinase. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In yet another aspect, the invention features a method for treating a disease related to unregulated tyrosine kinase signal transduction, the method comprising the step of administering to a subject in need thereof a therapeutically effective amount of an indolinone compound as described herein.

The invention also features a method of regulating tyrosine kinase signal transduction comprising administering to a subject a therapeutically effective amount of an indolinone compound as described herein.

Furthermore, the invention features a method of preventing or treating an abnormal condition in an organism, where the abnormal condition is associated with an aberration in a signal transduction pathway characterized by an interaction between a protein kinase and a natural binding partner, where the method comprises the following steps: (a) administering an indolinone compound as described herein; and (b) promoting or disrupting the abnormal interaction. The organism is preferably a mammal and the abnormal condition is preferably cancer. The abnormal condition may also preferably be selected from the group consisting of hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders.

The term "aberration", in conjunction with a signal transduction process, refers to a protein kinase that is over- or under-expressed in an organism, mutated such that its catalytic activity is lower or higher than wild-type protein kinase activity, mutated such that it can no longer interact with a natural binding partner, is no longer modified by another protein kinase or protein phosphatase, or no longer interacts with a natural binding partner.

The term "promoting or disrupting the abnormal interaction" refers to a method that can be accomplished by administering a compound of the invention to cells or tissues in an organism. A compound can promote an interaction between a protein kinase and natural binding partners by forming favorable interactions with multiple atoms at the complex interface. Alternatively, a compound can inhibit an interaction between a protein kinase and natural binding partners by compromising favorable interactions formed between atoms at the complex interface. The present invention also features novel oxindole compounds. In one aspect, the invention features an oxindole compound of formula V

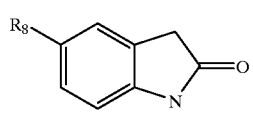

(V)

where $R_8$ is selected from the group consisting of
(i) saturated alkyl, optionally substituted with a substituent selected from the group consisting of alkoxy, trihalomethyl, nitro, and cyano moieties, provided that the alkyl is not methyl;
(ii) an amine of formula —$(X_1)_{n1}$—$NX_2X_3$, where $X_1$ is selected from the group consisting of hydrogen, saturated or unsaturated alkyl, and five-membered or six-membered aromatic, heteroaromatic, or aliphatic ring moieties and where n1 is 0 or 1, and where $X_2$ and $X_3$ taken together form a 5-membered or 6-membered heteroaliphatic ring;
(iii) an iodine;
(iv) a ketone of formula —$(X_4)_{n4}$—CO—$X_5$, where $X_4$ and $X_5$ are independently alkyl and where n4 is 0 or 1;
(v) a carboxylic acid of formula —$(X_6)_{n6}$—COOH or ester of formula —$(X_7)_{n7}$—COO—$X_8$ where $X_6$, $X_7$, and $X_8$ and are independently selected from the group consisting of alkyl and five-membered or six-membered aromatic, heteroaromatic, aliphatic, or heteroaliphatic ring moieties and where n6 and n7 are independently 0 or 1;
(vi) an amide of formula —$(X_{12})_{n12}$—$NHCOX_{13}$, or of formula —$(X_{14})_{n14}$—$CONX_{15}X_{16}$, where $X_{12}$ and $X_{14}$ are each independently selected from the group consisting of alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n12 and n14 are independently 0 or 1, and where $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester; and
(vii) a sulfonamide of formula —$(X_{17})_{n17}$—$SO_2NX_{18}X_{19}$, where $X_{17}$ is selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$, and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, nitro, and ester and where n17 is 0 or 1.

The oxindole compound of formula V is preferably selected from the group consisting of

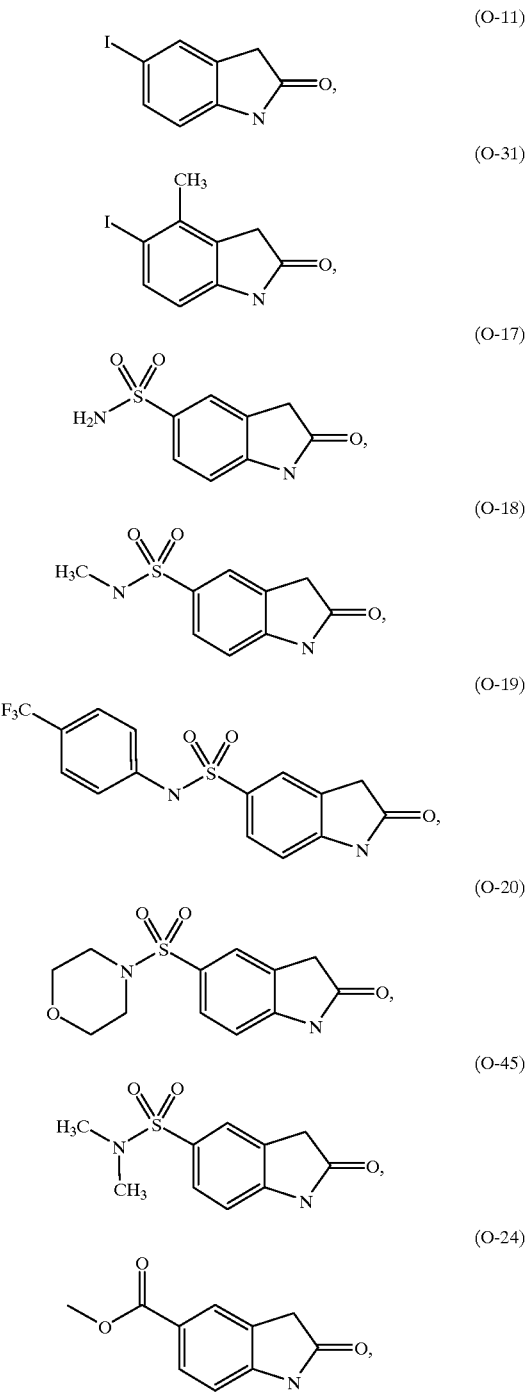

(O-36)
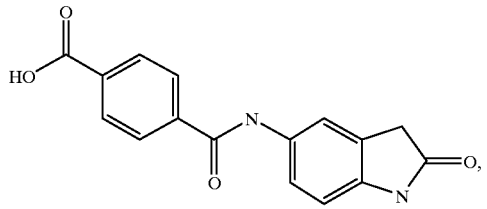

(O-37)
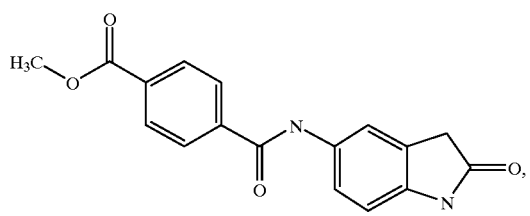

(O-33)
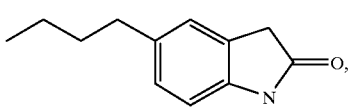

(O-34)
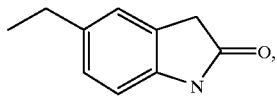

(O-55)
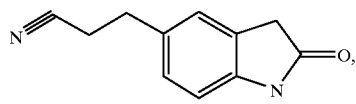

(O-35)
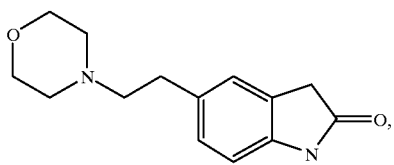

(O-53)
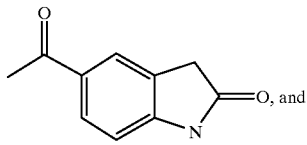, and (O-54)
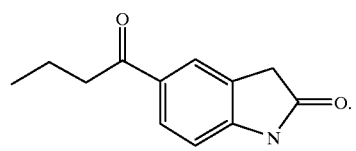.

In another aspect, the invention features an oxindole compound of formula VI

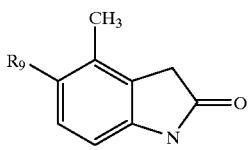

(VI)

where $R_9$ is selected from the group consisting of (i) an amine of formula —$(X_1)_{n1}$—$NX_2X_3$, where $X_1$ is selected from the group consisting of saturated or unsaturated alkyl, and five-membered or six-membered aromatic, heteroaromatic, or aliphatic ring moieties and where $n_1$ is 0 or 1, and where $X_2$ and $X_3$ are independently selected from the group consisting of hydrogen, saturated or unsaturated alkyl, and five-membered or six-membered aromatic, heteroaromatic, or aliphatic ring moieties;

(ii) a nitro of formula —$NO_2$;

(iii) a chlorine, bromine, or iodine;

(iv) a ketone of formula —$(X_4)_{n4}$—CO—$X_5$, where $X_4$ and $X_5$ are independently selected from the group consisting of alkyl optionally substituted with halogen, trihalomethyl, carboxylate, nitro, ester, and five-membered or six-membered aromatic, heteroaromatic, aliphatic, or heteroaliphatic ring moieties, where the ring moieties are optionally substituted with one, two, or three substituents independently selected from the group consisting of alkyl, halogen, trihalomethyl, carboxylate, nitro, and ester moieties and where n4 is 0 or 1;

(v) a carboxylic acid of formula —$(X_6)_{n6}$—COOH or ester of formula —$(X_7)_{n7}$—COO—$X_8$, where $X_6$, $X_7$, and $X_8$ and are independently selected from the group consisting of alkyl and five-membered or six-membered aromatic, heteroaromatic, aliphatic, or heteroaliphatic ring moieties and where n6 and n7 are independently 0 or 1;

(vi) an amide of formula —$(X_{12})_{n12}$—$NHCOX_{13}$, or of formula —$(X_{14})_{n14}$—$CONX_{15}X_{16}$, where $X_{12}$ and $X_{14}$ are each independently selected from the group consisting of alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester and where n12 and n14 are independently 0 or 1, and where $X_{13}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, where the ring is optionally substituted with one or more substituents independently selected from the group consisting of alkyl, halogen, trihalomethyl, carboxylate, nitro, and ester; and (vii) a sulfonamide of formula —$(X_{17})_{n17}$—$SO_2NX_{18}X_{19}$, where $X_{17}$ is selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$, and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, nitro, and ester and where n17 is 0 or 1.

The oxindole compound of formula VI is preferably selected from the group consisting of

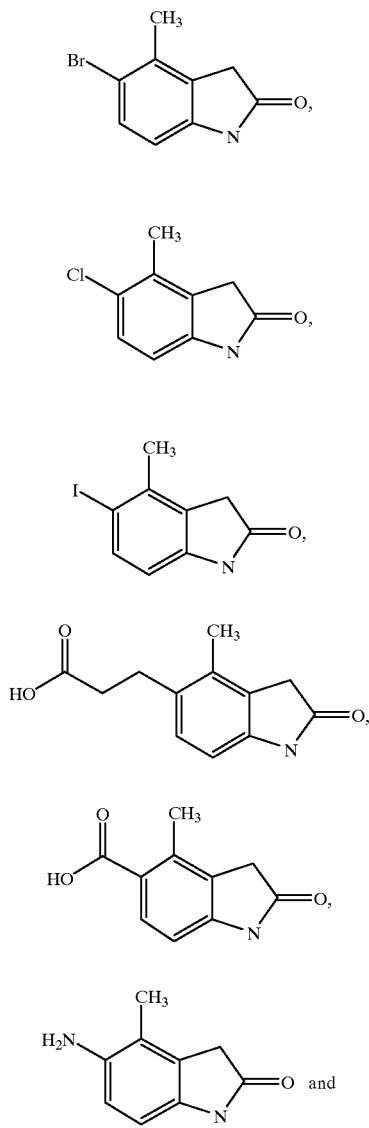

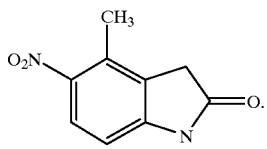

In another aspect, the invention features an oxindole compound of formula VII

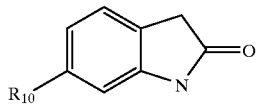

where $R_{10}$ is selected from the group consisting of (i) an aromatic or heteroaromatic ring optionally substituted with one, two, or three substituents independently selected from the group consisting of alkyl, alkoxy, halogen, trihalomethyl, carboxylate, nitro, amide, and ester moieties;

(ii) an aliphatic or heteroaliphatic ring optionally substituted with one, two, or three substituents independently selected from the group consisting of alkyl, alkoxy, halogen, trihalomethyl, carboxylate, nitro, ester, and an aromatic or heteroaromatic ring optionally substituted with one, two, or three substituents independently selected from the group consisting of alkyl, alkoxy, halogen, trihalomethyl, carboxylate, nitro, and ester moieties;

(iii) an amine of formula $—(X_1)_{n1}—NX_2X_3$, where $X_1$ is selected from the group consisting of saturated or unsaturated alkyl, and five-membered or six-membered aromatic, heteroaromatic, or aliphatic ring moieties and where n1 is 0 or 1, and where $X_2$ and $X_3$ are independently selected from the group consisting of hydrogen, saturated or unsaturated alkyl, and five-membered or six-membered aromatic, heteroaromatic, or aliphatic ring moieties, or where $X_2$ and $X_3$ taken together form a 5-membered or 6-membered heteroaliphatic ring;

(iv) a nitro of formula $—NO_2$;

(v) a bromine;

(vi) a ketone of formula $—(X_4)_{n4}—CO—X_5$, where $X_4$ and $X_5$ are independently selected from the group consisting of alkyl optionally substituted with halogen, trihalomethyl, carboxylate, nitro, ester, and five-membered or six-membered aromatic, heteroaromatic, aliphatic, or heteroaliphatic ring moieties, where the ring moieties are optionally substituted with one, two, or three substituents independently selected from the group consisting of alkyl, halogen, trihalomethyl, carboxylate, nitro, and ester moieties and where n4 is 0 or 1;

(vii) a carboxylic acid of formula $—(X_6)_{n6}—COOH$ or ester of formula $—(X_7)_{n7}—COO—X_8$, where $X_6$, $X_7$, and $X_8$ and are independently selected from the group consisting of alkyl and five-membered or six-membered aromatic, heteroaromatic, aliphatic, or heteroaliphatic ring moieties and where n6 and n7 are independently 0 or 1;

(viii) a sulfonamide of formula —$(X_{17})_{n17}$—$SO_2NX_{18}X_9$, where $X_{17}$ is selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$, and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and where $X_{18}$ and $X_{19}$ taken together form a five-membered or six-membered aliphatic or heteroaliphatic ring optionally substituted with one or more substituents independently selected from the group consisting of alkyl, halogen, trihalomethyl, carboxylate, nitro, and ester and where n17 is 0 or 1.

The oxindole compound of formula VII is preferably selected from the group consisting of

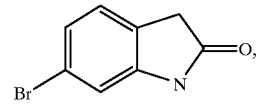
(O-51)

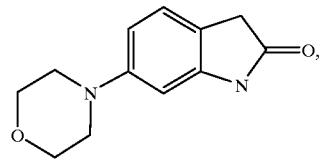
(O-58)

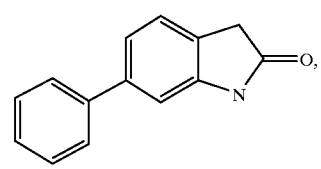
(O-46)

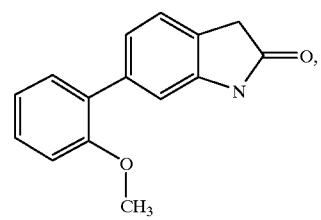
(O-47)

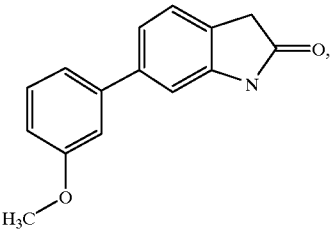
(O-48)

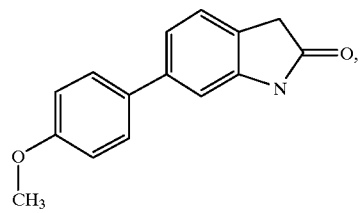
(O-49)

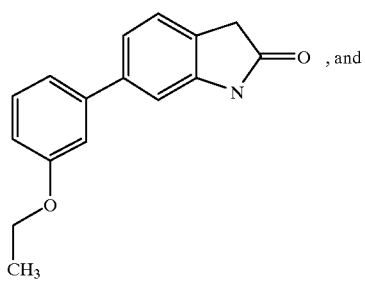
(O-50), and

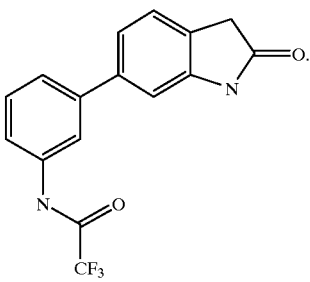
(O-60)

In a further aspect, the invention features an oxindole compound, where the oxindole compound is selected from the group consisting of

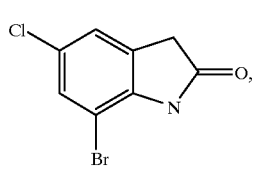
(O-8)

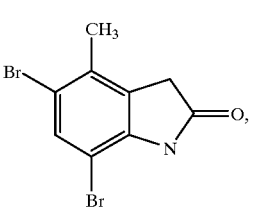
(O-32)

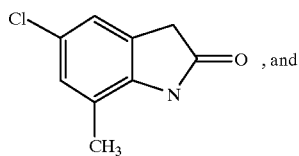
(O-40), and (O-56)

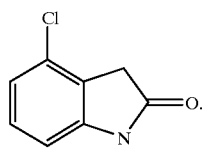

The summary of the invention described above is non-limiting and other features and advantages of the invention will be apparent from the following description of the preferred embodiments, and from the claims.

DETAILED DESCRIPTION OF THE INVENTION

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects to the extracellular microenvironment). See, Schlessinger and Ullrich, 1992, *Neuron* 9:303–391.

It has been shown that tyrosine phosphorylation sites in growth factor receptors function as high-affinity binding sites for SH2 (src homology) domains of signaling molecules. Fantl et al., 1992, *Cell* 69:413–423; Songyang et al., 1994, *Mol. Cell. Biol.* 14:2777–2785); Songyang et al., 1993, *Cell* 72:767–778; and Koch et al., 1991, *Science* 252:668–678. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreatic cancers, colon cancers, blood cancers, lung cancers and bone cancers.

I. Target Diseases to be Treated by the Compounds of the Invention

The compounds described herein are useful for treating disorders related to unregulated tyrosine kinase signal transduction, including cell proliferative disorders, fibrotic disorders and metabolic disorders.

Cell proliferative disorders which can be treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrix. Examples of fibrotic disorders include hepatic cirrhosis and mesangial cell proliferative disorders. Hepatic cirrohis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role ion hepatic cirrhosis. Other fibrotic disorders implicated include atherosclerosis (see, below).

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, *Kidney International* 43:47S–54S.

PTKs have been associated with such cell proliferative disorders. For example, some members of the RTK family have been associated with the development of cancer. Some of these receptors, like the EGFR (Tuzi et al, 1991, *Br. J. Cancer* 63:227–233; Torp et al., 1992, *APMIS* 100:713–719)

HER2/neu (Slamon et al., 1989, *Science* 244:707–712) and the PDGF-R (Kumabe et al., 1992, *Oncogene* 7:627–633) are overexpressed in many tumors and/or persistently activated by autocrine loops. In fact, in the most common and severe cancers these receptor overexpressions (Akbasak and Suner-Akbasak et al., 1992, *J. Neurol. Sci.* 111:119–133; Dickson et al., 1992, *Cancer Treatment Res.* 61:249–273; Korc et al., 1992, *J. Clin. Invest.* 90:1352–1360) and autocrine loops (Lee and Donoghue, 1992, *J. Cell. Biol.* 118:1057–1070; Korc et al, supra; Akbasak and Suner-Akbasak et al., supra) have been demonstrated. For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. The PDGF-R has been associated with glioblastoma, lung, ovarian, melanoma and prostate. The RTK c-met has been generally associated with hepatocarcinogenesis and thus hepatocellular carcinoma. Additionally, c-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkins disease, Burkitts disease, and the lymphoma cell line.

The IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.* 50:2511–2517). In addition, IGF-I, integrally involved in the normal growth and differentiation of the nervous system, appears to be an autocrine stimulator of human gliomas. Sandberg-Nordqvist et al., 1993, *Cancer Res.* 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression* 1:301–326. In a series of recent publications, Baserga even suggests that IGF-I-R plays a central role in the mechanisms of transformation and, as such, could be a preferred target for therapeutic interventions for a broad spectrum of human malignancies. Baserga, 1995, *Cancer Res.* 55:249–252; Baserga, 1994, *Cell* 79:927–930; Coppola et al., 1994, *Mol. Cell. Biol.* 14:4588–4595.

The association between abnormalities in RTKs and disease are not restricted to cancer, however. For example, RTKs have been associated with metabolic diseases like psoriasis, diabetes mellitus, wound healing, inflammation, and neurodegenerative diseases. These diseases include, but are not limited to hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders. For example, the EGF-R is indicated in corneal and dermal wound healing. Defects in the Insulin-R and the IGF-1R are indicated in type-II diabetes mellitus. A more complete correlation between specific RTKs and their therapeutic indications is set forth in Plowman et al., 1994, *DN&P* 7:334–339.

Not only receptor type tyrosine kinases, but also many cellular tyrosine kinases (CTKs) including are, abl, fps, yes, fyn, lyn, lck, blk, hck, fgr, yrk (reviewed by Bolen et al., 1992, *FASEB J.* 6:3403–3409) are involved in the proliferative and metabolic signal transduction pathway and thus in indications of the present invention. For example, mutated src (v-src) has been demonstrated as an oncoprotein ($pp60^{v-src}$) in chicken. Moreover, its cellular homolog, the proto-oncogene $pp60^{c-src}$ transmits oncogenic signals of many receptors. For example, overexpression of EGF-R or HER2/neu in tumors leads to the constitutive activation of $pp60^{c-src}$, which is characteristic for the malignant cell but absent from the normal cell. On the other hand, mice deficient for the expression of c-src exhibit an osteopetrotic phenotype, indicating a key participation of c-src in osteoclast function and a possible involvement in related disorders. Similarly, Zap 70 is implicated in T-cell signaling.

Furthermore, the identification of CTK modulating compounds to augment or even synergize with RTK aimed blockers is an aspect of the present invention.

Finally, both RTKs and non-receptor type kinases have been connected to hyperimmune disorders.

II. The KDR/FLK-1 Receptor and VEGF

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman and Shing, 1992, *J. Biological Chem.* 267:10931–34. However, many diseases are driven by persistent unregulated or inappropriate angiogenesis. For example, in arthritis, new capillary blood vessels invade the joint and destroy the cartilage. In diabetes, new capillaries in the retina invade the vitreous, bleed and cause blindness. Folkman, 1987, in: *Congress of Thrombosis and Haemostasis* (Verstraete, et. al, eds.), Leuven University Press, Leuven, pp.583–596. Ocular neovascularization is the most common cause of blindness and dominates approximately twenty (20) eye diseases.

Moreover, vasculogenesis and/or angiogenesis have been associated with the growth of malignant solid tumors and metastasis. A tumor must continuously stimulate the growth of new capillary blood vessels for the tumor itself to grow. Furthermore, the new blood vessels embedded in a tumor provide a gateway for tumor cells to enter the circulation and to metastasize to distant sites in the body. Folkman, 1990, *J. Natl. Cancer Inst.* 82:4–6; Klagsbrunn and Soker, 1993, *Current Biology* 3:699–702; Folkman, 1991, J. Natl., Cancer Inst. 82:4–6; Weidner et al., 1991, *New Engl. J. Med.* 324:1–5.

Several polypeptides with in vitro endothelial cell growth promoting activity have been identified. Examples include acidic and basic fibroblastic growth factor (aFGF, bFGF), vascular endothelial growth factor (VEGF) and placental growth factor. Unlike aFGF and bFGF, VEGF has recently been reported to be an endothelial cell specific mitogen. Ferrara and Henzel, 1989, *Biochem. Biophys. Res. Comm.* 161:851–858; Vaisman et al., 1990, *J. Biol. Chem.* 265:19461–19566.

Thus, the identification of the specific receptors to which VEGF binds is an important advancement in the understanding of the regulation of endothelial cell proliferation. Two structurally closely related RTKs have been identified to bind VEGF with high affinity: the flt-1 receptor (Shibuya et al., 1990, *Oncogene* 5:519–524; De Vries et al., 1992, Science 255:989–991) and the KDR/FLK-1 receptor, discussed in the U.S. patent application Ser. No. 08/193,829. Consequently, it had been surmised that these RTKs may have a role in the modulation and regulation of endothelial cell proliferation.

Evidence, such as the disclosure set forth in copending U.S. application Ser. No. 08/193,829, strongly suggests that VEGF is not only responsible for endothelial cell proliferation, but also is a prime regulator of normal and pathological angiogenesis. See generally, Klagsburn and Soker, 1993, *Current Biology* 3:699–702; Houck et al., 1992, *J. Biol. Chem.* 267:26031–26037. Moreover, it has been shown that KDR/FLK-1 and flt-1 are abundantly expressed in the proliferating endothelial cells of a growing tumor, but not in the surrounding quiescent endothelial cells. Plate et al., 1992, *Nature* 359:845–848; Shweiki et al., 1992, *Nature* 359:843–845.

II. Identification of Agonists and Antagonists to the KDR/FLK-1 Receptor

In view of the deduced importance of RTKs in the control, regulation and modulation of endothelial cell proliferation and potentially vasculogenesis and/or angiogenesis; many attempts have been made to identify RTK "inhibitors" using a variety of approaches. These include the use of mutant ligands (U.S. Pat. No. 4,966,849); soluble receptors and antibodies (Application No. WO 94/10202; Kendall and Thomas, 1994, *Proc. Natl. Acad. Sci. USA* 90:10705–10709; Kim et al., 1993, *Nature* 362:841–844); and RNA ligands (Jellinek et al., 1994, *Biochemistry* 33:10450–10456).

Furthermore, tyrosine kinase inhibitors (WO 94/03427; WO 92/21660; WO 91/15495; WO 94/14808; U.S. Pat. No. 5,330,992; Mariani et al., 1994, *Proc. Am. Assoc. Cancer Res.* 35:2268), and inhibitors acting on receptor tyrosine kinase signal transduction pathways, such as protein kinase C inhibitors have been identified (Schuchter et al., 1991, *Cancer Res.* 51:682–687); Takano et al., 1993, *Mol. Bio. Cell* 4:358A; Kinsella et al., 1992, *Exp. Cell Res.* 199:56–62; Wright et al., 1992, *J. Cellular Phys.* 152:448–57).

More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

Consequently, there is an unmet need for the identification and generation of effective small compounds which selectively inhibit the signal transduction of the KDR/FLK-1 receptor in order to effectively and specifically suppress vasculogenesis.

Some of the compounds of the present invention demonstrate excellent activity in biological assays and thus these compounds and related compounds are expected to be effective in treating Flk related disorders such as those driven by persistent unregulated or inappropriate angiogenesis.

IV. Pharmaceutical Formulations and Routes of Administration

The compounds described herein can be administered to a human patient per se, or in pharmaceutical compositions where it is mixed with suitable carriers or excipient(s). Techniques for formulation and administration of the compounds of the instant application may be found in "Remington's Pharmaceutical Sciences," Mack Publishing Co., Easton, Pa., latest edition.

a) Routes of Administration

Suitable routes of administration may, for example, include oral, rectal, transmucosal, or intestinal administration; intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral admninistration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carries or excipients. Examples of such carriers or excipients include but are not limited to calcium carbonate, calcium phosphate, various sugars, starches, cellulose derivatives, gelatin, and polymers such as polyethylene glycols.

Many of the PTK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

c) Effective Dosage

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

V. Biological Activity of the Indolinone Compounds

Indolinone compounds of the present invention were tested for their ability to inhibit most of protein tyrosine kinase activity. The biological assays and results of these inhibition studies are reported herein. The methods used to measure indolinone compound modulation of protein kinase function are similar to those described in U.S. application Ser. No. 08/702,232, by Tang et al., and entitled "Indolinone Combinatorial Libraries and Related Products and Methods for the Treatment of Disease," (Lyon & Lyon), filed Aug. 23, 1996, with respect to the high throughput aspect of the method. The Ser. No. 08/702,232 application is incorporated herein by reference in its entirety, including any drawings.

VI. Pharmaceutical Compositions and Administration of Indolinone Compounds

Methods of preparing pharmaceutical formulations of the compounds, methods of determining the amounts of compounds to be administered to a patient, and modes of administering compounds to an organism are disclosed in U.S. application Ser. No. 08/702,232, by Tang et al., and entitled "Indolinone Combinatorial Libraries and Related Products and Methods for the Treatment of Disease," (Lyon & Lyon), filed Aug. 23, 1996, and International patent publication number WO 96/22976, by Buzzetti et al., and entitled "Hydrosoluble 3-Arylidene-2-Oxindole Derivatives as Tyrosine Kinase Inhibitors," published Aug. 1, 1996, both of which are incorporated herein by reference in their entirety, including any drawings. Those skilled in the art will appreciate that such descriptions are applicable to the present invention and can be easily adapted to it.

EXAMPLES

The examples below are non-limiting and are merely representative of various aspects and features of the present invention. The examples describe methods for synthesizing compounds of the invention and methods for measuring an effect of a compound on the function of protein tyrosine kinases.

The cells used in the methods are commercially available. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

Example 1

Procedures for Synthesizing the Indolinone Compounds of the Invention

I. Synthesis of 2-Indolinones

A reaction mixture of the proper oxindole (1.0 equiv.), the appropriate aldehyde (1.2 equiv.), and piperidine (0.1 equiv.) in ethanol (1–2 mL/1.0 mmol oxindole) was stirred at 90° C. for 3–5 hours. After cooling, the precipitate was filtered, washed with cold ethanol, and dried to yield the target compound.

The compound of formula VI was synthesized using the above procedure and was characterized using $^1$H NMR spectroscopy.

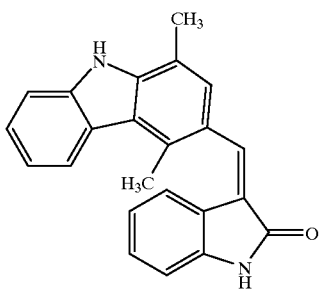

(VI)

NMR data is as follows: $^1$H NMR (360 MHz, DMSO-d6) 11.46 (s, br, 1H NH-9'), 10.52 (s, br, 1H NH-1), 8.19 (d, J=8.38 Hz, 1H, H-5'), 7.94 (s, 1H, H-vinyl), 7.58 (d, J=7.80 Hz, 1H, H-4), 7.46 (s, 1H, H-2'), 7.42 (dt, J=0.97, 7.44 Hz, 1H, H-6), 7.24 (d, J=7.91 Hz, 1H, H-8'), 7.14–7.26 (m, H-6' to H-8'), 6.86 (d, J=7.44 Hz, 1H, H-7), 6.75 (dt, J=7.80 Hz, 1H, H-5), 2.78 (s, 3H, CH$_3$-1'(4')), 2.55 (s, 3H, CH$_3$-4'(1')).

II. Synthesis of Oxindoles and Aldehydes

All of the oxindoles and aldehydes used for preparing the examples in this patent are either commercially available or prepared by the methods described below.

A. Synthesis of Oxindoles

5-Amino-2-oxindole (O-1)

5—Nitro-2-oxindole (6.3 g) was hydrogenated in methanol over 10% palladium on carbon to give 3.0 g (60% yield) of the title compound as a white solid.

5-Bromo-2-oxindole (O-2)

2-Oxindole (1.3 g) in 20 mL of acetonitrile was cooled to −10° C. and 2.0 g of N-bromosuccinimide was slowly added with stirring. The reaction was stirred for 1 hour at −10° C. and 2 hours at 0° C. The precipitate was collected, washed with water and dried to give 1.9 g (90% yield) of the title compound.

5-Chloro-2-oxindole (O-3)

5-Chloro-2-oxindole is commercially available from Aldrich Chemicals.

5,6-Dimethoxy-2-oxindole (O-4)

5,6-Dimethoxy-2-oxindole is commercially available from Maybridge.

2-Oxindole (O-5)

2-Oxindole is commercially available from Aldrich Chemicals.

4-Methyl-2-oxindole (O-6)

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6 N hydrochloric acid. The resulting precipitate was collected by vacuum filtration, washed with water, and dried under vacuum to give 9.8 g (45% yield) of 1-methyl-6-nitrophenylacetic acid as an off-white solid. The solid was hydrogenated in methanol over 10% palladium on carbon to give 9.04 g of the title compound as a white solid.

5,7-Dibromo-2-oxindole (O-7)

Same as the preparation procedures for 5-bromo-2-oxindole (O-2), using 2 equivalents of N-bromosuccinimide.

7-Bromo-5-chloro-2-oxindole (O-8)

5-Chloro-2-oxindole (16.8 g) and 19.6 g of N-bromosuccinimide were suspended in 140 mL of acetonitrile and was heated to reflux for 3 hours. Thin layer chromatography (silica, ethyl acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C. and the precipitate collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and heating to reflux for 10 minutes. The mixture was cooled in an ice bath to 10° C. The solid product was collected by vacuum filtration, washed with 25 mL of ethanol and dried under vacuum at 44° C. to give 12.7 g (51% yield) of 7-bromo-5-chloro-2-oxindole.

5-Fluoro-2-oxindole (O-9)

5-Fluoroisatin (8.2 g) was dissolved in 50 mL of hydrazine hydrate and was heated to refulux for 1 hr. The reaction mixtures were then poured in ice water. The precipitate was then filtered, washed with water and dried under vacuum oven to give the title compound.

5Nitro-2-oxindole (O-10) 2-Oxindole (6.5 g) was dissolved in 25 mL of concentrated sulfuric acid and the mixture maintained at −10–15° C. while 2.1 mL of fuming nitric acid was added dropwise. After the addition of the nitric acid the reaction mixture was stirred at 0° C. for 0.5 hr and poured into ice-water. The precipitate was collected by filtration, washed with water and crystallized from 50% acetic acid. The final crystalline product was then filtered, washed with water and dried under vacuum to give 6.3 g (70%) of 5-nitro-2-oxindole.

5-Iodo-2-oxindole (O-11)

2-Oxindole (82.9 g) was suspended in 630 mL of acetic acid with mechanical stirring and the mixture cooled to 10° C. in an ice water bath, Solid N-iodosuccinimide (175 g) was added in portions over 10 minutes. After the addition was complete the mixture was stirred for 1 hour at 10° C. The suspended solid which was always present became very thick at this time. The solid was collected by vacuum filtration, washed with 100 mL of 50% acetic acid in water and then with 200 mL of water and sucked dry for 20 minutes in the funnel. The product was dried under vacuum to give 93.5 g (36%) of 5-iodo-2-oxindole.

5-Methyl-2-oxindole (O-12)

5-Methylisatin (15.0 g) and 60 mL of hydrazine hydrate were heated to 140–160° C. for 4 hours. Thin layer chromatography (ethyl acetate:hexane 1:2, silica gel) showed no starting material remaining. The reaction mixture was cooled to room temperature, poured into 300 mL of ice water and acidified to pH 2 with 6 N hydrochloric acid. After standing at room temperature for 2 days the precipitate was collected by vacuum filtration, washed with water and dried under vacuum to give 6.5 g (47% yield) of 5-methyl-2-oxindole.

5-Bromo-4-methyl-2-oxindole (O-13) and 5,7-Dibromo-4-methyl-2-oxindole (O-32)

4-Methyl-2-oxindole (5 g) in 40 mL of acetonitrile was treated with 7.26 g of N-bromosuccinimide and stirred at room temperature for 4 hours. Thin layer chromatography (ethyl acetate:hexane 1:2, silica gel) showed a mixture of 5-bromo (Rf 0.3) and 5,7-dibromo (Rf 0.5) products. Another 7.26 g of N-bromosuccinimide was added and the mixture stirred for 4 additional hours. The solid was collected by vacuum filtration, washed with 20 mL of acetonitrile and dried to give a 1:1 mixture of mono and dibromo compounds. The filtrate was concentrated and chromatographed on silica gel (ethyl acetate:hexane 1:2) to give 1.67 g of 5-bromo-4-methyl-2-oxindole as a beige solid. The 1:1 mixture of solids was recrystallized twice from glacial acetic acid to give 3.2 g of 5,7-dibromo-4-methyl-2-oxindole as a light orange solid. The filtrates from this material were chromatographed as above to give 0.6 g of 5-bromo-4-methyl-2-oxindole and 0.5 g of 5,7-dibromo-4-methyl-2-oxindole.

6-Fluoro-2-oxindole (O-14)

Sodium hydride (2.6 g) and 14.5 g of dimethylmalonate was stirred and heated to 100° C. in 160 mL of dimethylsulfoxide for 1 hour. The mixture was cooled to room temperature and 7.95 g of 2,5-difluoronitrobenzene added and stirred for 30 minutes. The mixture was then heated to 100° C. for 1 hour, cooled to room temperature and poured into 400 mL of saturated ammonium chloride solution. The mixture was extracted with 200 mL of ethyl acetate and the organic layer washed with brine, dried over anhydrous sodium sulfate and concentrated under vacuum. The residue was crystallized from methanol to give 24.4 g (80% yield) of dimethyl 4-fluoro-2-nitrophenylmalonate as a white solid. Thin layer chromatography (ethyl acetate:hexane 1:6, silica gel) Rf 0.2. The filtrate was concentrated and chromatographed on a column of silica gel (ethyl acetate:hexane 1:8) to give 5.03 g of dimethyl 4-fluoro-2-nitrophenylmalonate, for a total of 29.5 g (96% yield).

Dimethyl 4-fluoro-2-nitrophenylmalonate (5.0 g) was heated to reflux in 20 mL of 6 N hydrochloric acid for 24 hours. The reaction was cooled and the white solid collected by vacuum filtration, washed with water and dried to give 3.3 g (87% yield) of 4-fluoro-2-nitrophenylacetic acid. Thin layer chromatography (ethyl acetate:hexane 1:2, silica gel) Rf 0.6.

4-Fluoro-2-nitrophenylacetatic acid (3.3 g) dissolved in 15 mL of acetic acid was hydrogenated over 0.45 g of 10% palladium on carbon under 60 psi for 2 hours. The catalyst was removed by filtration and washed with 15 mL of methanol. The combined filtrates were concentrated and diluted with water. The precipitate was collected by vacuum filtration, washed with water and dried to give 1.6 g (70% yield) of 6-fluoro-2-oxindole. Thin layer chromatography Rf 0.24. The filtrate was concentrated to give a purple solid with an NMR spectrum similar to the first crop. Chromatography of the purple solid (ethyl acetate:hexane 1:2, silica gel) gave a second crop of 6-fluoro-2-oxindole as a white solid.

6-Chloro-2-oxindole (O-15)

6-Clorooxindole is commercially available from Finorga.

5-Carboxyethyl-4-methyl-2-oxindole (O-16)

Same as the procedures for 5-Carboxyethyl-2-oxindole (O-27).

5-Aminosulfonyl-2-oxindole (O-17)

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5Methylaminosulfonyl-2-oxindole (O-18)

A suspension of 3.38 g of 5-chlorosulfonyl-2-oxindole from the oxindole O-17 in 10 mL of 2 M methylamine in tetrahydrofuran was stirred at room temperature for 4 hours at which time a white solid was present. The precipitate was collected by vacuum filtration, washed twice with 5 mL of water each time and dried under vacuum at 40° C. overnight to give 3.0 g (88% yield) of 5-methylaminosulfonyl-2-oxindole.

5-(4-Trifluoromethylphenylaminosulfonyl)-2-oxindole (O-19)

A suspension of 2.1 g of 5-chlorosulfonyl-2-oxindole from example O-18, 1.6 g of 4-trifluoromethylaniline and 1.4 g of pyridine in 20 mL of dichloromethane was stirred at room temperature for 4 hours. The precipitate was collected by vacuum filtration, washed twice with 5 mL of water each time and dried under vacuum at 40° C. overnight to give 2.4 g of crude product containing some impurities by thin layer chromatography. The crude product was chromatographed on silica gel eluting with ethyl acetate:hexane 1:2 to give 1.2 g (37% yield) of 5-(4-trifluoromethylphenylaminosulfonyl)-2-oxindole.

5-(Morpholin-4-sulfonyl)-2-oxindole (O-20)

A suspension of 2.3 g of 5-chlorosulfonyl-2-oxindole from example O-18 and 2.2 g of morpholine in 50 mL of dichloromethane was stirred at room temperature for 3 hours. The white precipitate was collected by vacuum filtration, washed with ethyl acetate and hexane and dried under vacuum at 40° C. overnight to give 2.1 g (74% yield) of 5-(morpholin-4-sulfonyl)-2-oxindole.

6-Trifluoromethyl-2-oxindole (O-21)

Dimethylsulfoxide (330 mL) was added to 7.9 g of sodium hydride followed by, dropwise, 43.6 g of diethyloxalate. The mixture was heated to 100° C. for 1 hour and cooled to room temperature. 2-Nitro-4-trifluromethyltoluene (31.3 g) was added, the reaction stirred for 30 minutes at room temperature and then heated to 100° C. for 1 hour. The reaction was cooled and poured into a mixture of saturated aqueous ammonium chloride, ethyl acetate and hexane. The organic layer was washed with saturated ammonium chloride, water and brine, dried, and concentrated to give dimethyl 2-(2-nitro-4-trifluoromethylphenyl)malonate.

The diester was dissolved in a mixture of 6.4 g of lithium chloride and 2.7 mL of water in 100 mL of dimethylsulfoxide and heated to 100° C. for 3 hours. The reaction was cooled and poured into a mixture of ethyl acetate and brine. The organic phase was washed with brine, dried with sodium sulfate, concentrated and chromatographed on silica gel in 10% ethyl acetate in hexane. The fractions containing product were evaporated to give 25.7 g of methyl 2-nitro-4-trifluoromethylphenylacetate.

Methyl 2-nitro-4-trifluoromethylphenylacetate (26 mg) was hydrogenated over 10% palladium on carbon and then heated at 100° C. for 3 hours. The catalyst was removed by filtration and the solvent evaporated to give the title compound.

5-(2-Chloroethyl -2-oxindole (O-22)

5-Chloroacetyl-2-oxindole (prepared by the same procedure used for the preparation of O-53, except starting from chloroacetyl chloride) (4.18 g) in 30 mL of trifluoroacetic acid in an ice bath was treated with 4.65 g of triethylsilane and stirred at room temperature for 3 hours. The mixture was poured into 150 mL of water and the precipitate collected by vacuum filtration, washed with 50 mL of water and dried to give 2.53 g (65% yield) of 5-(2-chloroethyl)-oxindole as a reddish-brown solid.

4-Methoxycarbonyl-2-oxindole (O-23)
Esterification of 4-carboxy-2-oxindole (O-25) with trimethylsilyldiazomethane.
5-Methoxycarbonyl-2-oxindole (O-24)
5-Iodo-2-oxindole (17 g) was was heated to reflux with 2 g of palladium diacetate, 18.2 g of triethylamine, 150 mL of methanol, 15 mL of dimethylsulfoxide and 2.6 g of DPPP in an atmosphere saturated with carbon monoxide. After 24 hours, the reaction was filtered to remove the catalyst and the filtrate concentrated. The concentrate was chromatographed on silica gel in 30% ethyl acetate in hexane. The fractions containing product were concentrated and allowed to stand. The precipitated product was collected by vacuum filtration to give 0.8 g (7%) of the title compound as an off-white solid.
4-Carboxy-2-oxindole (O-25)
A solution of trimethylsilyldiazomethane in hexane (2 M)was added dropwise to the solution of 2.01 g of 2-chloro-3-carboxy-nitrobenzene in 20 mL of methanol at room temperature until no gas evolution occurred. The excess trimethylsilyldiazomethane was quenched with acetic acid. The reaction mixture was dried by rotary pump and the residue was further dried in oven for overnight. The product (2-chloro-3-methoxycarbonyl-nitrobenzene) was pure enough for the following reaction.
Dimethyl malonate (6.0 mL) was added to the ice-cold suspension of 2.1 g of sodium hydride in 15 mL of DMSO. The reaction mixture was then stirred at 100° C. for 1 h and cooled to room temperature. 2-Chloro-3-methoxycarbonyl-nitrobenzene (2.15 g) was added to the above mixture in one portion and the mixture was heated to 100° C. for 1.5 h. The reaction mixture was then cooled to room temperature and poured into ice water, acidified to pH of 5, and extracted with ethyl acetate. The organic layer was then washed with brine, dried over anhydrous sodium sulfate and concentrated to give 3.0 g of the dimethyl 2-methoxycarbonyl-6-nitrophenylmalonate.
Dimethyl 2-methoxycarbonyl-6-nitrophenylmalonate (3.0 g) was was heated to reflux in 50 mL of 6 N hydrochloric acid overnight. The mixture was concentrated to dryness and was heated to reflux for 2 hours with 1.1 g of tin(II) chloride in 20 mL of ethanol. The mixture was filtered through Celite, concentrated and chromatographed on silica gel in ethyl acetate:hexane:acetic acid to give 0.65 g (37% yield) of 4-carboxy-2-oxindole as a white solid.
5-Carboxy-2-oxindole (O-26)
2-Oxindole (6.7 g) was added to a stirred suspension of 23 g of aluminum chloride in 30 mL of dichloroethane in an ice bath. Chloroacetyl chloride (11.3 g) was slowly added and hydrogen chloride gas was evolved. After ten minutes of stirring, the reaction was warmed to 40–50° C. for 1.5 hours. Thin layer chromatography (ethyl acetate, silica gel) showed no remaining starting material. The mixture was cooled to room temperature and poured into ice water. The precipitate was collected by vacuum filtration, washed with water and dried under vacuum to give 10.3 g (98%) of 5-chloroacetyl-2-oxindole as an off-white solid.
A suspension of 9.3 g of 5-chloroacetyl-2-oxindole was stirred in 90 mL pyridine at 80–90° C. for 3 hours then cooled to room temperature. The precipitate was collected by vacuum filtration and washed with 20 mL of ethanol. The solid was dissolved in 90 mL of 2.5 N sodium hydroxide and stirred at 70–80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.
5-Carboxyethyl-2-oxindole (O-27)
5-Cyanoethyl-2-oxindole (4.02 g) in 10 mL of water containing 25 mL of concentrated hydrochloric acid was was heated to reflux for 4 hours. The mixture was cooled, water added and the resulting solid collected by vacuum filtration, washed with water and dried to give 1.9 g (44%. yield) of the title compound as a yellow solid.
5-Amino-4-methyl-2-oxindole (O-28)
Same as the procedures for 5-aminooxindole (O-1).
5-Nitro-4-methyl-2-oxindole (O-29)
Same as the procedures for 5-nitrooxindole (O-10).
5-Chloro-4-methyl-2-oxindole (O-30)
A suspension of 3.0 g of 4-methyl-2-oxindole was stirred in 50 mL of acetonitrile at room temperature while 3.3 g of N-chlorosuccinimide was added in portions. Trifluoroacetic acid (1 mL) was then added. The suspension was stirred at room temperature for 3 days during which time solid was always present. The white solid was collected by vacuum filtration, washed with a small amount of cold acetone and dried overnight in a vacuum oven at 40° C. to give 2.5 g (68%) of 5-chloro-4-methyl-2-oxindole.
5-Iodo-4-methyl-2-oxindole (O-31)
To 2 g of 4-methyl-2-oxindole in 40 mL of glacial acetic acid in an ice bath was added 3.67 g of N-iodosuccinimide. The mixture was stirred for 1 hour, diluted with 100 mL of 50% acetic acid in water and filtered. The resulting white solid was dried under high vacuum to give 3.27 g (88% yield) of the title compound as an off-white solid.
5,7-Dibromo-4-methyloxindole (O-32)
See procedures for 5-bromo-4-methyloxindole (O-13).
5-Butyl-2-oxindole (O-33)
Triethylsilane (2.3 g) was added to 2 g of 4-butanoyl-2-oxindole in 20 mL of trifluoroacetic acid at room temperature and the solution stirred for 3 hours. The reaction was poured into ice water to give a red oil which solidified after standing. The solid was collected by vacuum filtration, washed with water and hexane and dried to give 1.7 g (91% yield) of the title compound as an off-white solid.
5-Ethyl-2-oxindole (O-34)
5-Acetyl-2-oxindole (2 g) in 15 mL of trifluoroacetic acid in an ice bath was slowly treated with 1.8 g of triethylsilane and then stirred at room temperature for 5 hours. One mL of triethylsilane was added and the stirring continued overnight. The reaction mixture was poured into ice water and the resulting precipitate collected by vacuum filtration, washed copiously with water and dried under vacuum to give 1.3 g (71% yield) of the title compound as a yellow solid.
5-(Morpholin4-yl) ethyl-2-oxindole (O-35)
5-Chloroethyl-2-oxindole (2.3 g), 1.2 mL of morpholine and 1.2 mL of diisopropylethylamine were heated overnight at 100° C. in 10 mL of dimethylsulfoxide. The mixture ws cooled, poured into water and extacted with ethyl acetate. The organic layer was washed with brine, dried and evaporated. The residue was chromatographed on silica gel in 5% methanol in chloroform to give 0.9 g (31%) of the title compound as a white solid.
5-(4-Carboxybenzamido)-2-oxindole (O-36)
5-(4-Methoxycarbonylbenzamido)-2-oxindole (0.9 g) and 0.4 g of sodium hydroxide in 25 mL of methanol was heated to reflux for 3 hours. The mixture was concentrated, water added, and the mixture acidified with 6 N hydrochloric acid.

The precipitate was collected by vacuum filtration to give 0.75 g (87%) of the title compound as a white solid.

5-(4-Methoxycarbonylbenzamido)-2-oxindole (O-38))

A mixture of 82.0 mg of 5-amino-2-oxindole and 131.0 mg of 4-methoxycarbonylbenzoyl chloride in pyridine was stirred at room temperature for 3 hr and poured into ice water. The precipitate was filtered, washed with water and dried in a vacuum oven to give 138.0 mg of 5-(4-methoxycarbonylbenzamido)-2-oxindole (81% yield).

5-Methoxy-2-oxindole (O-39)

Chloral hydrate (9.6 g) was dissolved in 200 mL of water containing 83 g of sodium sulfate. The solution was warmed to 60° C., a solution of 11.4 g of hydroxylamine hydrochloride in 50 mL of water was added and the mixture was held at 60° C. In a separate flask, 6.4 g of 4-anisidine and 4.3 mL of concentrated hydrochloric acid in 80 mL of water was warmed to 80° C. The first solution was added to the second and was heated to refulux. The reaction was heated to refulux for 2 minutes, cooled slowly to room temperature, and then cooled in an ice bath. The tan precipitate was collected by vacuum filtration, washed with water and dried under vacuum to give 8.6 g (85% yield) of N-(2-hydroximinoacetyl)anisidine.

Concentrated sulfuric acid (45 mL) containing 5 mL of water was warmed to 60° C. and 8.6 g of N-(2-hydroximinoacetyl)anisidine was added in one portion. The stirred mixture was heated to 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid.

5-Methoxyisatin (5.0 g) and 30 mL of hydrazine hydrate were heated to reflux for 15 minutes. The reaction mixture was cooled to room temperature and 50 mL of water was added. The mixture was extracted 3 times with 25 mL of ethyl acetate each time, the organic layers combined, dried over anhydrous sodium sulfate and concentrated to give a yellow solid. The solid was stirred in ethyl acetate and 1.1 g of insoluble material removed by vacuum filtration and saved. This material proved to be 2-hydrazinocarbonylmethyl-4-anisidine. The filtrate was concentrated and chromatographed on silica gel eluting with ethyl acetate:hexane 1:1 to give 0.7 g of 5-methoxy-2-oxindole as a dirty yellow solid. The 1.1 g of 2-hydrazinocarbonylmethyl-4-anisidine was heated to refulux for 1 hour in 20 mL of 1 N sodium hydroxide. The mixture was cooled, acidified to pH 2 with concentrated hydrochloric acid and extracted 3 times with 25 mL of ethyl acetate each time. The organic extracts were combined, washed with brine, dried over anhydrous sodium sulfate and concentrated to give 0.8 g of 5-methoxy-2-oxindole as a yellow solid. The combined yield was 1.5 g or 33%.

Reference

Crestin, C., and R. Saladino, Synthetic Communications 24:2839–2841 (1994).

7-Aza-2-oxindole (O-39)

3,3-Dibromo-7-azaoxindole (2.9 g) was dissolved in a mixture of 20 mL of acetic acid and 30 mL of acetonitrile. To the solution was added 6.5 g of zinc dust. The mixture was stirred for 2 hrs at room temperature. The solid was filtered from the mixture and the solvent evaporated. The residue was treated with ethyl acetate. The ethyl acetate solution containing insoluble solid was passed through a short column of silica gel. The collected ethyl acetate solution was evaporated and the residue dried under vacuum to give 1.8 g (yield 91%) of 7-azaoxindole acetic acid salt.

5-Chloro-7-methyl-2-oxindole (O-40)

Same procedures for 5-fluorooxindole (O-9).

7-Fluoro-2-oxindole (O-41)

Same as the procedure for 6-fluorooxindole (O-14).

4-Fluoro-2-oxindole (O-42)

Same as the procedure for 6-Fluorooxindole (O-14).

6-Methoxy-2-oxindole (O-43)

6-Methoxyoxindole is commercially available from Finorga.

5-Trifluoromethyl-2-oxindole (O-44)

Same procedures for 5-fluorooxindole (O-9).

5-Dimethylaminosulfonyl-2-oxindole (O-45)

A suspension of 2.3 g of 5-chlorosulfonyl-2-oxindole (O-17) in 10 mL of 2 M dimethylamine in methanol was stirred at room temperature for 4 hours at which time a white solid was present. The precipitate was collected by vacuum filtration, washed with 5 mL of 1 N sodium hydroxide and 5 mL of 1 N hydrochloric acid and dried under vacuum at 40° C. overnight to give 1.9 g (79% yield) of 5-dimethylaminosulfonyl-2-oxindole.

6-Phenyl-2-oxindole (O-46)

Dimethyl malonate (10 mL) in 25 mL of dimethylsulfoxide was added dropwise to 3.5 g of sodium hydride suspended in 25 mL of dimethylsulfoxide and the mixture heated at 100° C. for 10 minutes. The mixture was cooled to room temperature and 4.7 g of 4-fluoro-3-nitrobiphenyl in 25 mL of dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give a yellow oil, crude dimethyl-3-nitrobiphenyl-4-malonate.

Crude dimethyl-3-nitrobiphenyl-4-malonate was heated to refulux in 30 mL of 6 N hydrochloric acid for 24 hours. The precipitate was collected by filtration, washed with water and dried to give 4.5 g (80% based on 4-fluoro-3-nitrobiphenyl) of 3-nitrobiphenyl-4-acetic acid as a cream colored solid.

Iron powder (2.6 g) was added all at once to 4.5 g of 3-nitrobiphenyl-4-acetic acid in 40 mL of acetic acid. The mixture was heated to refulux for 2 hours, concentrated to dryness and taken up in ethyl acetate. The solids were removed by filtration and the filtrate washed twice with 1 N hydrochloric acid and brine and dried over anhydrous sodium sulfate. The filtrate was concentrated to give 3.4 g (93% yield) of 6-phenyl-2-oxindole as a light brown solid.

6-(2-Methoxyphenyl)-2-oxindole (O-47)

Tetrakis(triphenylphosphine)palladium (1 g) was added to a mixture of 5 g of 2-methoxyphenylboronic acid, 6.6 g of 5-bromo-2-fluoronitrobenzene and 30 mL of 2 M sodium carbonate solution in 50 mL of toluene and 50 mL of ethanol. The mixture was heated to refulux for 2 hours, concentrated, and the residue extracted twice with ethyl acetate. The ethyl acetate layer was washed with water, brine, dried, and concentrated to give a dark green oil which solidified on standing, crude 4-fluoro-2'-methoxy-3-nitrobiphenyl.

Dimethyl malonate (14 mL) was added dropwise to 2.9 g of sodium hydride suspended in 50 mL of dimethylsulfoxide. The mixture was heated at 100° C. for 15 minutes and cooled to room temperature. Crude 4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated sodium chloride solution and extracted twice with ethyl acetate. The extracts were combined, washed with saturated ammonium chloride, water, and brine, dried over anhydrous sodium sulfate and concentrated to give crude dimethyl 2'-methoxy-3-nitrobiphenyl-4-malonate as a yellow oil.

Crude 2'-methoxy-3-nitrobiphenyl-4-malonate was heated at 100° C. in 50 mL of 6 N hydrochloric acid for 24 hours and cooled. The precipitate was collected by filtration, washed with water and hexane, and dried to give 9.8 of 2'-methoxy-2-nitrobiphenyl-4-acetic acid as a light tan solid.

Iron powder (5 g) was added in one portion to 9.8 g of 2'-methoxy-3-nitrobiphenyl-4-acetic acid in 50 mL of glacial acetic acid was heated to 100° C. for 3 hours. The reaction mixture was concentrated to dryness, sonicated in ethyl acetate and filtered to remove the insolubles. The filtrate was washed twice with 1 N hydrochloric acid, water, brine, dried over anhydrous sodium sulfate and concentrated. The residue was chromatographed on silica gel in ethyl acetate:hexane 1:2 to give 5.4 g (69% yield based on 5-bromo-2-fluoronitrobenzene) of 6-(2-methoxyphenyl)-2-oxindole as a rose colored solid.

6-(3-Methoxyphenyl)-2-oxindole (O-48)

Tetrakis(triphenylphosphine)palladium (0.8 g) was added to a mixture of 5 g of 3-methoxyphenylboronic acid, 5 g of 5-bromo-2-fluoronitrobenzene and 11 mL of 2 M sodium carbonate solution in 100 mL of toluene. The mixture was heated to reflux for 2 hours, diluted with water and extracted with ethyl acetate. The ethyl acetate was washed with saturated sodium bicarbonate, brine, dried, and concentrated to give an oily solid. The solid was chromatographed on silica gel in ethyl acetate:hexane 1:6 to give 4.3 g (77% yield) of 4-fluoro-3'-methoxy-3-nitrobiphenyl.

Dimethyl malonate (9.7 mL) was added dropwise to 2.0 g of sodium hydride suspended in 50 mL of dimethylsulfoxide. The mixture was heated to 100° C. for 35 minutes and cooled to room temperature. 4-Fluoro-2'-methoxy-3-nitrobiphenyl (4.2 g) in 50 mL of dimethylsulfoxide was added and the mixture was heated at 100° C. for 1 hours. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude 3'-methoxy-3-nitro-biphenyl-4-malonate was heated at 110° C. in 45 mL of 6 N hydrochloric acid for 4 days and cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid 33:66:1 to give 3.0 g (75% yield based on 4-fluoro-3'-methoxy-3-nitrobiphenyl) of 6-(3-methoxyphenyl)-2-oxindole as a pink solid.

6-(4-Methoxyphenyl)-2-oxindole (O-49)

Tetrakis(triphenylphosphine)palladium (1 g) was added to a mixture of 5 g of 4-methoxyphenylboronic acid, 6,6 g of 5-bromo-2-fluoronitrobenzene and 30 mL of 2 M sodium carbonate solution in 50 mL of toluene and 50 mL of ethanol. The mixture was heated to reflux for 2 hours, concentrated, and the residue extracted twice with ethyl acetate. The ethyl acetate layer was washed with water, brine, dried, and concentrated to give a brown oily solid. The solid was chromatographed on silica gel in 5% ethyl acetate in hexane to give crude 4-fluoro-4'-methoxy-3-nitrobiphenyl as a pale yellow solid.

Dimethyl malonate (10 mL) was added dropwise to 2.0 g of sodium hydride suspended in 60 mL of dimethylsulfoxide. The mixture was heated to 100° C. for 10 minutes and cooled to room temperature. Crude 4-fluoro-2'-methoxy-3-nitrobiphenyl (5.2 g) in 50 mL of dimethylsulfoxide was added and the mixture was heated at 100° C. for 2 hours. The reaction mixture was cooled and quenched with 300 mL of saturated sodium chloride solution and extracted three times with ethyl acetate. The extracts were combined, washed with saturated ammonium chloride, water and brine, dried over anhydrous sodium sulfate and concentrated to give crude dimethyl 4'-methoxy-3-nitrobiphenyl-4-malonate as a yellow oil.

Crude 4'-methoxy-3-nitro-biphenyl-4-malonate was heated at 100° C. in 60 mL of 6 N hydrochloric acid for 15 hours and cooled. The precipitate was collected by filtration, washed with water and hexane, and dried to give 7.2 g of crude 4'-methoxy-3-nitrobiphenyl-4-acetic acid as a light tan solid.

Iron powder (3.6 g) was added in one portion to 7.2 g of 4'-methoxy-3-nitrobiphenyl-4-acetic acid in 50 mL of glacial acetic acid and heated at 100° C. overnight. The reaction mixture was concentrated to dryness, sonicated in ethyl acetate and filtered to remove the insolubles. The filtrate was washed twice with 1 N hydrochloric acid, brine, dried over anhydrous sodium sulfate and concentrated to give 2.7 g (54% yield based on 5-bromo-2-fluoronitrobenzene) of 6-(4-methoxyphenyl)-2-oxindole as a rose colored solid.

6-(3-Ethoxyphenyl-2-oxindole (O-50)

Tetrakis(triphenylphosphine)palladium (0.8 g) was added to a mixture of 4.2 g of 3-ethoxyphenylboronic acid, 5.0 g of 5-bromo-2-fluoronitrobenzene and 22 mL of 2 M sodium carbonate solution in 50 mL of toluene and 50 mL of ethanol. The mixture was heated to reflux for 2 hours, concentrated, water was added and the mixture was extracted twice with ethyl acetate. The ethyl acetate layer was washed with water, brine, dried and concentrated. The residue was chromatographed on silica gel in 5% ethyl acetate in hexane to give 5.3 g (90% yield) of crude 4-fluoro-3'-ethoxy-3-nitrobiphenyl as a yellow oil.

Dimethyl malonate (11.4 mL) was added dropwise to 4.0 g of sodium hydride suspended in 20 mL of dimethylsulfoxide. The mixture was heated to 100° C. for 10 minutes and cooled to room temperature. Crude 4-fluoro-3'-ethoxy-3-nitrobiphenyl (5.3 g) in 25 mL of dimethylsulfoxide was added and the mixture was heated at 100° C. for 2 hours. The reaction mixture was cooled and quenched with 300 mL of saturated amonium chloride solution and extracted three times with ethyl acetate. The extracts were combined, washed with water and brine, dried over anhydrous sodium sulfate and concentrated to give crude dimethyl 3'-ethoxy-3-nitrobiphenyl-4-malonate as a yellow oil.

Crude dimethyl 3'-ethoxy-3-nitrobiphenyl-4-malonate was heated at 100° C. in 60 mL of 6 N hydrochloric acid for a total of 4 days and cooled. The precipitate was collected by filtration, washed with water and hexane, and dried to give 4.7 g (77% yield based on 5-bromo-2-fluoronitrobenzene) of crude 3'-ethoxy-3-nitrobiphenyl-4-acetic acid as a light tan solid.

Iron powder (2.4 g) was added in one portion to 4.6 g of 3'-ethoxy-3-nitrobiphenyl-4-acetic acid in 40 mL of glacial acetic acid and was heated to reflux for 2 hours. The reaction mixture was concentrated to dryness, treated repeatedly with ethyl acetate and filtered to remove the insolubles. The filtrate was washed twice with 1 N hydrochloric acid, brine, died over anhydrous sodium sulfate and concentrated to give 3.5 g (91% yield) of 6-(3-ethoxyphenyl)-2-oxindole as a light brown solid.

6-Bromo-2-oxindole (O-51)

Dimethyl malonate (13 mL) was added dropwise to 2.7 g of sodium hydride suspended in 20 mL of dimethylsulfoxide. The mixture was heated to 100° C. for 10 minutes and cooled to room temperature. 5-Bromo-2-fluoronitrobenzene (5.0 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4-bromo-2-nitrophenylmalonate ag a pale yellow oil.

Crude dimethyl 4-bromo-2-nitrophenylmalonate was heated at 110° C. in 40 mL of 6 N hydrochloric acid for 24 hours and cooled. The precipitate was collected by filtration, washed with water and dried to give 5.3 g (89% yield) of 4-bromo-2-nitrophenylacetic acid as an off white solid.

4-Bromo-2-nitrophenylacetic acid 0.26 g), 0.26 g of zinc powder and 3 mL of 50% sulfuric acid in 5 mL of ethanol was heated at 100° C. overnight. The reaction mixture was filtered, diluted with a little acetic acid, concentrated to remove ethanol, diluted with water and extracted twice with ethyl acetate. The combined extracts were washed with brine, dried over anhydrous sodium sulfate and concentrated to give 0.19 g (90% yield) of 6-bromo-2-oxindole 5 g a yellow solid.

5-Carboxy-4-methyl-2-oxindole (O-52)

Same procedures as that for 5-carboxyoxindole (O-26).

5-Acetyl-2-oxindole (O-53)

2-Oxindole (3 g) was suspended in 1,2-dichloroethane and slowly treated with 3.2 mL of acetyl chloride. The resulting suspension was heated to 50° C. for 5 hours, cooled, and poured into water. The resulting precipitate was collected by vacuum filtration, washed copiously with water and dried under vacuum to give 2.9 g (73% yield) of the title compound as a brown solid.

5-Butanoyl-2-oxindole (O-54)

To 15 g of aluminum chloride suspended in 30 mL of 1,2-dichloroethane in an ice bath was added 7.5 g of 2-oxindole and then 12 g of butanoyl chloride. The resulting suspension was heated to 50° C. overnight. The mixture was poured into ice water and extracted 3 times with ethyl acetate. The combined ethyl acetate layers were washed with brine, dried over sodium sulfate, and concentrated to dryness to give a brown solid. The solid was chromatographed on silica gel in 50% ethyl acetate in hexane to give 3 g (25%) of the title compound as a yellow solid.

5-Cyanoethyl-2-oxindole (O-55)

Potassium cyanide (2.0 g) was added to 15 mL of dimethylsulfoxide and heated to 90° C. 5-Chloroethyl-2-oxindole (3.0 g) dissolved in 5 mL of dimethyl sulfoxide was added slowly with stirring, and the reaction heated to 150° C. for 2 hours. The mixture was cooled, poured into ice water and the precipitate collected by vacuum filtration, washed with water, and dried to give crude product. The crude material was chromatographed on silica gel in 5% methanol in chloroform to give 1.2 g (42% yield) of the title compound.

4-Chloro-2-oxindole (O-56)

Same procedures as that for 5-fluorooxindole (O-9).

6-Amino-2-oxindole (O-57)

6-Aminooxindole was synthesized using the procedure get forth in Helv. Chem. Acta 31:1381, 1948.

6-(Morpholin-4-yl)-2-oxindole (O-58)

6-Amino-2-oxindole (2.2 g), 4.0 g of 2,2'-dibromoethyl ether and 7.9 g of sodium carbonate were refluxed in 20 mL of ethanol overnight, concentrated and diluted with 50 mL of water. The mixture was extracted three times with 50 mL of ethyl acetate each time and the organic extracts combined, washed with 20 mL of brine, dried over anhydrous sodium sulfate and concentrated to dryness. The solid was chromatographed on a column of silica gel eluting with a 1:1 mixture of ethyl acetate:hexane containing 0.7% acetic acid to give 1.2 g (37% yield) of the title compound as a beige solid.

6-Acetylamino-2-oxindole (O-59)

6-Acetylamino-2-oxindole was synthesized using the procedure set forth in Helv. Chem. Acta 20.373, 1937.

6-(3-Trifluoroacetamidophenyl)-2-oxindole (O-60)

3-Aminophenylboronic acid (3.9 g), 5 g of 5-bromo-2-fluoronitrobenzene, 0.8 g of tetrakis(triphenylphosphine)-palladium and 23 mL of 2 M sodium bicarbonate solution in 50 mL of toluene under nitrogen was refluxed for 2.5 hours. The reaction was poured into 200 mL of ice water and the mixture extracted three times with 50 mL of ethyl acetate each time. The combined organic layers were washed with 50 mL of water and 20 mL of brine, dried over anhydrous sodium sulfate and concentrated to give 9.7 g (92% yield) of 2-fluoro-5-(3-aminophenyl)nitrobenzene as a dark brown oil.

Trifluoroacetic anhydride (5.4 mL) was slowly added to a stirred solution of 9.7 g of 2-fluoro-5-(3-aminophenyl)-nitrobenzene and 5.3 mL of triethylamine in 50 mL of dichloromethane at 0° C. and the mixture was stirred for an additional 20 minutes. The mixture was concentrated and the residue chromatographed on a column of silica gel eluting with 10% ethyl acetate in hexanes to give 8.6 g (65% yield) of 2-fluoro-5-(3-trifluoroacetyamidophenyl)-nitrobenzene as a pale orange oil which solidified on standing.

Dimethyl malonate (9.6 mL) was added dropwise to a stirred suspension of 3.2 g of 60% sodium hydride in mineral oil in 40 mL of anhydrous dimethylsulfoxide under nitrogen. The mixture was stirred for 10 minutes and 2-fluoro-5-(3-trifluoroacetamidophenyl)nitrobenzene in 20 mL of dimethylsulfoxide was added. The resulting dark red mixture was heated to 100° C. for 2 hours. The reaction was quenched by pouring into 100 mL of saturated ammonium chloride solution and extracted twice with 50 mL of ethyl acetate each time. The organic phase was washed with 50 mL each of saturated ammonium chloride solution, water, and brine, dried over anhydrous sodium sulfate and concentrated to a yellow oil. The oil was chromatographed on a column of silica gel eluting with a 1:4 mixture of ethyl acetate:hexane to give 4.4 g (50% yield) of dimethyl 2-[2-nitro-4-(3-trifluoroacetamidophenyl)phenyl]malonate as a pale yellow solid.

Dimethyl 2-[2-nitro-4-(3-trifluoroacetamidophenyl)-phenyl]malonate (4.4 g) was refluxed overnight in 50 mL of 6 N hydrochloric acid. The reaction mixture was cooled to room temperature and the solids were collected by vacuum filtration, washed with water, and dried under vacuum to give 2.7 g (73% yield) of 2-[2-nitro-4-(3-tifluoroacet-amidophenyl)phenyl]acetic acid.

2-[2-Nitro-4-(3-trifluoroacetamidophenyl)phenyl]acetic acid (100 mg) and 50 mg of iron powder in 3 mL of acetic acid was heated to 100° C. for 2 hours. The reaction mixture was concentrated and the residue sonicated in 5 mL of ethyl acetate. The insoluble solids were removed by vacuum filtration and the filtrate washed with 1 N hydrochloric acid, water and brine, dried over anhydrous sodium sulfate and concentrated to give 10 mg (14% yield) of the title compound as a rose-colored solid.

B. Synthesis of Aldehydes

Synthesis of 6,7,8,9,-Tetrahydro-5H-carbazole-3-carbaldehyde

1 The corresponding non-commercially available substituted tetrahydrocarbazoles were prepared using published procedures (*J. Chem. Soc.* 1945, 530; *Aust. J Chem.* 1952, 976; and *J. Chem. Soc.* 1950, 84, 94).

2. Vilsmeier formylation (Org. Synth. Coll., Vol. IV, 1963, 831) of the substituted 6,7,8,9,-Tetrahydro-5H-carbazoles from step 1 gives the final substituted tetrahydrocarbazole-3-carboxaldehydes.

Synthesis of Substituted 9H-Carbazole-3-carbaldehydes, Dibenzothiphen-2-carboxaldehydes, Dibenzofuran-2-carboxaldehydes, 6,7,8,9-Tetrahydro-dibenzofuran-2-carbaldehyde, 9H-β-Carboline-6-carbaldehyde, 9H-2,4,9-Triaza-fluorene-6-carbaldehyde, 9H-Pyrido[2,3-b]indole-6-carbaldehyde, 9-Thia-1,5,7-triaza-fluorene-3-carbaldehyde, and Furo[3,2-b;4,5-b']dipyridine-2-carbaldehyde Substituted 9H-carbazole-3-carbaldehydes, dibenzothiphen-2-carboxaldehydes, and dibenzofuran-2-carboxaldehydes are prepared by conventional Vilsmeier formylation starting from commercially available substituted 9H-carbazole, dibenzothiphen, dibenzofuran, 6,7,8,9-tetrahydro-dibenzofuran, 9H-β-carboline, 9H -2,4,9-triaza-fluorene, 9H-Pyrido[2,3-b]indole-6-carbaldehyde, 9-Thia-1,5,7-triaza-fluorene-3-carbaldehyde, and Furo[3,2-b;4,5-b']dipyridine.

Assay Procedures

The following in vitro assays may be used to determine the level of activity and effect of the different compounds of the present invention on one or more of the PKS. Similar assays can be designed along the same lines for any PK using techniques well known in the art.

The cellular/catalytic assays described herein are performed in an ELISA format. The general procedure is as follows: a compound is introduced to cells expressing the test kinase, either naturally or recombinantly, for some period of time after which, if the test kinase is a ligand known to activate the receptor's activity is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phoshorylation on the substrate is detected with an antibody specifically recognizing phoshotyrosine compared with control cells that were not contacted with a test compound.

The cellular/biologic assays described herein measure the amount of DNA made in response to activation of a test kinase, which is a general measure of a proliferative response, The general procedure for this assay is as follows: a compound is introduced to cells expressing the test kinase, either naturally or recombinantly, for some period of time after which, if the test kinase is a receptor, a ligand known to activate the receptor's activity is added. After incubation at least overnight, a DNA labeling reagent such as Bromodeoxy-uridine (BrdU) or 3H-thymidine is added. The amount of labeled DNA is detected with either an anti-BrdU antibody or by measuring radioactivity and is compared to control cells not contacted with a test compound.

Biochemical Assays

Example 2

FLK-1 Autophosphorylation Assay in vitro

The following protocol describes the ELISA procedures used to determine the FLK-1 autophosphorylation activity in vitro. The procedure also describes the protocol for the initial screening of indolinone compounds.

Reagents and Supplies 1. 15 cm tissue culture dishes.
2. FLK-1/NIH cells: NIH fibroblast line overexpressing human FLK-1 clone 3 (MPI, Martinsried, Germany).
3. Growth medium: DMEM plus heat-inactivated 10% FBS and 2 mM Glutamine (Gibco-BRL, Gaithersburg, USA).
4. Starvation medium: DMEM plus 0.5% heat-inactivated FBS and 2 mM Glutamine (Gibco-BRL, Gaithersburg, USA).
5. Corning 96-well ELISA plates (Corning Cat. #25805-96).
6. L4 or E38: monoclonal antibody specific for FLK-1; purified by protein-A agarose affinity chromatography (SUGEN, Inc., Redwood City, Calif.).
7. PBS (Dulbecco's Phosphate-Buffered Saline) (Gibco Catalog #450-1300EB)

| | |
|---|---|
| KCL | 2.7 mM |
| KH$_2$PO$_4$ | 1.1 mM |
| MgCl$_2$ (anhydrous) | 0.5 mM |
| NaCl | 138 mM |
| Na$_2$HPO$_4$ | 8.1 mM |

HNTG

| | |
|---|---|
| HEPES/HCl | 20 mM |
| NaCl | 150 mM |
| Glycerol | 10% |
| Triton X-100 | 1.0% |
| PMSF | 1 mM (optional) |

9. Pierce BCA protein determination kit.
10. Blocking buffer 5% Carnation instant milk in PBS
11, TBST, pH7,0

| | |
|---|---|
| Tris/HCl | 50 mM |
| NaCl | 150 mM |
| Triton X-100 | 0.1% |

12. Kinase buffer

| | |
|---|---|
| Tris/HCl | 25 mM |
| NaCl | 100 mM |
| MnCl$_2$ | 10 mM |
| Glycerol | 2% |
| Add the following just prior to use: | |
| DTT | 0.5 mM |
| Triton X-100 | 0.1% |

13. Kinase stop solution

| EDTA | 200 mM |

14. Biotinylated 4G10, specific for phosphotyrosine (UBI Cat #16-103, Lake Placid, N.Y.).
15. AB kit (Vector Laboratories, Cat #PK 4000, Burlingame, Calif).
16. DMSO
17. NUNC 96-well V bottom polypropylene plates for compounds (Applied Scientific, Cat #AS-72092).
18. ABTS solution

| Citric Acid (anhydrous) | 100 mM |
| $Na_2HPO_4$, pH 4.0 | 250 mM |
| ABTS | 0.5 mg/mL |

19. Hydrogen perosice 30% solution (Fisher Cat #H325). Store in the dark at 4° C. until ready to use,
20. ABTS/$H_2O_2$

| ABTS solution | 15 mL |
| $H_2O_2$ | 2 μL |

21. ATP (Sigma Cat #A-7699).
22. TBST, pH 7.0

| Tris/HCl | 50 mM |
| NaCl | 150 mM |

23. 20% DMSO in TBS pH 7.0.
Procedure
A. Cell Growth and Lysate Preparation
 1. Seed cell into growth medium and grow for 2–3 days foo 90–100% confluency at 37° C. and 5% $CO_2$. Do not exceed passage #20.
 2. Remove the medium and wash the cells twice with PBS. Lyse with HNTG lysis buffer. Collect all lysates and mix them on a vortex for 20–30 seconds.
 3. Remove insolubel material by centrifugation (5–10 min at ~10,000×g).
 4. Determine the protein concentration via BCA kit.
 5. Aliquot lysates into 1 mg aliquots, store at −80° C.
B. Assay Procedure
 1. Coat Corning 96-well ELISA plates with 2 ug/well of purified L4 (or E38) in 100 μL of PBS overnight at 4° C.
 2. Remove unbound proteins from wells by inverting the plate to remove the liquid. Wash one time with d-$H_2O$, pat plate on paper towel to remove excess liquid.
 3. Block plates with 150 μL blocking buffer per well. Incubate for 45–60 minutes while shaking at 4° C.
 4. Remove the blocking buffer and wash the ELISA plate three times with d-$H_2O$ and one time with TBST. Pat plate on paper towel to remove excess liquid.
 5. Dilute lysate in PBS to give final concentration of 50 ug/100 μL. Add 100 μL of diluted lysate per well. Incubate with shaking at 4° C. overnight.
 6. Remove unbound proteins from wells by inverting the plate. Wash as in step 4.

7. Add 80 μL of kinase buffer to the wells (negative control wells get 90 μL).
 8. Dilute compounds (normally 10 fold) into wells of a polypropylene plate containing 20% DMSO in TBS.
 9. Add 10 μL of the prediluted compounds to the ELISA wells containing immobilized FLK-1 and shake. Control wells receive no compound.
 10. From stock 1 mM ATP prepare a 0.3 mM ATP solution in d-$H_2O$ (kinase buffer may also be used).
 11. Add 10 μL of 0.3 mM ATP to all wells except the negative controls. Incubate for 60 min at room temperature with shaking.
 12. After 10–15 min stop the kinase reaction with the addition of 11 μL 200 mM EDTA. Let shake for 1–2 min.
 13. Wash the ELISA plate 4 times with d-$H_2O$ and twice with TBST.
 14. Add 100 μL of 1:5000 fold diluted biotinylated 4G10 (in TBST) to all wells. Incubate 45 min with shaking at room temperature,
 15. While the above is incubating, add 50 μL of solutions A & B (of the ABC kit)/10 mL of TBST. These must be combined ~30 min prior to use.
 16. Wash plates as in step 4.
 17. Add 100 μL of the above preformed complex (solution A & B in TBST) to all wells. Incubate 30 min with shaking at room temperature.
 18. Wash plates as in step 4.
 19. Add 100 μL ABTS/$H_2O_2$ solution. Shake at room temperature of 5–10 min.
 20. When the color in the positive control wells reaches an absorbance of about 0.35–0.4, read plates on Dynatech MR7000 ELISA reader.
 Test filter: 630 nm
 Reference filter: 410 nm
 The $IC_{50}$ values measured in the above assay for the compound of formula VI are depicted in Table 1:

TABLE 1

(VI)

| Compound | $IC_{50}$ (μM) |
|---|---|
| VI | >50 |

Example 3

Biochemical EGFR Assay

The following protocol describes the procedures used to analyze protein tyrosine kinase activity on the EGFR in an Elisa. The procedure also describes the protocol for the initial screening of drugs for inhibition or activation of protein tyrosine kinase activity.
Reagents and Supplies
1. Corning 96-well Elisa plates (Corning Catalog #25805-96)

2. 05–101 monoclonal anti-EGFR antibody (commercially available from UB1) −80° C., 1 mL aliquots
3. PBS (Dulbecco's Phosphate-Buffered Saline) (Gibco Catalog #450-1300EB)

| KCL | 2.7 mM |
|---|---|
| $KH_2PO_4$ | 1.1 mM |
| $MgCl_2$ (anhydrous) | 0.5 mM |
| NaCl | 138 mM |
| $Na_2HPO_4$ | 8.1 mM |

4, TBST Buffer

| Tris, pH 7.2 | 50 mM |
|---|---|
| NaCl | 150 mM |
| Triton X-100 | 0.1% |

5. Blocking Buffer
  5% Carnation Instant Milk in PBS
6. A431 cell lysate
  A431 cells are available from a variety of commercial sources and may be used lysed using conventional methods known to those skilled in the art or as described for lysis of the 3T3 cells in the EGF cellular assay described herein. −80° C., 1 mL aliquots
7. TBS Buffer

| Tris, pH 7.2 | 50 mM |
|---|---|
| NaCl | 150 mM |

8. TBS+10% DMSO (DMSO from Sigma, Catalog #D-2650) DMSO in TBS Buffer 10%
9. $ATP/MnCl_2$ phosphorylation mix (Adenosine-5'-triphosphate, Sigma Catalog #A-5394)

| ATP | 0.03 mM |
|---|---|
| $MnCl_2$ | 50 mM |

Make fresh in autoclaved Milli-Q $H_2O$ immediately before use. Keep on ice until use.
10. NUNC 96-well V bottom polypropylene plates (Applied Scientific Catalog #AS-72092)
11. EDTA, pH8.0 200 mM
12. Rabbit polyclonal anti-phosphotyrosine serum or UB40 monoclonal antibody specific for phosphotyrosine; −80° C., 1 mL aliquots, Thaw 1 mL vial and aliquot in smaller volumes to store at −80° C. Antiserum is stable for weeks when thawed and stored at 4° C.
13. Goat anti-rabbit IgG peroxidase conjugate (Biosource Catalog #ALI0404)
14. ABTS Solution

| Citric Acid (anhydrous) | 100 mM |
|---|---|
| $Na_2HPO_4$, pH 4.0 | 250 mM |
| ABTS | 0.5 mg/mL |

(2,2'-azino-bis(3-ethylbenzthiazoline-6-sulfonic acid) (Sigma Catalog #A-1888) Keep solution in dark at 4° C. until ready to use 15. Hydrogen peroxide 30% solution (Fisher Catalog #H325). Store in the dark at 4° C. until ready to use
16. $ABTS/H_2O_2$

| ABTS solution | 15 mL |
|---|---|
| $H_2O_2$ | 2 μL |

Prepare 5 minutes before use at room temperature.
17. 0.2 M HCL stock in $H_2O$
Procedure
  1. Coat Corning 96-well elisa plates with 0.5 μg per well 05–101 antibody. Bring final volume to 100 μL per well with PBS. Coat plates overnight at 4° C.
  2. Remove unbound 05–101 from wells by inverting plate to remove liquid. Wash 1× with distilled H2O by filling wells. Pat the plate on a paper towel to remove excess liquid.
  3. Block plates with 5% milk in PBS. 150 μL per well. Incubate plate 30 minutes while shaking on a microtiter plate shaker.
  4. Wash plate 3× with dionized water, then once with TBST.
  5. Add 7 μg A431 cell lysate per well (EGFR source). Add PBS to final volume of 100 μL per well. Incubate 30 minutes while shaking.
  6. Wash as described in step 4.
  7. At this point, drugs or extracts are added to the wells. Dilute drugs/extracts 1:100 (unless specified otherwise) in TBS+10% DMSO in 96-well polypropylene plates. Add 120 μL TBS to ELISA plate containing captured EGFR. Add 13.5 μL diluted drugs/extracts to ELISA plate, To control wells (wells which do not receive any drug) add 135 μL TBS+1% DMSO. Incubate plate 30 minutes while shaking.
  8. Add 15 μL of 0.03 mM ATP+50 mM $MnCl_2$ phosphorylation mix directly to all wells except negative control well which does not receive $ATP/MnCl_2$ (see diagram). (150 μL final volume in well with 3 μM ATP/5 mM $MnCl_2$ final concentration in well.) Incubate 5 minutes while shaking vigorously.
  *NOTE: It is critical that $ATP/MnCl_2$ phosphorylates the receptor for 5 minutes only. It is best to add the $ATP/MnCl_2$ with an 12 channel pipettor 1 row at a time leaving 20 seconds between each row so that the reaction may be stopped with EDTA exactly 5 minutes later (this depends on the number of plates being phosphorylated in one batch). Shake between each addition.
  9. After 5 minutes, to stop reaction, add 16.5 μL of 200 mM EDTA pH 8.0 for 20 mM final in well, shaking continuously between each addition. This is done using the same timing method as above. After last row has received EDTA, shake plate an additional minute.
  10. Wash 4× with deionized water, twice with TBST.
  11. Add rabbit polyclonal anti-phosphotyrosine serum. Dilute 1:3000 in TBST. Add 100 μL per well. Incubate 30–45 minutes while shaking.
  12. Wash as described above in step 4.
  13. Add BioSource anti-rabbit peroxidase conjugate antibody. Dilute 1:2000 in TBST. Add 100 μL per well. Incubate 30 minutes while shaking.
  14. Wash as described in step 4.
  15. Add 100 μL of $ABTS/H_2O_2$ solution to well. Incubate 5 to 10 minutes while shaking. Remove bubbles.
  16. If necessary stop reaction with the addition of 100 μL of 0.2M HCl per well.
  17. Read assay on Dynatech MR7000 elisa reader.

Test Filter: 410 nM

Reference Filter: 630 nM

The $IC_{50}$ values measured in the above assay for the compound of formula VI are depicted in Table 2:

TABLE 2

(VI)

[Chemical structure of compound VI]

| Compound | $IC_{50}$ ($\mu M$) |
|---|---|
| VI | >50 |

Cellular/Catalytic Assays

Enzyme linked immunosorbent assays (ELISA) may be used to detect and measure the presence of PK activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol may be adapted for determining activity with respect to a specific PK. For example, the preferred protocols for conducting the ELISA experiments for specific P.S. is provided below. Adaptation of these protocols for determining a compound's activity for other members of the RTK family, as well as for CTKs and STKS, is well within the scope of knowledge of those skilled in the art.

Example 4

Assay Measuring the EGF Receptor Kinase Activity

EGF Receptor kinase activity in cells genetically engineered to express human EGF-R was measured as described below:

Materials and Reagents

The following materials and reagents were used:
a. EGF Ligand: stock concentration=16.5 $\mu M$; EGF 201, TOYOBO, Co., Ltd. Japan.
b. 05–101 (UBI) (a monoclonal antibody recognizing an EGFR extracellular domain).
c. Anti-phosphotyosine antibody (anti-Ptyr) (polyclonal).
d. Detection antibody: Goat anti-rabbit lgG horse radish peroxidase conjugate, TAGO, Inc., Burlingame, Calif.
e. TBST buffer:

| Tris-HCl, pH 7 | 50 mM |
|---|---|
| NaCl | 150 mM |
| Triton X-100 | 0.1 | f. HNTG 5X stock:

| HEPES | 0.1 M |
|---|---|
| NaCl | 0.75 M |
| Glycerol | 50 |
| Triton X-100 | 1.0% | g. ABTS stock:

| Citric Acid | 100 mM |
|---|---|
| $NA_2HPO_4$ | 250 mM |
| HCl, conc. | 4.0 pH |
| ABTS* | 0.5 mg/mL |

Keep solution in dark at 4° C. until used.
h. Stock reagents of:
   EDTA 100 mM pH 7.0
   $Na_3VO_4$ 0.5 M
   $Na_4(P_2O_7)$ 0.2 M Procedure The following protocol was used:
A. Pre-coat ELISA Plate
   1. Coat ELISA plates (Coming, 96 well, Cat. #25805–96) wit 05–101 antibody at 0.5 $\mu g$ per well in PBS, 150 $\mu L$ final volume/well, and store overnight at 4° C. Coated plates are good for up to 10 days when stored at 4° C.
   2. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.
B. Seeding Cells
   1. NIH 3T3/C7 cell line (Honegger, et al., Cell 51:199–209, 1987) can be use for this assay.
   2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm, and once at room temperature for 5 minutes.
   3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 $\mu L$ per well, in a 96 well microtiter plate. Incubate seeded cells in 5% $CO_2$ at 37° C. for about 40 hours.
C. Assay Procedures
   1. Check seeded cells for contamination using an inverted microscope. Dilute drug stock (10 mg/mL in DMSO) 1:10 in DMEM medium, then transfer 5 $\mu L$ to a test well for a final drug dilution of 1:200 and a final DMSO concentration of 1%. Control wells receive DMSO alone. Incubate in 5% $CO_2$ at 37° C. for one hour.
   2. Prepare EGF ligand: dilute stock EGF in DMEM so that upon transfer of 10 $\mu L$ dilute EGF (1:12 dilution), 25 nM final concentration is attained.
   3. Prepare fresh 10 mL HNTG* sufficient for 100 $\mu L$ per well wherein HNTG* comprises: HNTG stock (2.0 mL), milli-Q H2O(7.3 mL), EDTA, 100 mM, pH 7.0 (0.5 mL), $Na_3VO_4$ 0.5 M (0.1 mL) and $Na_4(P_2O_7)$, 0.2 M (0.1 mL).
   4. Place on ice.
   5. After two hours incubation with drug, add prepared EGF ligand to cells, 10 $\mu L$ per well, to yield a final concentration of 25 mM. Control wells receive DMEM alone. Incubate, shaking, at room temperature, for 5 minutes, 6. Remove drug, EGF, and DMEM. Wash cells twice with PBS. Transfer HNTG to cells, 100 μL per well. Place on ice for 5 minutes. Meanwhile, remove blocking buffer from other ELISA plate and wash with TBST as described above.

7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

8. Remove lysate and wash 4 times with TBST. Transfer freshly diluted anti-Ptyr antibody to ELISA plate at 100 μL per well. Incubate shaking at room temperature for 30 minutes in the presence of the anti-Ptyr antiserum (1:3000 dilution in TBST).

9. Remove the anti-Ptyr antibody and wash 4 times with TBST. Transfer the freshly diluted TAGO 30 anti-rabbit IgG antibody to the ELISA plate at 100 μL per well. Incubate shaking at room temperature for 30 minutes (anti-rabbit IgG antibody: 1:3000 dilution in TBST).

10. Remove detection antibody and wash 4 times with TBST. Transfer freshly prepared $ABTS/H_2O_2$ solution to ELISA plate, 100 μL per well. Incubate at room temperature for 20 minutes. $ABTS/H_2O_2$ solution: 1.2 μL 30% $H_2O_2$ in 10 mL ABTS stock.

11. Stop reaction by adding 50 μL 5N $H_2SO_4$ (optional), and determine O.D. at 410 rpm.

12. The maximal phosphotyrosine signal is determined by subtracting the value of the negative controls from the positive controls. The percent inhibition of phosphotyrosine content for extract-containing wells is then calculated, after subtraction of the negative controls.

The $IC_{50}$ values measured in the EGF receptor phosphorylation assay for the compound of formula VI are depicted in Table 3:

TABLE 3

(VI)

[Structure of compound VI]

| Compound | $IC_{50}$ (μM) |
|---|---|
| VI | >100 |

Example 5

Assay Measuring the IGF-1 Receptor Kinase Activity

The following protocol was used to measure phosphotyrosine level on IGF-1 receptor, which indicates IGF-1 receptor tyrosine kinase activity.

Materials and Reagents

The following materials and reagents were used:
a. The cell line used in this assay is 3T3-L1/IGF-1R, a cell line genetically engineered to overexpresses IGF-1 receptor.
b. NIH3T3/IGF-1R is grown in an incubator with 5% $CO_2$ at 37° C. The growth media is DMEM+10% FBS (heat inactivated)+2 mM L-glutamine.
c. Affinity purified anti-IGF-1R antibody 17–69.
d. D-PBS:

| $KH_2PO_4$ | 0.20 g/L |
| $K_2HPO_4$ | 2.16 g/L |
| KCl | 0.20 g/L |
| NaCl | 8.00 g/L (pH 7.2) | e. Blocking Buffer: TBST plus 5% Milk (Carnation Instant Non-Fat Dry Milk).
f. TBST buffer:

| Tris-HCl | 50 mM |
| NaCl | 150 mM (pH 7.2/HCl 1 N) |
| Triton X-100 | 0.1% |

Stock solution of TBS (10×) is prepared, and Triton X-100 is added to the buffer during dilution.
g. HNTG buffer

| HEPES | 20 mM |
| NaCl | 150 mM (pH 7.2/HCl 1 N) |
| Glycerol | 10% |
| Triton X-100 | 0.2% |

Stock solution (5×) is prepared and kept at 4° C.
h. EDTA/HCl: 0.5 M pH 7.0 (NaOH) as 100× stock.
i. $Na_3VO_4$: 0.5 M as 100× stock and aliquots are kept in −80° C.
j. $Na_4P_2O_7$: 0.2 M as 100× stock.
k. Insulin-like growth factor-1 from Promega (Cat#G5111).
l. Rabbit polyclonal anti-phosphotyrosine antiserum.
m. Goat anti-rabbit IgG, POD conjugate (detection antibody), Tago (Cat. No. 4520, Lot No. 1802): Tago, Inc., Burlingame, Calif.
n. ABTS (2.2'-azinobis(3-ethylbenzthiazolinesulfonic acid)) solution:

| Citric acid | 100 mM |
| $a_2HPO_4$ | 250 mM (pH 4.0/1 N HCl) |
| ABTS | 0.5 mg/mL |

ABTS solution should be kept in dark and 4° C. The solution should be discarded when it turns green.
o. Hydrogen Peroxide: 30% solution is kept in the dark at 4° C.

Procedure

All the following steps are conducted at room temperature unless it is specifically indicated. All ELISA plate washings are performed by rinsing the plate with tap water three times, followed by one TBST rinse. Pat plate dry with paper towels.

A. Cell Seeding

1. The cells, grown in tissue culture dish (Corning 25020-100) to 80–90% confluence, are harvested with Trypsin-EDTA (0.25%, 0.5 mL/D-100, GIBCO).

2. Resuspend the cells in fresh DMEM+10% FBS+2mM L-Glutamine, and transfer to 96- well tissue culture plate (Corning, 250806-96) at 20,000 cells/well (100 μL/well). Incubate for 1 day then replace medium to serum-free medium (90/μL) and incubate in 5% $CO_2$ and 37° C. overnight.

B. ELISA Plate Coating and Blocking

1. Coat the ELISA plate (Corning 25805-96) with Anti-IGF-1R Antibody at 0.5 μg/well in 100 μL PBS at least 2 hours.
2. Remove the coating solution, and replace with 100 μL Blocking Buffer, and shake for 30 minutes. Remove the blocking buffer and wash the plate just before adding lysate.

C. Assay Procedures

1. The drugs are tested in serum-free condition.
2. Dilute drug stock (in 100% DMSO) 1:10 with DMEM in 96-well poly-propylene plate, and transfer 10 μL/well of this solution to the cells to achieve final drug dilution 1:100, and final DMSO concentration of 1.0%. Incubate the cells in 5% CO$_2$ at 37° C. for 2 hours.
3. Prepare fresh cell lysis buffer (HNTG*)

| | |
|---|---|
| HNTG | 2 mL |
| EDTA | 0.1 mL |
| Na$_3$VO$_4$ | 0.1 mL |
| Na$_4$(P$_2$O$_7$) | 0.1 mL |
| H$_2$O | 7.3 mL |

4. After drug incubation for two hours, transfer 10 μL/well of 200 nM IGF-1 Ligand m PBS to the cells (Final Conc.=20 nM), and incubate at 5% CO$_2$ at 37° C. for 10 minutes.
5. Remove media and add 100 μL/well HNTG* and shake for 10 minutes. Look at cells under microscope to see if they are adequately lysed.
6. Use a 12-channel pipette to scrape the cells from the plate, and homogenize the lysate by repeat aspiration and dispense. Transfer all the lysate to the antibody coated ELISA plate, and shake for 1 hour.
7. Remove the lysate, wash the plate, transfer anti-pTyr (1:3,000 with TBST) 100 μL/well, and shake for 30 minutes.
8. Remove anti-pTyr, wash the plate, transfer Tago (1:3,000 with TBST) 100 μL/well, and shake for 30 minutes.
9. Remove detection antibody, wash the plate, and transfer fresh ABTS/H$_2$O$_2$ to 10 mL ABTS) 100 μL/well to the plate to start color developments.
10. Measure OD at 410 nm with a reference wavelength of 630 nm in Dynatec MR5000.

The IC$_{50}$ values measured in the IGF-1 receptor phosphorylation assay for the compound of formula VI are depicted in Table 4:

TABLE 4

(VI)

| Compound | IC$_{50}$ (μM) |
|---|---|
| VI | 8.52 |

Example 6

Assay Measuring the PDGF Receptor Kinase Activity

All cell culture media, glutamine, and fetal bovine serum were purchased from Gibco Life Technologies (Grand Island, N.Y.) unless otherwise specified. All cells were grown in a humid atmosphere of 90–95% air and 5–10% CO$_2$ at 37° C. All cell lines were routinely subcultured twice a week and were negative for mycoplasma as determined by the Mycotect method (Gibco).

For ELISA assays, cells (U1242, obtained from Joseph schlessinger, NYU) were grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium cells were changed to serum-free medium and treated with test compound for 2 hr in a 5% CO$_2$, 37° C. incubator. Cells were then stimulated with ligand for 5–10 minute followed by lysis with HNTG (20 mM Hepes, 150 mM NaCl, 10% glycerol, 5 mM EDTA, 5 mM Na$_3$VO$_4$, 0.2%Triton X-100, and2 mM NaPyr). Cell lysates (0.5 mg/well in PBS) were transferred to ELISA plates previously coated with receptor-specific antibody and which had been blocked with 5% milk in TBST (50 mM Tris-HCl ph 7.2, 150 mM NaCl and 0.1% Triton X-100) at room temperature for 30 min. Lysates were incubated with shaking for 1 hour at room temperature. The plates were washed with TBST four times and then incubated with polyclonal anti-phosphotyrosine antibody at room temperature for 30 minutes. Excess anti-phosphotyrosine antibody was removed by rinsing the plate with TBST four times. Goat anti-rabbit IgG antibody was added to the ELISA plate for 30 min at room temperature followed by rinsing with TBST four more times. ABTS (100 mM citric acid, 250 mM Na$_2$HPO$_4$ and 0.5 mg/mL 2,2'-azino-bis(3-ethybenzthiazoline-6-sulfonic acid)) plus H$_2$O$_2$ (1.2 mL 30% H$_2$O$_2$ to 10 mL ABTS) was added to the ELISA plates to start color development. Absorbance at 410 nm with a reference wavelength of 630 nm was recorded about 15 to 30 min after ABTS addition.

The IC$_{50}$ values measured in the PDGF receptor phosphorylation assay for the compound of formula VI are depicted in Table 5:

TABLE 5

(VI)

| Compound | IC$_{50}$ (μM) |
|---|---|
| VI | 49.29 |

Example 7

Assay Measuring the EGF Receptor-HER2 Kinase Activity

HER2 kinase activity in whole EGFR-NIH3T3 cells was measured as described below.

Materials and Reagents

The following materials and reagents were used to conduct the assay;

a. EGF: stock concentration=16.5 ILM; EGF 201, TOYOBO, Co., Ltd. Japan.
b. 05-101 (UBI) (a monoclonal antibody recognizing an EGFR extracellular domain).
c. Anti-phoshotyrosine antibody (anti-Ptyr) (polyclonal) (see, Fendley, et al., supra).
d. Detection antibody: Goat anti-rabbit lgG horse radish peroxidase conjugate, TAGO, Inc., Burlingame, Calif.
e. TEST buffer:

| | |
|---|---|
| Tris-HCl, pH 7.2 | 50 mM |
| NaCl | 150 mM |
| Triton X-100 | 0.1 | f. HNTG 5× stock:

| | |
|---|---|
| HEPES | 0.1 M |
| NaCl | 0.75 M |
| Glycerol | 50% |
| Triton X-100 | 1.0% | g. ABTS stock:

| | |
|---|---|
| Citric Acid | 100 mM |
| $Na_2HPO_4$ | 250 mM |
| HCl, conc. | 0.5 pM |
| ABTS* | 0.5 mg/mL |

*(2,2'-azinobis(3-ethylbenzthiazolinesulfonic acid)). Keep solution in dark at 4° C. until use.

h. Stock reagents of: EDTA 100 mM pH 7.0 $Na_3VO_4$ 0.5 M $Na_4(P_2O_7)$ 0.2 M

Procedure

The following protocol was used:

A. Pre-coat ELISA Plate

1. Coat ELISA plates (Corning, 96 well, Cat. #25805-96) with 05–101 antibody at 0.5 g per well in PBS, 100 µL final volume/well, and store overnight at 4° C. Coated plates are good for up to 10 days when stored at 4° C.

2. on day of use, remove coating buffer and replace with 100 µL blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TEST buffer.

B. Seeding Cells

1. An NIH3T3 cell line overexpressing a chimeric receptor containing the EGFR extracellular domain and intracellular HER2 kinase domain can be used for this assay.

2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µL per well, in a 96 well microtiter plate. Incubate seeded cells in 5% $CO_2$ at 37° C. for about 40 hours.

C. Assay Procedures

1. Check seeded cells for contamination using an inverted microscope. Dilute drug stock (10 mg/mL in DMSO) 1:10 in DMEM medium, then transfer 5 l to a TBST well for a final drug dilution of 1:200 and a final DMSO concentration of 1%. Control wells receive DMSO alone. Incubate in 5% $CO_2$ at 37° C. for two hours.

2. Prepare EGF ligand: dilute stock EGF in DMEM so that upon transfer of 10 41 dilute EC37 :12 dilution), 100 nM final concentration is attained.

3. Prepare fresh HNTG sufficient for 100 µL per well; and place on ice.

HNTG (10 mL):

| | |
|---|---|
| HNTG stock | 2.0 mL |
| milli-Q $H_2O$ | 7.3 mL |
| EDTA, 100 mM, pH 7.0 | 0.5 mL |
| $Na_3VO_4$, 0.5 M | 0.1 mL |
| $Na_4(P_2O_7)$, 0.2 M | 0.1 mL |

4. After 120 minutes incubation with drug, add prepared SGF ligand to cells, 10 µL per well, to a final concentration of 100 nM. Control wells receive DMEM alone. Incubate, shaking, at room temperature, for 5 minutes.

5. Remove drug, EGF, and DMEM. Wash cells twice with PBS. Transfer HNTG* to cells, 100 µL per well. Place on ice for 5 minutes. Meanwhile, remove blocking buffer from other ELISA plate and wash with TBST as described above.

6. With a pipette tip securely fitted to a micropipettor, scrape cells from plate and homogenize cell material by repeatedly aspirating and dispensing the HNTG* lysis buffer. Transfer lysate to a coated, blocked, and washed ELISA olate. Incubate shaking at room temperature for one hour.

7. Remove lysate and wash 4 times with TB ST. Transfer freshly diluted anti-Ptyr antibody to ELISA plate at 100 µL per well. Incubate shaking at room temperature for 30 minutes in the presence of the anti-Ptyr antiserum (1:3000 dilution in TBST).

8. Remove the anti-Ptyr antibody and wash 4 times with TBST. Transfer the freshly diluted TAGO anti-rabbit IgG antibody to the ELISA plate at 100 µL per well. Incubate shaking at room temperature for 30 minutes (anti-rabbit IgG antibody: 1:3000 dilution in TBST).

9. Remove TAGO detection antibody and wash 4 times with TBST. Transfer freshly prepared ABTS/$H_2O_2$ solution to ELISA plate, 100 µL per well. Incubate shaking at room temperature for 20 minutes. (ABTS/$H_2O_2$ solution: 1.0 µL 30% $H_2O_2$ in 10 mL ABTS stock).

10. Stop reaction by adding 50 µL 5N $H_2SO_4$ (optional), and determine O.D. at 410 nm.

11. The maximum phosphotyrosine signal is determined by subtracting the value of the negative controls from the positive controls. The percent inbibitation of phosphotyrosine content for extract-containing wells is then calculated, after subtraction of the negative controls.

The $IC_{50}$ values measured in the EGF receptor-HER2 phosphorylation assay for the compound of formula VI are depicted in Table 6:

TABLE 6

(VI)

[Structure of compound VI: a carbazole with CH₃ groups bearing an exocyclic methylidene linked to an oxindole]

| Compound | IC$_{50}$ ($\mu$M) |
|---|---|
| VI | 8.72 |

Example 8

Assay Measuring the Insulin Receptor Kinase Activity

The following protocol was used to determine whether the compounds of the present invention possessed insulin receptor tyrosine kinase activity.

Materials and Reagents

The following materials and reagents were used to measure phophotyrosine levels on the insulin receptor (indicating insulin receptor tyrosine kinase activity):

1. The preferred cell line was an NIH3T3 cell line (ATCC No. 1658) which overexpresses Insulin Receptor (H25 cells);
 2. H25 cells are grown in an incubator with 5% $CO_2$ at 37° C. The growth media is DMEM+10% FBS (heat inactivated)+2 mm L-Glutamine;
 3. For ELISA plate coating, the monoclonal anti-IR antibody named BBE is purified and used;
 4. D-PBS, comprising:

| | |
|---|---|
| KH$_2$PO$_4$ | 0.20 g/L (GIBCO, 310-4190AJ) |
| K$_2$HPO$_4$ | 2.16 g/L |
| KCl | 0.20 g/L |
| NaCl | 8.00 g/L (pH 7.2); |

5. Blocking Buffer: TBST plus 5% Milk (Carnation Instant Non-Fat Dry Milk);
 6. TBST buffer, comprising:

| | |
|---|---|
| Tris-HCl | 50 mM |
| NaCl | 150 mM pH 7.2 (HCl, 1 N) |
| Triton X-100 | 0.1% |

Note: Stock solution of TBS (10×) is prepared, and Triton X-100 is added to the buffer during dilution;

7. HNTG buffer, comprising:

| | |
|---|---|
| HEPES | 20 mM |
| NaCl | 150 mM pH 7.2 (HCl, 1 N) |
| Glycerol | 10% |
| Triton X-100 | 0.2% |

Note: Stock solution (5×) is prepared and kept at 4° C.;

8. EDTA.HCl: 0.5 M pH 7.0 (NaOH) as 100× stock;
 9. Na$_3$VO$_4$: 0.5 M as 100× stock and aliquots are kept in −80° C.;
 10. Na$_4$P$_2$O$_7$: 0.2 M as 100× stock;
 11. Insulin from GIBCO BRL (Cat #18125039);
 12. Polyclonal antiserum Anti-phosphotyrosine: rabbit sera or UB40 monoclonal antibody specific for phosphotyrosine.
 13. Detection antibody, preferably goat anti-rabbit IgG, POD conjugate, Tago (Cat. No. 4520: Lot No. 1802): Tago, Inc., Burlingame, Calif.;
 14. ABTS solution, comprising:

| | |
|---|---|
| Citric acid | 100 mM |
| Na$_2$HPO$_4$ | 250 mM pH 4.0 (1 N HCl) |
| ABTS | 0.5 mg/mL | wherein ABTS is 2,2'-azinobis (3-etylbenathiazolinesulfonic acid) and stored in the dark at 4° C. and discarded when it turns green;

15. Hydrogen Peroxide: 30% solution is kept in the dark and at 40° C.

Protocol

All the following steps are conducted at room temperature unless it is specifically indicated. All ELISA plate washings are performed by rinsing the plate with tap water three times, followed by one TBST rinse. All plates were tapped dry with paper towels prior to use.

A. Cell Seeding

1. The cells were grown in tissue culture dish (10 cm, Corning 25020-100) to 80–90% confluence and harvested with Trypsin-EDTA (0.25%, 0.5 mL/D-100, GIBCO);
 2. Resuspend the cells in fresh DMEM+10% FBS+2mM L-Glutamine, and transfer to 96-well tissue culture plate (Corning, 25806-96) at 20,000 cells/well (100 $\mu$L/well). The cells are then incubated for 1 day. Following such incubation, 0.01% serum medium (90/$\mu$L) replaces the old media and the cells incubate in 5% $CO_2$ and 37° C. overnight.

B. ELISA Plate Coating and Blocking

1. Coat the ELISA plate (Corning 25805-96) with Anti-IR Antibody at 0.5 $\mu$g/well in 100 $\mu$L PBS at least 2 hours.
 2. Remove the coating solution, and replace with 100 $\mu$L; blocking Buffer, and shake for 30 minutes. Remove the blocking buffer and wash the plate just before adding lysate.

C. Assay Procedures 1. The drugs are tested in serum-free condition. 2. Dilute drug stock (in 100% DMSO) 1:10 with DMEM in 96-well poly-propylene plate, and transfer 10 $\mu$L/well of this solution to the cells to achieve final drug dilution 1:100, and final DMSO concentration of 1.0%. Incubate the cells in 5% $CO_2$ at 37° C. for 2 hours.

3. Prepare fresh cells lysis buffer (HNTG*)

| | |
|---|---|
| HNTG (5×) | 2 mL |
| EDTA | 0.1 mL |
| Na$_3$VO$_4$ | 0.1 mL |

-continued

| | |
|---|---|
| Na$_4$P$_2$O$_7$ | 0.1 mL |
| H$_2$O | 7.3 mL |
| HNTG* | 10 mL |

4. After drug incubation for two hours, transfer 10 μL/well of 1 μM insulin in PBS to the cells (Final concentration=100 nM), and incubate at 5% CO$_2$ at 37° C. for 10 minutes.

5. Remove media and add 100 μL/well HNTG* and shake for 10 minutes. Look at cells under microscope to see if they are adequately lysed.

6. Using a 12-channel pipette, scrape the cells from the plate, and homogenize the lysate by repeat aspiration and dispense. Transfer all the lysate to the antibody coated ELISA plate, and shake for 1 hour.

7. Remove the lysate, wash the plate, transfer anti-pTyr (1:3,000 with TBST) 100 μL/well, and shake for 30 minutes.

8. Remove anti-pTyr, wash the plate, transfer Tago (1:3,000 with TBST) 100 μL/well, and shake for 30 minutes.

9. Remove detection antibody, wash the plate, and transfer fresh ABTS/H$_2$O$_2$ (1.2 μL H$_2$O$_2$ to 10 mL ABTS) 100 μL/well to the plate to start color development.

10. Measure OD in Dynatec MR5000, which is connected to Ingres. All following steps should follow Ingres instruction.

The IC$_{50}$ values measured in the insulin receptor phosphorylation assay for the compound of formula VI are depicted in Table 7:

TABLE 7

(VI)

| Compound | IC$_{50}$ (μM) |
|---|---|
| VI | 21.94 |

Example 9

Assay Measuring the FLK-1 Receptor Kinase Activity

An ELISA assay was conducted to measure the kinase activity of the FLK-1 receptor and more specifically, the inhibition or activation of TK activity on the FLK-1 receptor. Specifically, the following assay was conducted to measure kinase activity of the FLK-1 receptor in cells genetically engineered to express FLK-1.

Materials and Methods

The following reagents and supplies were used:

a. Corning 96-well ELISA planes (Corning Catalog No. 25805-96);
b. Cappel goat anti-rabbit IgG (catalog no. 55641);
c. PBS (Gibco Catalog No. 450-1300EB);
d. TBSW Buffer (50 mM Tris pH 7.2), 150 mM NaCl and 0.1% Tween-20);
e. Ethanolamine stock (10% ethanolamine (pH 7.0), stored at 4° C.);
f. HNTG buffer (20 mM HEPES buffer (H 7.5), 150 mM NaCl, 0.2% Triton X-100, and glycerol);
g. EDTA (0.5 M (pH 7.0) as a 100× stock);
h. Sodium ortho vanadate (0.5 M as a 100× stock);
i. Sodium pyro phosphate (0.2M as a 100× stock);
j. NUNC 96 well V bottom polypropylene plates (Applied Scientific Catalog No. AS-72092);
k. NIH3T3 C7#3 Cells (FLK-1 expressing cells);
l. DMEM with 1× high glucose L Glutamine (catalog No. 11965-050);
m. FBS, Gibco (catalog no. 16000-028);
n. L-glutamine, Gibco (catalog no. 25030-016);
o. VEGF, PeproTech, Inc. (catalog no. 100-20)(kept as 1 μg/100 μL stock in Milli-Q dH$_2$O and stored at −20° C.;
p. Affinity purified anti-FLK-1 antiserum;
q. UB40 monoclonal antibody specific for phosphotyrosine (see, Fendley, et al., 1990, Cancer Research 50:1550–1558);
r. EIA grade Goat anti-mouse IgG-POD (BioRad catalog no. 172-1011);
s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/mL ABTS (Sigma catalog no. A-1 888)), solution should be stored in dark at 4° C. until ready for use;
t. H$_2$O$_2$ (30% solution)(Fisher catalog no. H325);
u. ABTS/H$_2$O$_2$ (15 mL ABTS solution, 2 μL H$_2$O$_2$) prepared 5 minutes before use and left at room temperature;
v. 0.2 M HCl stock in H$_2$O;
w. dimethylsulfoxide (100%)(Sigma Catalog No. D-8418); and
y. Trypsin-EDTA (Gibco BRL Catalog No. 25200-049).

Protocol

The following protocol was used for conducting the assay:

1. Coat Corning 96-well elisa plates with 1.0 μg per well Cappel Anti-rabbit IgG antibody in 0.1 M Na$_2$CO$_3$ pH 9.6. Bring final volume to 150 μL per well. Coat plates overnight at 4° C. Plates can be kept up to two weeks when stored at 4° C.

2. Grow cells in Growth media (DMEM, supplemental with 2.0 mM L-Glutamine, 10% FBS) in suitable culture dishes until confluent at 37° C., 5% CO$_2$.

3. Harvest cells by trypsinization and seed in Corning 25850 polystyrene 96-well roundbottom cell plates, 25.000 cells/well in 200 μL of growth media.

4. Grow cells at least one day at 37° C., 5% CO$_2$.

5. Wash cells with D-PBS 1×.

6. Add 200 μL/well of starvation media (DMEM, 2.0 mM 1-Glutamine, 0.1% FBS). Incubate overnight at 37° C., 5% CO$_2$.

7. Dilute Compounds 1:20 in polypropylene 96 well plates using starvation media. Dilute dimethylsulfoxide 1:20 for use in control wells.

8. Remove starvation media from 96 well cell culture plates and add 162 μL of fresh starvation media to each well.

9. Add 18 μL of 1:20 diluted Compound dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 27° C., 5% CO$_2$ for two hours.

10. Remove unbound antibody from ELISA plates by inverting plate to remove liquid, Wash 3 times with TBSW+ 0.5% ethanolamine, pH 7.0. Pat the plate on a paper towel to remove excess liquid and bubbles.

11. Block plates with TBSW+0.5% Ethanolamine, pH 7.0, 150 µL per well. Incubate plate thirty minutes while shaking on a microliter plate shaker.

12. Wash plate 3 times as described in step 10.

13. Add 0.5 µg/well affinity purified anti-FLU-1 polyclonal rabbit antiserum. Bring final volume to 150 µL/well with TBSW+0.5% ethanolamine pH 7.0. Incubate plate for thirty minutes while shaking.

14. Add 180 µL starvation medium to the cells and stimulate cells with 20 µL/well 10.0 mM sodium ortho vanadate and 500 ng/mL VEGF (resulting in a final concentration of 1.0 mM sodium ortho vanadate and 50 ng/mL VEGF per well) for eight minutes at 37° C., 5% $CO_2$. Negative control wells receive only starvation medium.

15. After eight minutes, media should be removed from the cells and washed one time with 200 µL/well PBS.

16. Lyse cells in 150 µL/well HNTG while shaking at room temperature for five minutes. HNTG formulation includes sodium ortho vanadate, sodium pyro phosphate and EDTA.

17. Wash ELISA plate three times as described in step 10.

18. Transfer cell lysates from the cell plate to ELISA plate and incubate while shaking for two hours. To transfer cell lysate pipette up and down while scrapping the wells.

19. Wash plate three times as described in step 10.

20. Incubate ELISA plate with 0.02 µg/well UB40 in TBSW+05% ethanolamine. Bring final volume to 150 µL/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW+0.5% ethanolamine, pH 7.0. Bring final volume to 150 µL/well. Incubate while shaking for thirty minutes.

23. Wash plate as described in step 10.

24. Add 100 µL of $ABTS/H_2O_2$ solution to well. Incubate ten minutes while shaking.

25. Add 100 µL of 0.2 M HCl for 0.1 M HCl final to stop the color development reaction. Shake 1 minute at room temperature. Remove bubbles with slow stream of air and read the ELISA plate in an ELISA plate reader at 410 nm.

The $IC_{50}$ values measured in the FLK-1 receptor phosphorylation assay for the compound of formula VI are depicted in Table 8:

TABLE 8

(VI)

| Compound | $IC_{50}$ (µM) |
|---|---|
| VI | 4.84 |

Cellular/Biologic Assays

Example 10

Assay Measuring the Effect of Indolinone Compounds on the Growth of A431 Cells

The following assay measures growth rates for A43 1 cells.

Materials
96-well flat bottom sterile plates
96-well round bottom sterile plates
sterile 25 mL or 100 mL reservoir
pipets, multi-channel pipetman
sterile pipet tips
sterile 15 mL and 50 mL tubes
Reagents
0.4% SRB in 1% acetic acid
10 mM Tris base
10% TCA
1% acetic acid
sterile DMSO (Sigma)
compound in DMSO (100 mM or less stock solution)
Trypsin-EDTA (GIBCO BRL)
Cell line:
A431 cells (ATCC CRL 1555)
Growth medium:
2% calf serum/DMEM+2 mM glutamine, Pen/Strep
Protocol
Day 0: Cell Plating:
This part of assay is carried out in a laminar flow hood.
  1. Trypsinize cells. Transfer 200 µL of cell suspension to 10 mL of isotone. Count cells with a Coulter Counter.
  2. Dilute cells in growth medium to 60,000 cell/mL. Transfer 100 µL of cells to each well in a 96-well flat bottom plate to give 6000 cells/well.
  3. Use half of plate (4 rows) for each comound and quadruplicate wells for each comound concentration, and a set of 4 wells for medium control.
  4. Gently shake plates to allow for uniform attachment of the cells.
  5. Incubate the plates at 37° C. in a 10% $CO_2$ incubator.
Day 1: Addition of Compound:
This part of assay is carried out in a laminar flow hood.
  1. In a 96-well round bottom plate, add 120 µL of growth medium containing 2×final % DMSO found in highest screening concentration of compound to columns 1 to 11. For example, if the highest concentration is 100 µL, ad this is made from a 100 mM stock, 1×DMSO is 0.1%, so 2×DMSO is 0.2%. This plate is used to titrate out the compound, 4 rows per compound.
  2. In a sterile 15 mL tube, make a 2×solution of the highest screening concentration of compound in growth medium plus 2×DMSO. 1 mL per cell line is needed. The starting concentration of the compound is usually 100 µM but this concentration may vary depending upon the solubility of the compound.
  3. Transfer 240 µL of the 2×starting compound solution to qudruplicate wells in column 12 of the 96-well round bottom plate. Do 1:2 serial dilutions across the plate from right to left by transferring 12 µL from column 12 to column 11, column 11 to 10 and so on through column 2. Transfer 100 µL of compound dilutions, and 100 µL of medium in column 1, onto 100 µL medium on cells in corresponding wells of 96-well flat bottom plate. Total volume per well should be 200 µL.
  4. Return the plate to the incubattor and incubate for 3 days.
Day 4: Development of Assay
This party of assay is carried out on the bench.
  1. Aspirate or pour off medium. Add 200 µL cold 10% TCA to each well to fix cells. Incubate plate for at least 60 min. at 4° C.
  2. Discard TCA and rinse wells 5 times with tap water. Dry plates upside down on paper towels.

3. Stain cells with 100 μL/well 0.4% SRB for 10 min.
4. Pour of SRB and rinse wells 5 times with 1% acetic acid. Dry plates completely upside down on paper towels.
5. Solubilize dye with 100 μL/well 10 mM Tris base for 5–10 min. on shaker.
6. Read plates on Dynatech ELISA Plate REader at 570 nm with reference at 630 nm.

Compound of formula VI inhibited the growth rate of A431 cells as illustrated in Table 9.

TABLE 9

(VI)

| Compound | IC$_{50}$ (μM)<br>A431 2% |
|---|---|
| VI | 0.712 |

Example 11

Assay Measuring the Effect of Indolinone Compounds on the Growth of SKOV3 Cells

The assay is the same as the assay set forth in EXAMPLE 10, except that SKOV3 cells (ATCC HTB77) are used instead of A431 cells.

Compound of formula VI inhibited the growth rate of SKOV3 cells as illustrated in Table 10.

TABLE 10

(VI)

| Compound | IC$_{50}$ (μM)<br>SKOV3 2% |
|---|---|
| VI | 1.08 |

Example 12

Assay Measuring the Effect of Indolinone Compounds on the Growth of C6 Cells

The assay is the same as the assay set forth in EXAMPLE 10, except that C6 cells (ATCC 107) are used instead of A431 cells.

Compound of formula VI inhibited the growth rate of C6 cells as illustrated in Table 11.

TABLE 11

(VI)

| Compound | IC$_{50}$ (μM)<br>C6 2% |
|---|---|
| VI | 1.55 |

Example 13

PDGF-Induced BRDU Incorporation Assay

Materials and Reagents (1) PDGF: human PDGF B/B; 1276-956, Boehringer Mannheim, Germany (2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No.11647 229, Boehringer Mannheim, Germany.

(5) TMB Substrate Solution: tetramethylbenzidine (TME), ready to use, Cat. No. 1 647 229, Boehringer Mannheim, Germany.

(6) PBS Washing Solution: 1×PBS, pH 7.4, made in house.

(7) Albumin, Bovine (BSA): fraction V powder; A-8551, Sigma Chemical Co., USA.

(8) 3T3 cell line genetically engineered to express human PDGF-R.

Protocol (1) Cells are seeded at 8000 cells/well in DMBEM, 10% CS) 2 mM Gln in a 96 well plate. Cells are incubated overnight at 37° C. in 5% CO$_2$.

(2) After 24 hours, the cells are washed with PBS, and then are serum starved scram free medium (0% CS DMEM with 0.1% BSA) for 24 hours.

(3) On day 3, ligand (PDGF=3.8 nM, prepared in DMEM with 0.1% BSA) and test compounds are added to the cells simultaneously. The negative control wells receive serum free DMEM with 0.1% BSA only; the positive control cells receive the ligand (PDGF) but no test compound. Test compounds are prepared in serum free DMEM with ligand in a 96 well plate, and serially diluted for 7 test concentrations.

(4) After 20 hours of ligand activation, diluted BrdU labeling reagent (1:100 in DMEM, 0.1% BSA) is added and the cells are incubated with BrdU (final concentration=10 μM) for 1.5 hours, (5) After incubation with labeling reagent, the medium is removed by decanting and tapping the inverted plate on a paper towel. FixDenat solution is added (50 μL/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 µL/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 µL/well), and the plate is incubated for 90 minutes at room temperature on a plate shaker.

(8) The antibody conjugate is thoroughly removed by decanting and rinsing the wells 5 times with PBS, and the space is dried by inverting and tapping on a paper towel.

(9) TMB substrate solution is added (100 µL/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

The $IC_{50}$ values measured for the compound of formula VI are depicted in Table 12:

TABLE 12

(VI)

| Assay | $IC_{50}$ (µM) |
|---|---|
| 3T3EGFR EGF | 7.03 |
| 3T3EGFR PDGF | 7.00 |

Example 14

HUV-EC-C Assay

The following protocol may also be used to measure a compound's activity against PDGF-R, FGF-R or Flk-1/KDR, all of which are naturally expressed by HUV-EC cells.

DAY 0

1. Wash and trypsinize HUV-EC-C cells (human umbilical vein endothelial cells, (American Type Culture Collection; catalogue no. 1730 CRL). Wash with Dulbecco's phosphate-buffered saline (D-PBS; obtained from Gibco BRL, catalogue no. 14190-029) 2 times at about 1 mL/10 $CM^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 mL/25–30 $cm^2$ of tissue culture flask for about 5 minutes at 37° C. After cells have detached from the flask, add an equal volume of assay medium and transfer to a 50 mL sterile centrifuge tube (Fisher Scientific; catalogue no. 05-539-6).

2. Wash the cells with about 35 mL assay medium in the 50 mL sterile centrifuge tube by adding the assay medium, centrifuge for 10 minutes at approximately 200×g aspirate the supernatant and resuspend with 35 mL D-PBS. Repeat the wash two more times with D-PBS, resuspend the cells in about 1 mL assay medium/15 $cm^2$ of tissue culture flask. Assay medium consists of F12K medium (Gibco BRL; catalogue no. 21127-014)+0.5% heat-inactivated fetal bovine serum. Count the cells with a Coulter Counter® Coulter Electronic, Inc.) and add assay medium to the cells to obtain a concentration of $0.8–1.0×10^5$ cells/mL.

3. Add cells to 96-well flat-bottom plates at 100 µL/well or $0.8–1.0×10^4$ cells/well; incubate ~24 h at 37° C., 5% $CO_2$.

DAY 1

1. Make up two-fold drug titrations in separate 96-well plates, generally 50 µM on down to 0 µM. Use the same assay medium as mentioned in day 0, step 2 above. Titrations are made by adding 90 µL/well of drug at 200 µM (4× the final well concentration) to the top well of a particular plate column. Since the stock drug concentration is usually 20 mM in DMSO, the 200 µM drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 µL/well. Take 60 µL from the 120 µL of 200 µM drug dilution in the top well of the column and mix with the 60 µL in the second well of the column. Take 60 µL from his well and mix with the 60 µL in the third well of the column, and go on until two-fold titrations are completed. When the next-to-the-last well is mixed, take 60 µL of the 120 µL in this well and discard it. Leave the last well with 60 µL of DMSO/media diluent as a non-drug-containing control. Make 9 columns of titrated drug, enough for triplicate wells each for 1) VEGF (obtained from Pepro Tech Inc., catalogue no. 100~200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 µL/well of the drug dilutions to the 96-well assay plates containing the $0.8–1.0×10^4$ cells/100 µL/well of the HUV-PC-C cells from day 0 and incubate ~2 h at 37° C., 5% $CO_2$.

3. In triplicate, add 50 µL/well of 80 µg/mL VEGF, 20 ng/mL ECGF, or media control to each drug condition. As with the drugs, the growth factor concentrations are 4× the desired final concentration. Use the assay media from day 0 step 2 to make the concentrations of growth factors. Incubate approximately 24 hours at 37° C., 5% $CO_2$. Each well will have 50 µL drug dilution, 50 µL growth factor or media, and 100 µL cells,=200 µL/well total. Thug the 4× concentrations of drugs and growth factors become 1× once everything has been added to the wells.

DAY 2

1. Add $^3$H-thymidine (Amersham; catalogue no. TRK-686) at 1 µCi/well (10 µL/well Of 100 µCi/mL solution made up in RPMI media+10% heat-inactivated fetal bovine serum) and incubate ~24 h at 37° C., 5% $CO_2$. Note: $^3$H-thymidine is made up in RPMI media because all of the other applications for which we use the $^3$H-thymidine involve experiments done in RPMI. The media difference at this step is probably not significant. RPMI was obtained from Gibco BRL, catalogue no. 11 875-051.

DAY 3
1. Freeze plates overnight at 20° C.

DAY 4
1. Thaw plates and harvest with a 96-well plate harvester (Tomtec Harvester 96®) onto filter mats (Wallac; catalogue no. 1205-401); read counts on a Wallac Betaplate liquid scintillation counter.

The $IC_{50}$ values measured for the compound of formula VI are depicted in Table 13:

TABLE 13

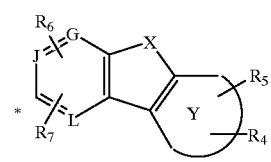

(VI)

| Assay | $IC_{50}$ ($\mu$M) |
|---|---|
| HUVEC vEGF | 0.68 |
| HUVEC aFGF | 0.63 |

CONCLUSION

One skilled in the a would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. An indolinone compound having a structure set forth in formula I:

(I)

wherein
(A) Q is an optionally substituted oxindole moiety bonded with the rest of the molecule through position 3 of the oxindole ring; and
(B) T is a ring moiety having the structure set forth in formula III:

(III)

wherein
(a) $R_4$, $R_5$, $R_6$, and $R_7$ are independently selected from the group consisting of
  (i) hydrogen;
  (ii) saturated or unsaturated alkyl optionally substituted with one or more substituents independently selected from the group consisting of halogen, trihalomethyl, carboxylate, nitro, ester, and a five-membered or six-membered aromatic, heteroaromatic, aliphatic, or heteroaliphatic ring moiety, wherein said ring moiety is optionally substituted with one, two, or three substituents independently selected from the group consisting of alkyl, halogen, trihalomethyl, carboxylate; nitro, and ester moieties;
  (iii) an aromatic or heteroaromatic ring optionally substituted with one, two, or three substituents independently selected from the group consisting of alkyl, alkoxy, halogen, trihalomethyl, carboxylate, nitro, and ester moieties;

(iv) an aliphatic or heteroaliphatic ring optionally substituted with one, two, or three substituents independently selected from the group consisting of alkyl, alkoxy, halogen, trihalomethyl, carboxylate, nitro, ester, and an aromatic or heteroaromatic ring optionally substituted with one, two, or three substituents independently selected from the group consisting of alkyl, alkoxy, halogen, trihalomethyl, carboxylate, nitro, and ester moieties;

(v) an amine of formula $—(X_1)_{n1}—NX_2X_3$, wherein $X_1$ is selected from the group consisting of saturated or unsaturated alkyl and five-membered or six-membered aromatic, heteroaromatic, or aliphatic ring moieties and wherein n1 is 0 or 1, and wherein $X_2$ and $X_3$ are independently selected from the group consisting of hydrogen, saturated or unsaturated alkyl, and five-membered or six-membered aromatic, heteroaromatic, or aliphatic ring moieties;

(vi) a nitro of formula $—NO_2$;

(vii) a halogen or trihalomethyl;

(viii) a ketone of formula $—(X_4)_{n4}—CO—X_5$, wherein $X_4$ and $X_5$ are independently selected from the group consisting of alkyl optionally substituted with halogen, trihalomethyl, carboxylate, nitro, ester, and five-membered or six-membered aromatic, heteroaromatic, alipathic, or heteroaliphatic ring moieties, wherein said ring moieties are optionally substituted with one, two, or three substituents independently selected Tom the group consisting or alkyl, halogen, trihalomethyl, carboxylate, nitro, and ester moieties and wherein n4 is 0 or 1;

(ix) a carboxylic acid of formula $—(X_6)_{n6}—COOH$ or ester of formula $—(X_7)_{n7}—COO—X_8$, wherein $X_6$, $X_7$, and $X_8$ and are independently selected from the group consisting of alkyl and five-membered or six-membered aromatic, heteroaromatic, aliphatic, or heteroaliphatic ring moieties and wherein n6 and n7 are independently 0 or 1;

(x) an alcohol of formula $—(X_9)_{n9}—OH$ or an alkoxyalkyl moiety of formula $—(X_{10})_{n10}—O—X_{11}$, wherein $X_9$, $X_{10}$, and $X_{11}$ are independently selected from the group consisting of saturated or unsaturated alkyl, and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, nitro, and ester and wherein n9 ad n10 are independently 0 or 1;

(xi) an amide of formula $—(X_{12})_{n12}—NHCOX_{13}$, or of formula $—(X_{14})_{n14}—CONX_{15}X_{16}$, wherein $X_{12}$ and $X_{14}$ are each independently selected from the group consisting of alkyl hydroxyl, and five-membered or six-membered aromatic, heteroaromatic, aliphatic, or heteroaliphatic ring moieties, wherein said ring is optionally substituted with one or more substituents independently selected from the group consisting of alkyl, halogen, thihalomethyl, carboxylate, nitro, and ester and wherein n12 and n14 are independently 0 or 1, and wherein $X_{13}$, $X_{14}$, $X_{15}$, and $X_{16}$ are each independently selected from the group consisting of hydrogen, alkyl, hydroxyl, and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, nitro, and ester;

(xii) a sulfonamide of formula $—(X_{17})_{n17}—SO_2NX_{18}X_{19}$, wherein $X_{17}$ is selected from the group consisting of alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and wherein $X_{18}$, and $X_{19}$ are independently selected from the group consisting of hydrogen, alkyl, five-membered or six-membered aromatic, heteroaromatic, aliphatic, or heteroaliphatic ring moieties optionally substituted with one or more substituents independently selected from the group consisting of alkyl, halogen, trihalomethyl, carboxylate, nitro, or ester, and wherein $X_{18}$ and $X_{19}$ taken together form a five-membered or six-membered aliphatic or heteroaliphatic ring optionally substituted with one or more substituents independently selected from the group consisting of alkyl, halogen trihalomethy, carboxylate, nitro, and ester, and wherein n17 is 0 or 1;

(xiii) an aldehyde of formula $—(X_{20})_{n20}—CO—H$ wherein $X_{20}$ is selected from the group consisting of saturated or unsaturated alkyl, and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, nitro, and ester and wherein n20 is 0 or 1;

(xiv) a sulfone of formula $—(X_{21})_{n21}—SO_2—X_{22}$, wherein $X_{22}$ is selected from the group consisting of hydroxide, saturated or unsaturated alkyl and five-membered or six-membered aryl or heteroaryl moieties and wherein $X_{21}$ is selected from the group consisting of saturated or unsaturated alkyl, and five-membered or six-membered aromatic, heteroaromatic, aliphatic, or heteroaliphatic ring moieties, wherein said ring is optionally substituted with one or more substituents independently selected from the group consisting of alkyl, halogen,trihalomethyl, carboxylate, nitro, and ester and wherein n21 is 0 or 1; and (xv) a thiol of formula $(X_{23})_{n23}—SH$ or a thioether of formula $—(X_{24})_{n24}—S—X_{25}$, wherein $X_{23}$ and $X_{24}$ are independently selected from the group consisting of saturated or unsaturated alkyl, and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, nitro, and ester, and wherein n23 and n24 are independently 0 or 1, and wherein $X_{25}$ is selected from the group consisting of hydrogen, saturated or unsaturated alkyl, and five-membered or six-membered aromatic, heteroaromatic, aliphatic, or heteroaliphatic ring moieties, wherein said ring is optionally substituted with one or more substituents independently selected from the group consisting of alkyl, halogen, trihalomethyl, carboxylate, nitro, and ester;

(b) X is selected from the group consisting of $NX_{26}$, sulfur, SO, $SO_2$, and oxygen, where $X_{26}$ is selected from the group consisting of
  (i) hydrogen;
  (ii) saturated or unsaturated alkyl optionally substituted with a five-membered or six-membered aryl or heteroaryl ring moiety, wherein said rings moiety is optionally substituted with one, two, or three substituents independently selected from the group consisting of alkyl, halogen, trihalomethyl, carboxylate, nitro, and esther moieties;
  (iii) an aryl optionally substituted with one, two, or three substituents independently selected from the group consisting of alkyl, alkoxy, halogen, trihalomethyl, carboxylate, nitro, and ester moieties;
  (iv) a sulfone of formula $-SO_2-X_{27}$, wherein $X_{27}$ is selected from the group consisting of saturated or unsaturated alkyl and five-membered or six-membered aryl or heteroaryl moieties; and
  (v) an acyl of formula $-C(O)X_{28}$, wherein $X_{28}$ is selected from the group consisting of hydrogen saturated and unsaturated alkyl, aryl, and a five-membered or six-membered ring moiety;

c) ring Y is selected from the group consisting of five-membered, six-membered, and seve-membered aromatic heteroaromatic, or non-aromatic rings, wherein said heteroaromatic ring contains a heteroatom selected from the group consisting of nitrogen, oxygen, and sulfur, and when said non-aromatic ring in combination with $R_4$ optionally forms a carbonyl functionality;

(d) G, J, and L are selected from the group consisting of carbon and nitrogen; and (e) T is bonded to the rest of the molecule at the position of the ring marked with an asterisk (*) in formula III.

2. The compound of claim 1, wherein Q is selected from the group consisting of:

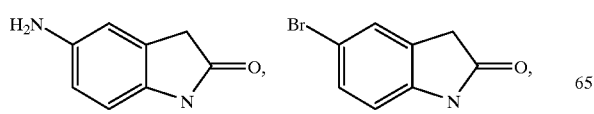

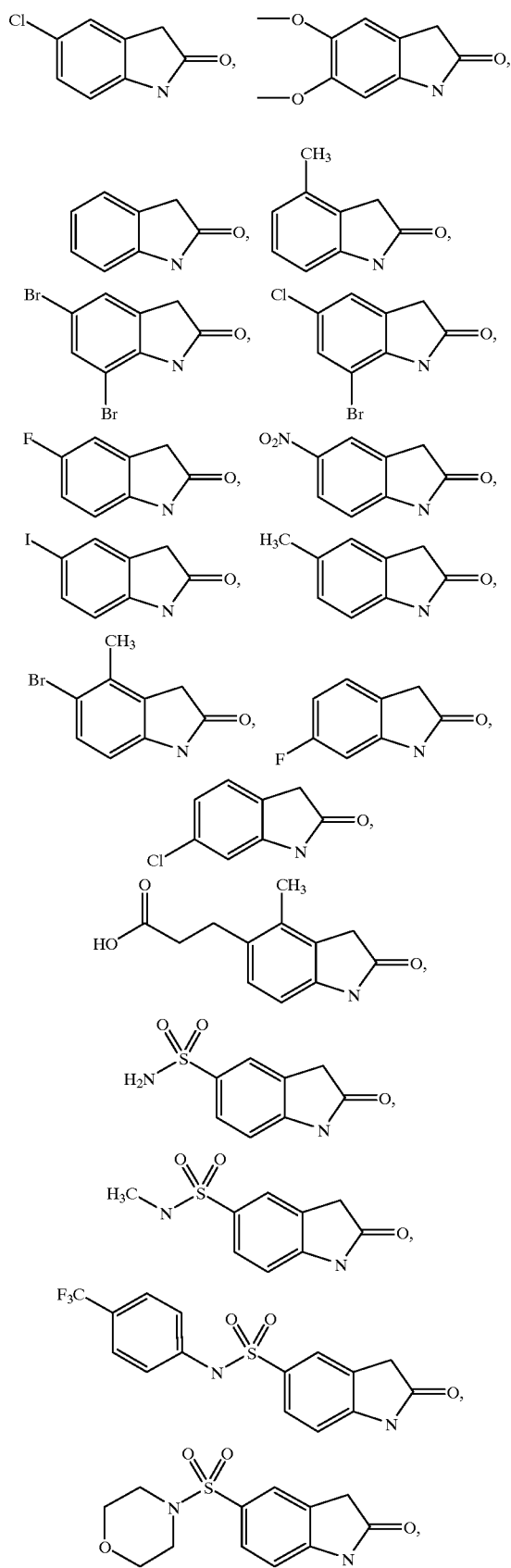

101
-continued
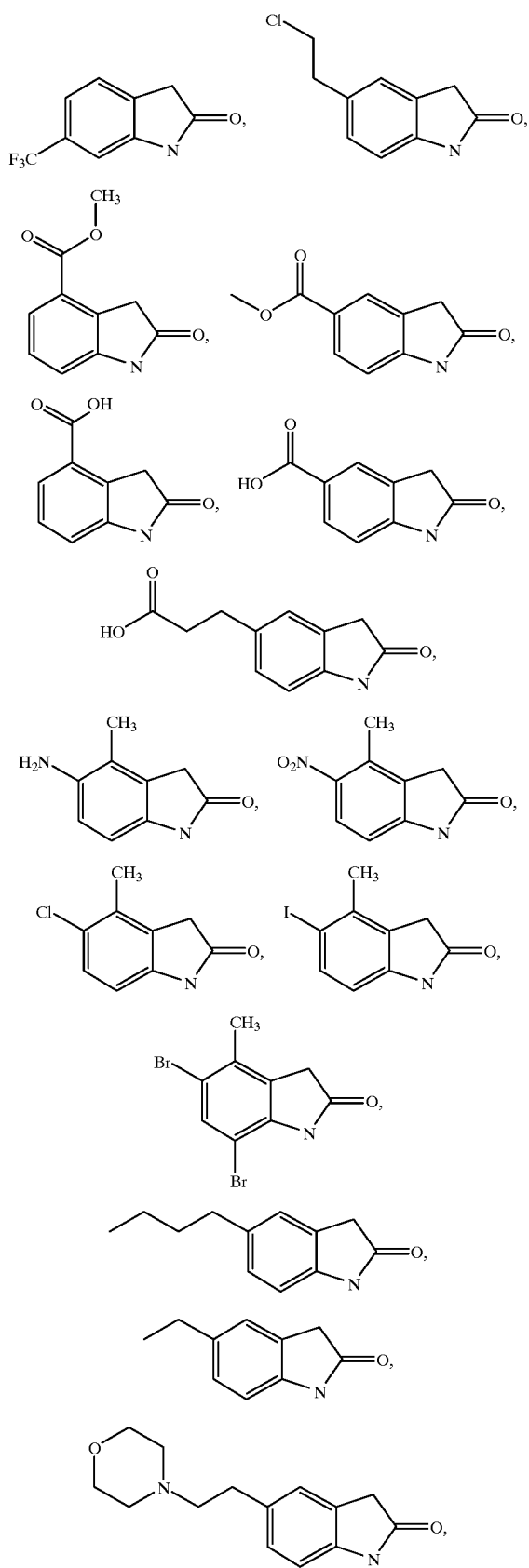
102
-continued
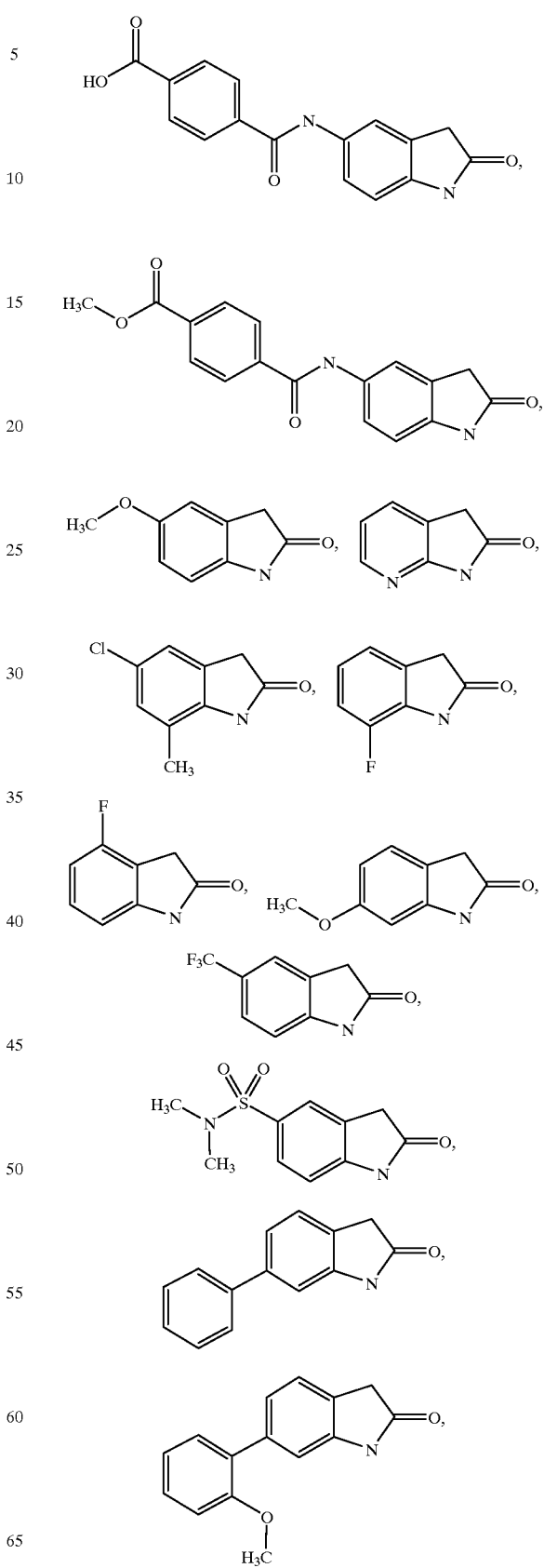

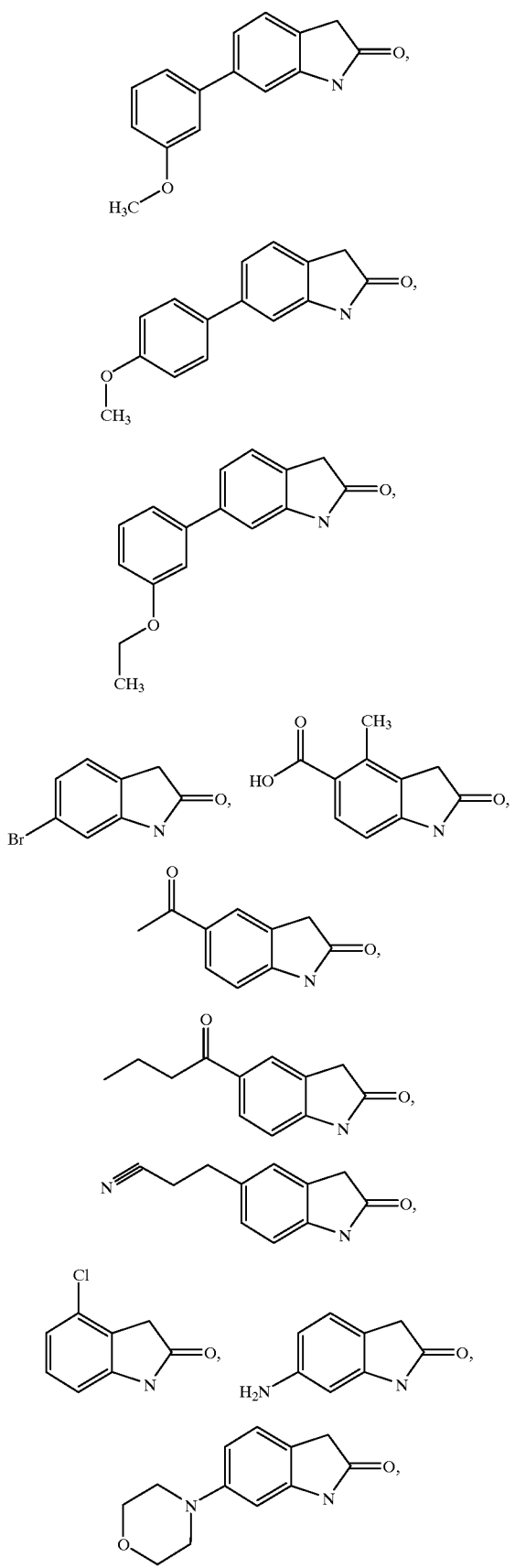
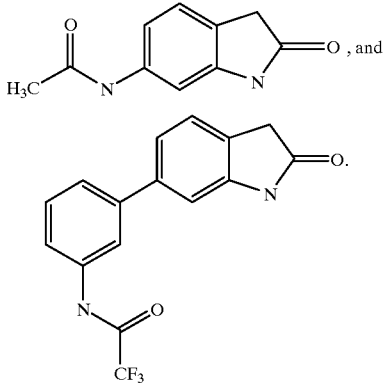

3. The compound of claim 1, wherein $R_4$ and $R_5$ are independently selected from the group consisting of
(i) hydrogen;
(ii) methyl, ethyl, propyl, and butyl groups optionally substituted with substituents selected from the group consisting of halogen, trihalomethyl, cyano, and nitro moieties;
(iii) an amine of formula —$(X_1)_{n1}$—$NX_2X_3$, wherein $X_2$ and $X_3$ are independently selected from the group consisting of hydrogen and optionally substituted saturated alkyl, and $X_1$ is optionally substituted saturated alkyl, and wherein n1 is 0 or 1, or wherein $X_2$ and $X_3$ taken together form a five-membered or a six-membered aliphatic or heteroaliphatic ring, optionally substituted at a ring carbon atom or hetero atom with a substituent selected from the group consisting of methyl, ethyl, propyl, phenyl, and alkoxyphenyl;
(iv) a nitro of formula —$NO_2$;
(v) a halogen or trihalomethyl;
(vi) a ketone of formula —CO—$X_4$, wherein $X_4$ is selected from the group consisting of methyl, ethyl, propyl, n-butyl, and t-butyl;
(vii) a carboxylic acid of formula —$(X_6)_{n6}$—COOH or ester of formula —$(X_7)_{n7}$—COO—$X_8$, wherein $X_6$ and $X_7$ are selected from the group consisting of a bond, methylene, ethylene, and propylene, and wherein $X_8$ is selected from the group consisting of methyl and ethyl, and wherein n6 and n7 are independently 0 or 1;
(viii) an amide of formula —$NHCOX_{13}$, or of formula —$CONX_{15}X_{16}$, wherein $X_{13}$, $X_{15}$, and $X_{16}$ are each independently selected from the group consisting of hydrogen, methyl, ethyl, propyl, and phenyl;
(ix) a sulfonamide of formula —$SO_2NX_{18}X_{19}$, wherein $X_{18}$ and $X_{19}$ are independently selected from the group consisting of hydrogen, methyl, and ethyl;
(x) an alcohol of formula —$(X_9)_{n9}$—OH or an alkoxyalkyl moiety of formula —$(X_{10})_{n10}$—O—$X_{11}$, wherein $X_9$, and $X_{10}$ are independently selected form the group consisting of methylene, ethylene, and propylene, and wherein $X_{11}$ is independently selected from the group consisting of methyl, ethyl, and propyl, and wherein n9 and n10 are independently 0 or 1;
(xi) a sulfone of formula —$(X_{21})_{n21}$—$SO_2$—$X_{22}$, wherein $X_{22}$ is selected from the group consisting of hydroxide, saturated or unsaturated alkyl and five-membered or six-membered aryl or heteroaryl moieties, and wherein $X_{21}$ is saturated alkyl, and wherein n21 is 0 or 1; and
(xii) a thioether of formula —$(X_{24})_{n24}$—S—$X_{25}$, wherein $X_{24}$ is independently selected from the group consisting of methylene, ethylene, and propylene, and wherein $X_{25}$ is independently selected from the group consisting of methyl, ethyl, propyl, and phenyl, and wherein n24 is 0 or 1.

4. The compound of claim 3, wherein $R_4$ and $R_5$ are independently selected from the group consisting of
(i) hydrogen;
(ii) methyl and ethyl;
(iii) an amine of formula —$(X_1)_{n1}$—$NX_2X_3$, wherein $X_2$ and $X_3$ are independently selected from the group consisting of hydrogen methyl and ethyl, and $X_1$ is methylene or ethylene, and wherein n1 is 0 or 1, or wherein $X_2$ and $X_3$ taken together form an optionally substituted ring selected from the group consisting of

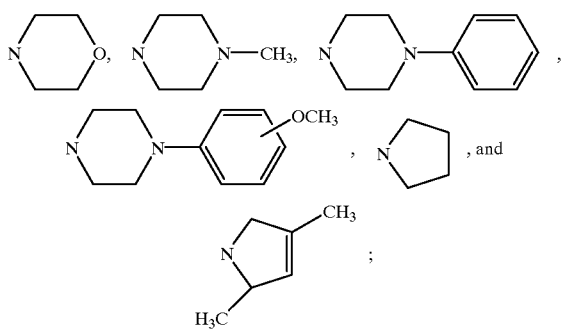

(iv) a nitro of formula —$NO_2$;
(v) a halogen;
(vi) a ketone of formula —CO—$X_4$, wherein $X_4$ is selected from the group consisting of methyl and t-butyl;
(vii) a carboxylic acid of formula —$(X_6)_{n6}$—COOH or ester of formula —$(X_7)_{n7}$—COO—$X_8$, wherein $X_6$ and $X_7$ are selected from the group consisting of a bond, methylene, ethylene, and propylene, and wherein $X_8$ is selected from the group consisting of methyl and ethyl, and wherein n6 and n7 are independently 0 or 1;
(viii) an amide of formula —$NHCOX_{13}$, or of formula —$CONX_{15}X_{16}$, wherein $X_{13}$, $X_{15}$, and $X_{16}$ are each independently selected from the group consisting of hydrogen, methyl, and phenyl;
(ix) a sulfonamide of formula —$SO_2NX_{18}X_{19}$, wherein $X_{18}$ and $X_{19}$ are independently selected from the group consisting of hydrogen, methyl, and ethyl;
(x) an alcohol of formula —$(X_9)_{n9}$—OH or an alkoxyalkyl moiety of formula —$(X_{10})_{n10}$—O—$X_{11}$, wherein $X_9$, and $X_{10}$ are independently selected form the group consisting of methylene, ethylene, and propylene, and wherein $X_{11}$ is independently selected from the group consisting of methyl ethyl, and propyl, and wherein n9 and n10 are independently 0 or 1;
(xi) a sulfone of formula —$SO_2OH$; and
(xii) a thioether of formula —S-phenyl.

5. The compound of claim 3, wherein $R_6$ and $R_7$ are independently selected from the group consisting of
(i) hydrogen;
(ii) methyl, ethyl, propyl, and butyl groups optionally substituted with halogen, trihalomethyl, cyano, and nitro moieties;
(iii) an amine of formula —$(X_1)_{n1}$—$NX_2X_3$, wherein $X_2$ and $X_3$ are independently selected from the group consisting of hydrogen and optionally substituted saturated alkyl, and $X_1$ is an optionally substituted saturated alkylene, and wherein n1 is 0 or 1;
(iv) a halogen or trihalomethyl;
(v) an alcohol of formula —$(X_9)_{n9}$—OH or an alkoxyalkyl moiety of formula $(X_{10})_{n10}$—O—$X_{11}$, wherein $X_9$, and $X_{10}$ are independently selected form the group consisting of methylene, ethylene, and propylene, and wherein $X_{11}$ is selected from the group consisting of methyl, ethyl, and propyl, and wherein n9 and n10 are independently 0 or 1.

6. The compound of claim 5, wherein $R_6$ and $R_7$ are independently selected from the group consisting of
(i) hydrogen;
(ii) methyl and ethyl;
(iii) an amine of formula —$(X_1)_{n1}$—$NX_2X_3$, wherein $X_2$ and $X_3$ are independently selected from the group consisting of hydrogen, methyl, and ethyl, and $X_1$ is selected from the group consisting of methylene and ethylene, and wherein n1 is 0 or 1;
(iv) a halogen;
(v) a hydroxy —OH or an alkoxy moiety of formula —O—$X_{11}$, wherein $X_{11}$ is independently selected form the group consisting of methyl, ethyl, and propyl.

7. The compound of claim 6, wherein Y is a six-membered aromatic or heteroaromatic ring.

8. The compound of claim 6, wherein Y is a six-membered aliphatic or heteroaliphatic ring.

9. The compound of claim 8, wherein Y forms a ring selected from the group consisting of optionally substituted

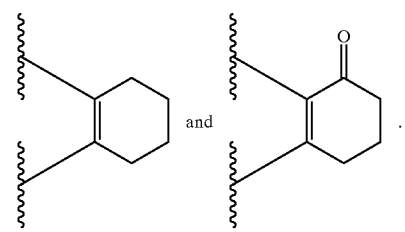

10. The compound of claim 6, wherein G is nitrogen.
11. The compound of claim 6, wherein J is nitrogen.
12. The compound of claim 6, wherein L is nitrogen.
13. The compound of claim 6, wherein X is nitrogen, optionally substituted with alkyl.
14. The compound of claim 6, wherein X is selected from the group consisting of sulfur, SO, and $SO_2$.
15. The compound of claim 6, wherein X is oxygen.
16. The compound of claim 6, wherein T is selected from the group consisting of:

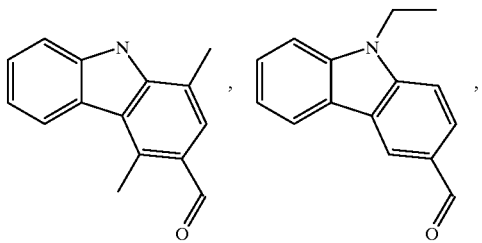

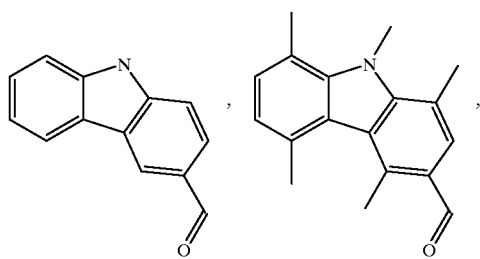
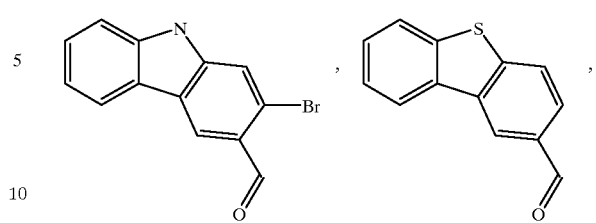
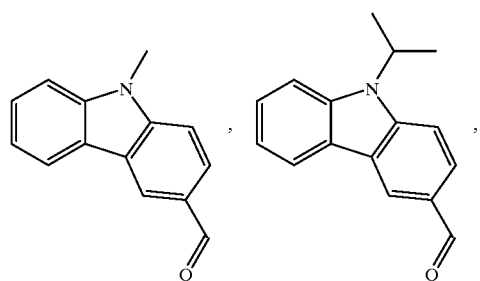
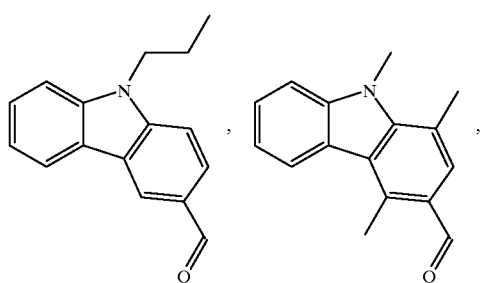
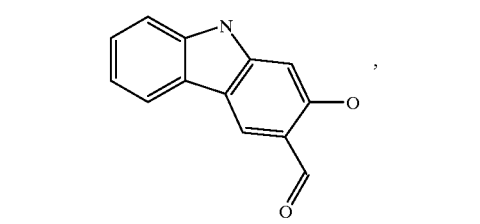
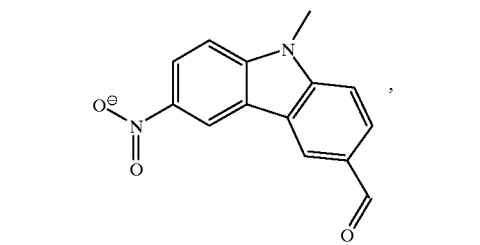
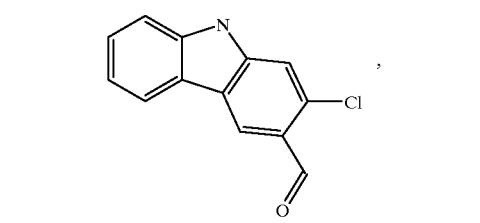

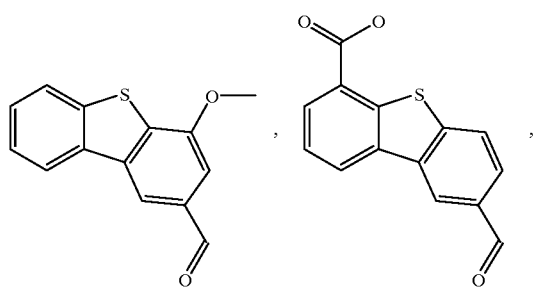,
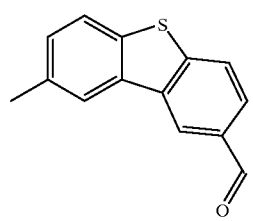,
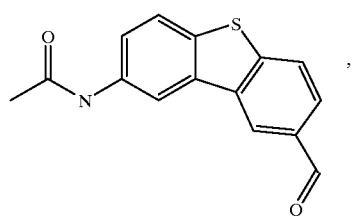,
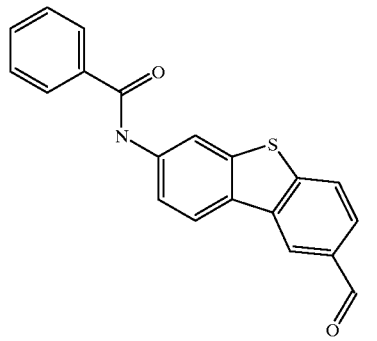,
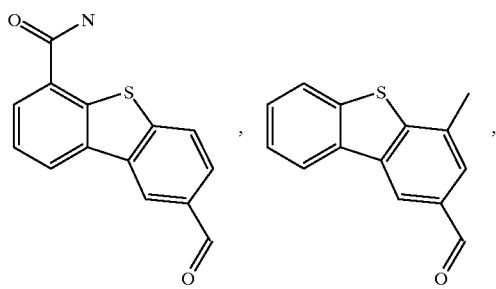,
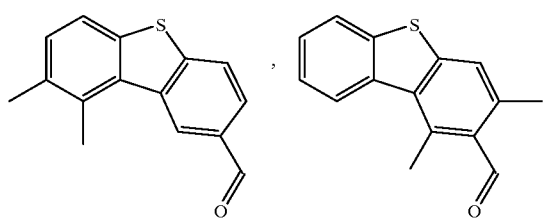,
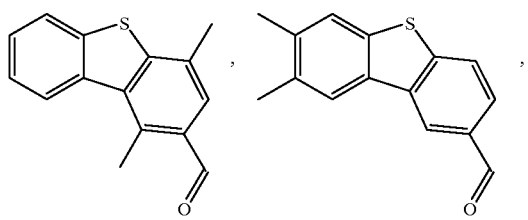,
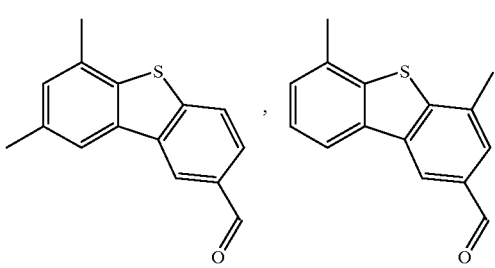,
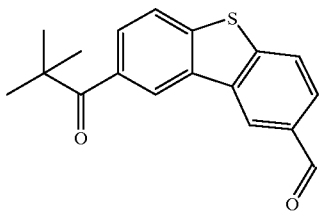,
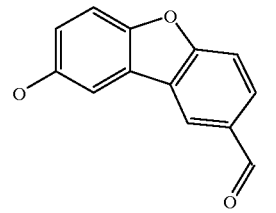,
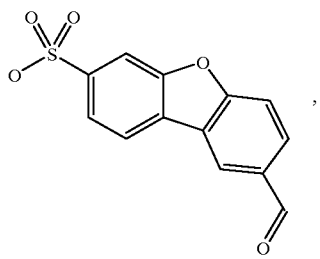,
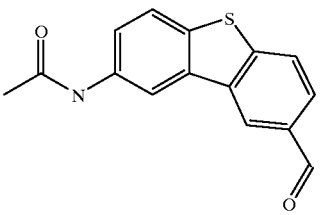,
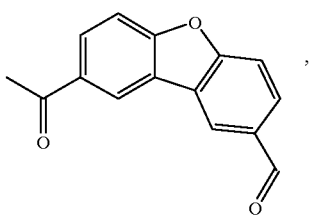,

111
-continued
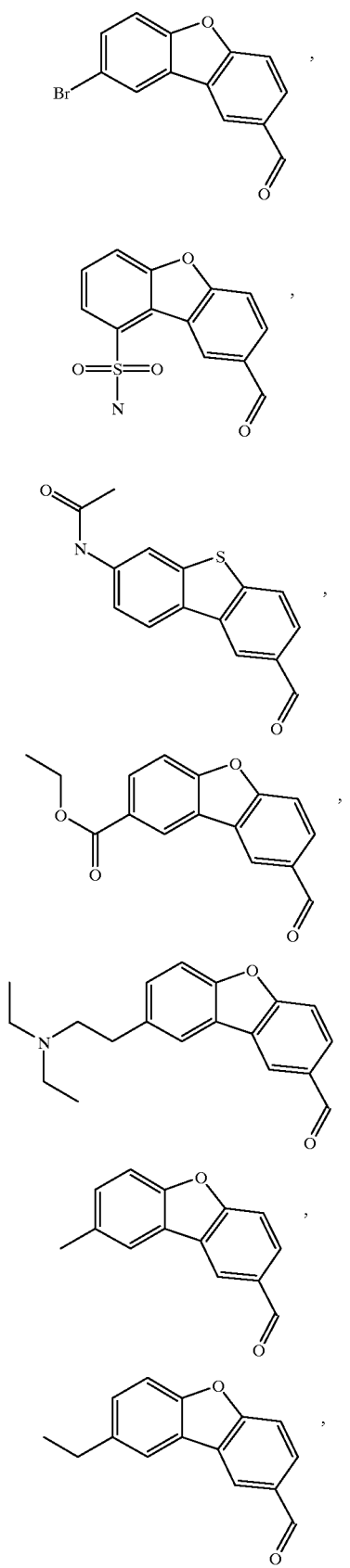
112
-continued
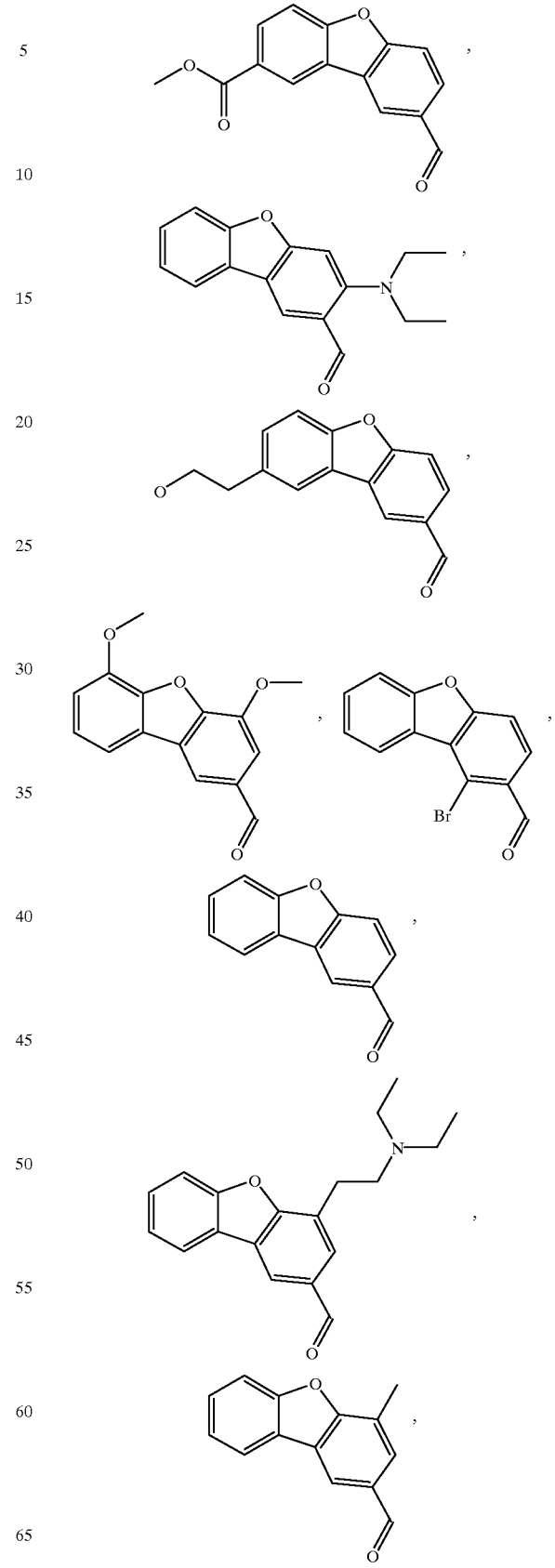

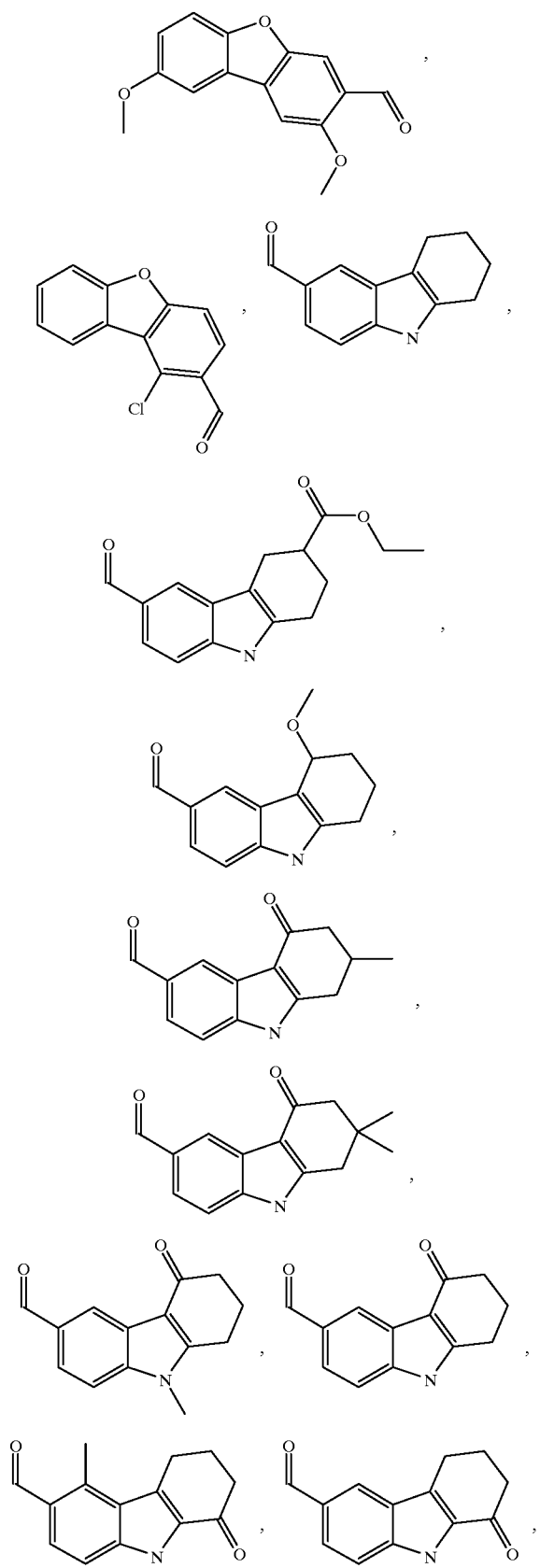
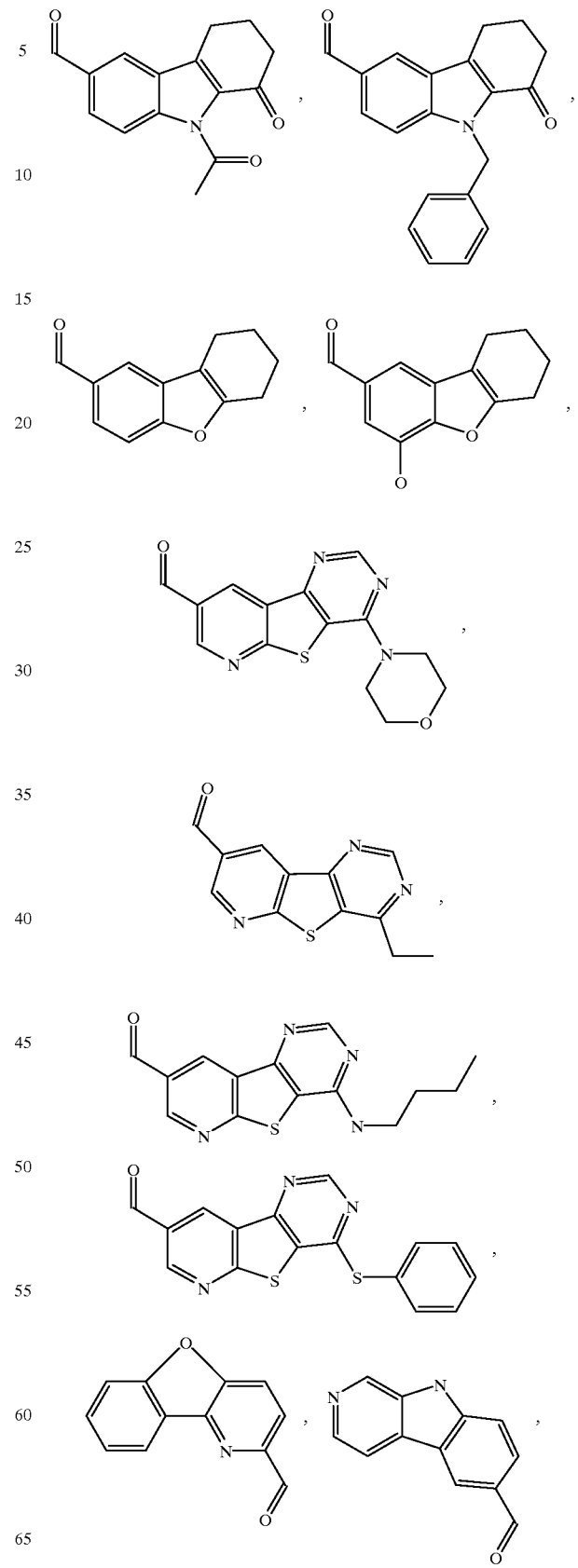

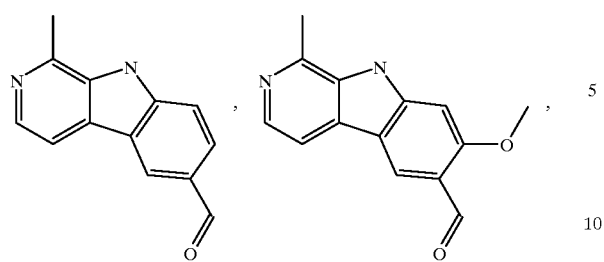
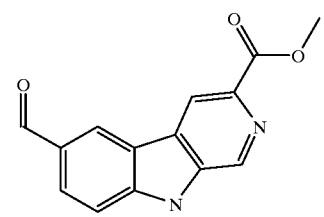
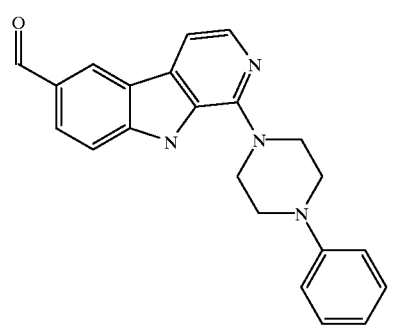
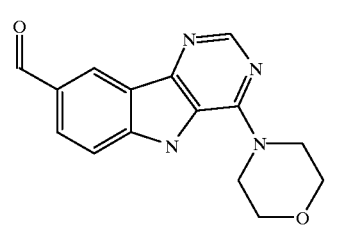
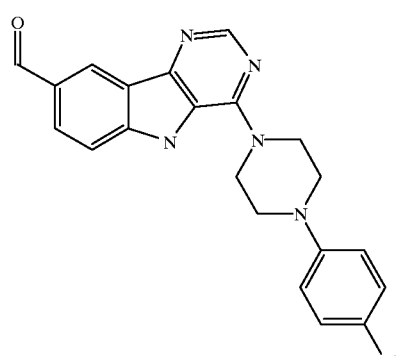
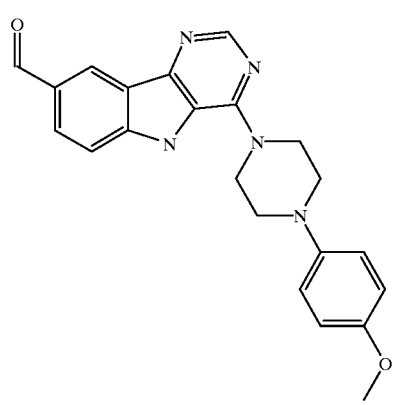

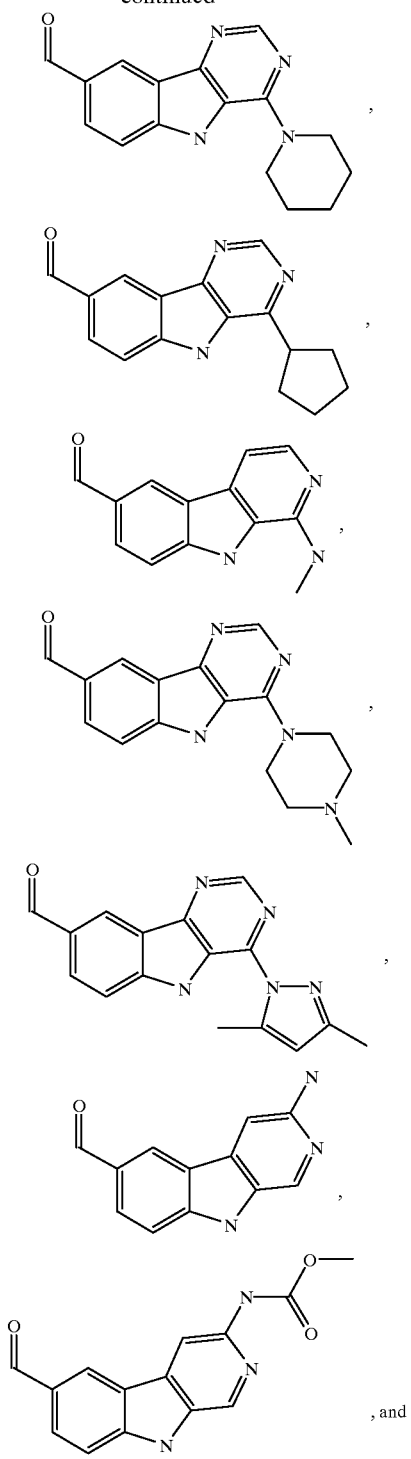

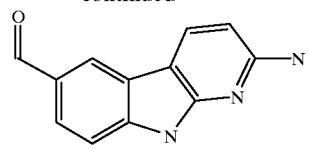

, and

17. A pharmaceutical composition comprising
   (i) a physiologically acceptable carrier, diluent, or excipient; and
   (ii) a compound according to claim 1, or a salt thereof.

18. A method of modulating the function of a protein tyrosine kinase with an indolinone compound according to claim 1, comprising the step of contacting cells expressing said protein tyrosine kinase with said compound.

19. The method of claim 18, wherein said indolinone compound modulates the activity of said protein tyrosine kinase in vitro.

20. The method of claim 18, wherein said protein tyrosine kinase is HER2.

21. A method for treating a disease related to unregulated tyrosine kinase signal transduction, the method comprising the step of administering to a subject in need thereof a therapeutically effective amount of a compound according to claim 1.

22. A method of modulating tyrosine kinase signal transduction comprising administering to a subject a therapeutically effective amount of a compound according to claim 1.

23. A method of preventing or treating an abnormal condition in an organism, wherein said abnormal condition is associated with an aberration in a signal transduction pathway characterized by an interaction between a protein kinase and a natural binding partner, wherein said method comprises the following steps:
   (a) administering a compound of claim 1; and
   (b) promoting or disrupting the abnormal interaction.

24. The method of claim 23, wherein said organism is a mammal.

25. The method of claim 23, wherein said abnormal condition is cancer.

26. The method of claim 23, wherein said abnormal condition is selected from the group consisting of hypertension, depression, generalized anxiety disorder, phobias, post-traumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders, Parkinson's disease, endocrine disorders, vasospasm, cerebellar ataxia, and gastrointestinal tract disorders.

* * * * *